US012745958B2

(12) United States Patent
Leaper

(10) Patent No.: US 12,745,958 B2
(45) Date of Patent: Sep. 29, 2026

(54) COMMUNICATION DEVICES, METHODS, AND SYSTEMS

(71) Applicant: DATAFEEL INC., Washington, DC (US)

(72) Inventor: Matthew Robert Leaper, Omaha, NE (US)

(73) Assignee: DATAFEEL INC., Washington, DC (US)

( * ) Notice: Subject to any disclaimer, the term of this patent is extended or adjusted under 35 U.S.C. 154(b) by 34 days.

(21) Appl. No.: 18/824,750

(22) Filed: Sep. 4, 2024

(65) Prior Publication Data

US 2025/0176910 A1 Jun. 5, 2025

Related U.S. Application Data

(63) Continuation of application No. 18/626,317, filed on Apr. 3, 2024, now Pat. No. 12,097,161, which is a (Continued)

(51) Int. Cl.
*A61B 5/11* (2006.01)
*A61B 5/00* (2006.01)
(Continued)

(52) U.S. Cl.
CPC ............ *A61B 5/681* (2013.01); *A61B 5/1112* (2013.01); *A61B 5/1114* (2013.01); (Continued)

(58) Field of Classification Search
CPC ... A61B 5/0022; A61B 5/1112; A61B 5/1114; A61B 5/318; A61B 5/4029; (Continued)

(56) References Cited

U.S. PATENT DOCUMENTS 1,844,247 A 2/1932 Freemon
2,088,780 A 8/1937 Follese
(Continued)

FOREIGN PATENT DOCUMENTS

AU 2015202395 A1 5/2015
CA 3040546 A1 10/2019
(Continued)

OTHER PUBLICATIONS

U.S. Appl. No. 16/324,568, filed Nov. 27, 2001, Diec.
(Continued)

*Primary Examiner* — Mark R Gaworecki

(57) ABSTRACT

A communication device comprising a plurality of energy generators, each comprising a plurality of generator elements that are independently operable to output a plurality of different energy types toward the skin, each different energy type being operable to communicate with the brain via the skin; a plurality of housings attachable to the skin, each housing containing one energy generator of the plurality of the plurality of energy generators and having a circumferential wall that surrounds its plurality of generator elements and is operable to direct flows of its different energy types toward the skin; a processing unit operable to receive input data and operate one or more generating elements of one or more energy generators of the plurality of energy generators responsive to the input data; and a plurality of conductors extending between the processing unit and the plurality of energy generators.

30 Claims, 14 Drawing Sheets

Related U.S. Application Data continuation of application No. 18/526,980, filed on Dec. 1, 2023, now Pat. No. 12,036,174, which is a continuation of application No. 18/388,489, filed on Nov. 9, 2023, now Pat. No. 11,931,174, which is a continuation of application No. 18/143,142, filed on May 4, 2023, now Pat. No. 11,864,914, which is a continuation of application No. 18/092,398, filed on Jan. 2, 2023, now Pat. No. 11,684,313, which is a continuation of application No. 17/213,117, filed on Mar. 25, 2021, now Pat. No. 11,589,816, which is a continuation of application No. 16/757,482, filed as application No. PCT/US2018/056814 on Oct. 22, 2018, now Pat. No. 10,959,674.

(60) Provisional application No. 62/676,949, filed on May 26, 2018, provisional application No. 62/575,951, filed on Oct. 23, 2017.

(51) Int. Cl.

| | |
|---|---|
| ***A61H 23/00*** | (2006.01) |
| ***A61H 23/02*** | (2006.01) |
| ***A61N 1/04*** | (2006.01) |
| ***A61N 1/36*** | (2006.01) |
| ***G06F 3/01*** | (2006.01) |
| *A61B 5/318* | (2021.01) |

(52) U.S. Cl.

CPC .......... *A61B 5/4029* (2013.01); *A61B 5/4824* (2013.01); *A61B 5/4848* (2013.01); *A61B 5/486* (2013.01); *A61B 5/6803* (2013.01); *A61B 5/6807* (2013.01); *A61B 5/6824* (2013.01); *A61B 5/6833* (2013.01); *A61H 23/006* (2013.01); *A61H 23/02* (2013.01); *A61N 1/0456* (2013.01); *A61N 1/0484* (2013.01); *A61N 1/0492* (2013.01); *A61N 1/36014* (2013.01); *A61N 1/3603* (2017.08); *G06F 3/016* (2013.01); *A61B 5/0022* (2013.01); *A61B 5/318* (2021.01); *A61B 5/4836* (2013.01); *A61B 5/7435* (2013.01); *A61B 2503/12* (2013.01); *A61B 2560/0214* (2013.01); *A61B 2560/0412* (2013.01); *A61B 2560/0468* (2013.01); *A61B 2562/046* (2013.01); *A61B 2562/164* (2013.01); *A61H 2201/0153* (2013.01); *A61H 2201/0207* (2013.01); *A61H 2201/123* (2013.01); *A61H 2201/1664* (2013.01); *A61H 2205/065* (2013.01); *A61H 2230/065* (2013.01)

(58) Field of Classification Search

CPC ... A61B 5/4824; A61B 5/4836; A61B 5/4848; A61B 5/486; A61B 5/6803; A61B 5/6807; A61B 5/681; A61B 5/6824; A61B 5/6833; A61B 5/7435; A61B 2503/12; A61B 2560/0214; A61B 2560/0412; A61B 2560/0468; A61B 2562/046; A61B 2562/164; A61H 23/006; A61H 23/02; A61H 2201/0153; A61H 2201/0207; A61H 2201/123; A61H 2201/1664; A61H 2205/065; A61H 2230/065; A61N 1/0456; A61N 1/0484; A61N 1/0492; A61N 1/36014; A61N 1/3603; G06F 3/016

See application file for complete search history.

(56) References Cited

U.S. PATENT DOCUMENTS

| | | | |
|---|---|---|---|
| 2,327,222 | A | 8/1943 | Sell |
| 2,431,525 | A | 11/1947 | Vecchio et al. |
| 3,108,268 | A | 10/1963 | Uttal |
| 3,133,539 | A | 5/1964 | Eidus |
| 3,533,397 | A | 10/1970 | Scher |
| 3,594,787 | A | 7/1971 | Ickes |
| 3,705,579 | A | 12/1972 | Morini et al. |
| 3,710,784 | A | 1/1973 | Taylor |
| 3,848,608 | A | 11/1974 | Leonard |
| 4,167,189 | A | 9/1979 | Tachi et al. |
| 4,175,297 | A | 11/1979 | Robbins et al. |
| 4,428,368 | A | 1/1984 | Torii |
| 4,510,939 | A | 4/1985 | Brenman et al. |
| 4,535,784 | A | 8/1985 | Rohlicek et al. |
| 4,573,481 | A | 3/1986 | Bullara |
| 4,585,002 | A | 4/1986 | Kissin |
| 4,607,624 | A | 8/1986 | Jefferson |
| 4,612,934 | A | 9/1986 | Borkan |
| 4,628,933 | A | 12/1986 | Michelson |
| 4,651,716 | A | 3/1987 | Forester et al. |
| 4,676,246 | A | 6/1987 | Korenaga |
| 4,722,326 | A | 2/1988 | Ruderian |
| 4,728,934 | A | 3/1988 | Pfander et al. |
| 4,837,049 | A | 6/1989 | Byers et al. |
| 4,860,748 | A | 8/1989 | Chiurco et al. |
| 4,885,565 | A | 12/1989 | Embach |
| 4,926,879 | A | 5/1990 | Sevrain et al. |
| 4,930,504 | A | 6/1990 | Diamantopoulos et al. |
| 5,024,236 | A | 6/1991 | Shapiro |
| 5,050,587 | A | 9/1991 | Sagara et al. |
| 5,097,828 | A | 3/1992 | Deutsch |
| 5,103,809 | A | 4/1992 | DeLuca et al. |
| 5,109,844 | A | 5/1992 | De Juan et al. |
| 5,150,704 | A | 9/1992 | Tatebayashi et al. |
| 5,165,897 | A | 11/1992 | Johnson |
| 5,175,459 | A | 12/1992 | Danial et al. |
| 5,215,088 | A | 6/1993 | Normann et al. |
| 5,259,380 | A | 11/1993 | Mendes et al. |
| 5,272,716 | A | 12/1993 | Soltz et al. |
| 5,300,097 | A | 4/1994 | Lerner et al. |
| 5,304,207 | A | 4/1994 | Stromer |
| 5,314,456 | A | 5/1994 | Cohen |
| 5,327,886 | A | 7/1994 | Chiu |
| 5,358,503 | A | 10/1994 | Bertwell et al. |
| 5,385,503 | A | 1/1995 | Stouffer et al. |
| 5,436,622 | A | 7/1995 | Gutman et al. |
| 5,443,915 | A | 8/1995 | Wilkie et al. |
| 5,449,378 | A | 9/1995 | Schouenborg |
| 5,464,436 | A | 11/1995 | Smith |
| 5,549,660 | A | 8/1996 | Mendes et al. |
| 5,551,949 | A | 9/1996 | Kim |
| 5,553,148 | A | 9/1996 | Werle |
| 5,569,307 | A | 10/1996 | Schulman et al. |
| 5,575,761 | A | 11/1996 | Hajianpour |
| 5,578,065 | A | 11/1996 | Hattori et al. |
| 5,601,618 | A | 2/1997 | James |
| 5,616,140 | A | 4/1997 | Prescott |
| 5,627,548 | A | 5/1997 | Woo et al. |
| 5,628,769 | A | 5/1997 | Saringer |
| 5,631,861 | A | 5/1997 | Kramer |
| 5,665,053 | A | 9/1997 | Jacobs |
| 5,709,219 | A | 1/1998 | Chen et al. |
| 5,719,561 | A | 2/1998 | Gonzales |
| 5,776,233 | A | 7/1998 | Wiedemann et al. |
| 5,779,483 | A | 7/1998 | Cho |
| 5,800,479 | A | 9/1998 | Thiberg |
| 5,830,208 | A | 11/1998 | Muller |
| 5,843,074 | A | 12/1998 | Cocilovo |
| 5,865,771 | A | 2/1999 | Shuto et al. |
| 5,876,427 | A | 3/1999 | Chen et al. |
| 5,895,348 | A | 4/1999 | Hosaka |
| 5,913,883 | A | 6/1999 | Alexander et al. |
| 5,935,155 | A | 8/1999 | Humayun et al. |
| 5,944,748 | A | 8/1999 | Mager et al. |
| 5,945,978 | A | 8/1999 | Holmes |

(56) References Cited

U.S. PATENT DOCUMENTS

| | | | |
|---|---|---|---|
| 5,948,006 | A | 9/1999 | Mann |
| 5,957,569 | A | 9/1999 | Helbig et al. |
| 5,957,960 | A | 9/1999 | Chen et al. |
| 6,017,337 | A | 1/2000 | Pira |
| 6,021,348 | A | 2/2000 | James |
| 6,038,485 | A | 3/2000 | Axelgaard |
| 6,045,575 | A | 4/2000 | Rosen et al. |
| 6,063,108 | A | 5/2000 | Salansky et al. |
| 6,074,411 | A | 6/2000 | Lai et al. |
| 6,088,017 | A | 7/2000 | Tremblay et al. |
| 6,096,066 | A | 8/2000 | Chen et al. |
| 6,099,554 | A | 8/2000 | Nordquist et al. |
| 6,104,820 | A | 8/2000 | Soza |
| 6,107,466 | A | 8/2000 | Hasan et al. |
| 6,125,636 | A | 10/2000 | Taylor et al. |
| 6,132,392 | A | 10/2000 | Stone |
| 6,155,995 | A | 12/2000 | Lin |
| 6,156,028 | A | 12/2000 | Prescott |
| 6,228,103 | B1 | 5/2001 | Grey et al. |
| 6,275,213 | B1 | 8/2001 | Tremblay et al. |
| 6,277,085 | B1 | 8/2001 | Flynn |
| 6,362,740 | B1 | 3/2002 | Jung |
| 6,380,923 | B1 | 4/2002 | Fukumoto et al. |
| 6,400,989 | B1 | 6/2002 | Eckmiller |
| 6,402,739 | B1 | 6/2002 | Neev |
| 6,413,230 | B1 | 7/2002 | Haupt et al. |
| 6,458,157 | B1 | 10/2002 | Suaning |
| 6,547,788 | B1 | 4/2003 | Maguire et al. |
| 6,567,696 | B2 | 5/2003 | Voznesensky et al. |
| 6,712,613 | B2 | 3/2004 | Depta |
| 6,735,480 | B2 | 5/2004 | Giuntoli et al. |
| 6,819,312 | B2 | 11/2004 | Fish |
| 6,860,896 | B2 | 3/2005 | Leber et al. |
| 6,889,090 | B2 | 5/2005 | Kreindel |
| 7,013,179 | B2 | 3/2006 | Carter et al. |
| 7,035,422 | B1 | 4/2006 | Wiener |
| 7,077,858 | B2 | 7/2006 | Fletcher et al. |
| 7,081,128 | B2 | 7/2006 | Hart et al. |
| 7,110,820 | B2 | 9/2006 | Tcheng et al. |
| 7,113,177 | B2 | 9/2006 | Franzen |
| 7,182,739 | B2 | 2/2007 | Kopanic et al. |
| 7,238,162 | B2 | 7/2007 | Dehli |
| 7,241,291 | B2 | 7/2007 | Kreindel et al. |
| 7,276,058 | B2 | 10/2007 | Altshuler et al. |
| 7,324,094 | B2 | 1/2008 | Moilanen et al. |
| 7,336,266 | B2 | 2/2008 | Hayward et al. |
| 7,384,405 | B2 | 6/2008 | Rhoades |
| 7,390,157 | B2 | 6/2008 | Kramer |
| 7,615,015 | B2 | 11/2009 | Glen |
| 7,637,878 | B2 | 12/2009 | Lin |
| 7,687,678 | B2 | 3/2010 | Jacobs |
| 7,696,860 | B2 | 4/2010 | Gilson et al. |
| 7,722,655 | B2 | 5/2010 | Lee |
| 7,771,374 | B2 | 8/2010 | Slatkine |
| 7,818,061 | B1 | 10/2010 | Palmer |
| 7,825,903 | B2 | 11/2010 | Anastas et al. |
| 7,871,427 | B2 | 1/2011 | Dunbar et al. |
| 7,927,294 | B2 | 4/2011 | Kamimura et al. |
| 7,988,649 | B1 | 8/2011 | Kost |
| 8,013,847 | B2 | 9/2011 | Anastas |
| 8,027,491 | B2 | 9/2011 | LeDonne |
| 8,139,803 | B2 | 3/2012 | Afshar |
| 8,142,373 | B1 | 3/2012 | Riles |
| 8,147,533 | B2 | 4/2012 | Baxter et al. |
| 8,157,753 | B2 | 4/2012 | Nichols |
| 8,170,656 | B2 | 5/2012 | Tan et al. |
| 8,175,718 | B2 | 5/2012 | Wahlgren et al. |
| 8,203,529 | B2 | 6/2012 | Rogowitz et al. |
| 8,206,327 | B2 | 6/2012 | Wu |
| 8,308,558 | B2 | 11/2012 | Thorner |
| 8,316,166 | B2 | 11/2012 | Grant et al. |
| 8,362,882 | B2 | 1/2013 | Heubel et al. |
| 8,364,257 | B2 | 1/2013 | Eerenbeemd et al. |
| 8,369,944 | B2 | 2/2013 | Macho et al. |
| 8,391,948 | B2 | 3/2013 | Causevic et al. |
| 8,435,194 | B2 | 5/2013 | Dverin et al. |
| 8,468,638 | B2 | 6/2013 | Patel |
| 8,473,045 | B2 | 6/2013 | Terada et al. |
| 8,506,506 | B2 | 8/2013 | Nebrigic et al. |
| 8,552,847 | B1 | 10/2013 | Hill |
| 8,579,953 | B1 | 11/2013 | Dunbar et al. |
| 8,632,576 | B2 | 1/2014 | Quisenberry |
| 8,633,907 | B2 | 1/2014 | Mahalingam |
| 8,686,951 | B2 | 4/2014 | Vartanian et al. |
| 8,696,357 | B2 | 4/2014 | AlDossary |
| 8,702,769 | B2 | 4/2014 | Eckhouse et al. |
| 8,711,118 | B2 | 4/2014 | Short et al. |
| D704,249 | S | 5/2014 | Orzeck |
| 8,740,960 | B2 | 6/2014 | Baxter et al. |
| 8,766,786 | B2 | 7/2014 | Radivojevic |
| 8,767,996 | B1 | 7/2014 | Lin et al. |
| 8,777,881 | B2 | 7/2014 | Tsai |
| 8,906,009 | B2 | 12/2014 | Nebrigic et al. |
| 8,917,167 | B1 | 12/2014 | Selker |
| 8,922,503 | B2 | 12/2014 | Ciesla et al. |
| 8,945,104 | B2 | 2/2015 | Boone, III et al. |
| 8,965,500 | B2 | 2/2015 | Macho et al. |
| 8,979,775 | B2 | 3/2015 | Schafer et al. |
| 9,008,794 | B2 | 4/2015 | Alexandre |
| 9,024,874 | B2 | 5/2015 | Stetten et al. |
| 9,042,971 | B2 | 5/2015 | Brumback et al. |
| 9,046,919 | B2 | 6/2015 | Niknejad |
| 9,050,133 | B1 | 6/2015 | Boone, III et al. |
| 9,053,617 | B2 | 6/2015 | Ramstein et al. |
| 9,064,387 | B2 | 6/2015 | Bhatia et al. |
| 9,078,065 | B2 | 7/2015 | Karam et al. |
| 9,083,821 | B2 | 7/2015 | Hughes |
| 9,092,953 | B1 | 7/2015 | Mortimer et al. |
| 9,092,954 | B2 | 7/2015 | Visitacion et al. |
| 9,095,359 | B2 | 8/2015 | Behnke et al. |
| 9,104,271 | B1 | 8/2015 | Adams et al. |
| 9,170,650 | B2 | 10/2015 | Ramstein et al. |
| 9,195,350 | B2 | 11/2015 | Radivojevic et al. |
| 9,198,792 | B2 | 12/2015 | Skahan et al. |
| 9,213,408 | B2 | 12/2015 | Gandhi et al. |
| 9,245,429 | B2 | 1/2016 | Cruz-Hernandez et al. |
| 9,254,382 | B2 | 2/2016 | Ahmad et al. |
| 9,272,141 | B2 | 3/2016 | Nichols |
| 9,274,603 | B2 | 3/2016 | Modarres et al. |
| 9,282,893 | B2 | 3/2016 | Longinotti-Buitoni et al. |
| 9,295,607 | B2 | 3/2016 | Rosenberg |
| 9,307,756 | B2 | 4/2016 | Clement et al. |
| 9,308,363 | B2 | 4/2016 | Goroszeniuk et al. |
| 9,311,792 | B2 | 4/2016 | Kosonen et al. |
| 9,314,650 | B2 | 4/2016 | Rosenberg et al. |
| 9,333,144 | B2 | 5/2016 | Baxter et al. |
| 9,333,377 | B2 | 5/2016 | Rosenberg |
| 9,364,667 | B1 | 6/2016 | Dinsmoor et al. |
| 9,375,345 | B2 | 6/2016 | Levinson et al. |
| 9,390,630 | B2 | 7/2016 | Daniels |
| 9,407,130 | B2 | 8/2016 | Garcia et al. |
| 9,408,316 | B2 | 8/2016 | Bailey et al. |
| 9,417,694 | B2 | 8/2016 | Birnbaum et al. |
| 9,430,500 | B2 | 8/2016 | Choi et al. |
| 9,452,287 | B2 | 9/2016 | Rosenbluth et al. |
| 9,454,915 | B2 | 9/2016 | Aldossary et al. |
| 9,466,187 | B2 | 10/2016 | Grant et al. |
| 9,468,847 | B2 | 10/2016 | Bekri |
| 9,504,826 | B2 | 11/2016 | Flyash et al. |
| 9,514,620 | B2 | 12/2016 | Bhatia |
| 9,535,502 | B2 | 1/2017 | Hong et al. |
| 9,553,625 | B2 | 1/2017 | Hatanaka et al. |
| 9,561,357 | B2 | 2/2017 | Hall et al. |
| 9,582,034 | B2 | 2/2017 | Badinski et al. |
| 9,582,035 | B2 | 2/2017 | Connor |
| 9,582,072 | B2 | 2/2017 | Connor |
| 9,585,687 | B2 | 3/2017 | Tenenbaum et al. |
| 9,597,217 | B2 | 3/2017 | Patton et al. |
| 9,607,492 | B2 | 3/2017 | Churovich |
| 9,612,661 | B2 | 4/2017 | Wagner et al. |
| 9,619,034 | B2 | 4/2017 | Birnbaum et al. |
| 9,623,907 | B2 | 4/2017 | Marti et al. |
| 9,626,845 | B2 | 4/2017 | Eagleman et al. |
| 9,652,946 | B2 | 5/2017 | Ramstein et al. |

(56) References Cited

U.S. PATENT DOCUMENTS 9,669,233 B2 6/2017 Quisenberry et al.
9,672,701 B2 6/2017 Evreinov et al.
9,672,791 B2 6/2017 Kapinos et al.
9,679,546 B2 6/2017 Ebeling et al.
9,703,381 B2 7/2017 Gallo et al.
9,710,607 B2 7/2017 Ramdas et al.
9,744,096 B2 8/2017 Park et al.
9,754,078 B2 9/2017 Ramsay et al.
9,754,464 B1 9/2017 Sinkov
9,829,977 B2 11/2017 Heubel et al.
9,830,781 B2 11/2017 Mirov et al.
9,848,058 B2 12/2017 Johnson et al.
9,875,340 B2 1/2018 Sharma
9,884,164 B2 2/2018 Tass
9,884,179 B2 2/2018 Bouton et al.
9,886,093 B2 2/2018 Moussette et al.
9,898,085 B2 2/2018 Saboune et al.
9,907,692 B2 3/2018 Binversie et al.
9,936,900 B2 4/2018 Chang et al.
9,940,811 B2 4/2018 Chang et al.
9,943,698 B2 4/2018 Chase et al.
9,950,147 B2 4/2018 Mehta
9,961,435 B1 5/2018 Goyal et al.
10,016,615 B2 7/2018 Simon et al.
10,019,912 B2 7/2018 Eagleman et al.
10,039,928 B2 8/2018 Hyde et al.
10,058,476 B2 8/2018 Baxter et al.
10,070,799 B2 9/2018 Ang et al.
10,071,015 B2 9/2018 Seo et al.
10,080,892 B2 9/2018 Southwell et al.
10,080,906 B2 9/2018 Schwarz et al.
10,101,810 B2 10/2018 Li et al.
10,111,010 B2 10/2018 Alexiou et al.
10,123,937 B2 11/2018 Pisharodi et al.
D837,395 S 1/2019 Gan
10,181,331 B2 1/2019 Eagleman et al.
10,182,964 B2 1/2019 Snow
10,191,537 B2 1/2019 Tanaka et al.
10,198,076 B2 2/2019 Eagleman et al.
10,200,332 B2 2/2019 Wu et al.
10,204,494 B2 2/2019 Do et al.
10,216,278 B2 2/2019 Nakamura et al.
10,231,664 B2 3/2019 Ganesh
10,234,934 B2 3/2019 Connor
10,248,208 B2 4/2019 Kim et al.
10,255,771 B2 4/2019 Baron et al.
10,275,029 B2 4/2019 Jones et al.
10,285,902 B2 5/2019 Pamplin et al.
10,321,873 B2 6/2019 Connor
10,371,544 B2 8/2019 Yoo et al.
10,384,076 B2 8/2019 Wagenaar et al.
10,437,340 B1 10/2019 Sullivan
10,456,604 B2 10/2019 Cheatham, III et al.
10,512,431 B2 12/2019 Cheng et al.
10,512,770 B2 12/2019 Wingeier et al.
10,524,978 B2 1/2020 Marton et al.
10,532,181 B2 1/2020 Hooper et al.
10,533,780 B2 1/2020 Yi et al.
10,555,681 B2 2/2020 Sun
10,589,056 B2 3/2020 Woo
10,589,087 B2 3/2020 Tyler et al.
10,613,630 B2 4/2020 Omote
10,621,837 B2 4/2020 Tachi et al.
10,625,074 B2 4/2020 Rosenbluth et al.
10,632,040 B2 4/2020 Muench et al.
10,632,279 B2 4/2020 Akimoto et al.
10,699,538 B2 6/2020 Novich et al.
10,713,907 B2 7/2020 Anderson et al.
10,732,717 B2 8/2020 Sato et al.
10,735,831 B2 8/2020 Dixit
10,748,448 B2 8/2020 Knott et al.
D895,830 S 9/2020 Nakamura
10,758,405 B2 9/2020 Deng et al.
10,772,394 B1 9/2020 Michalske
10,786,666 B2 9/2020 Chu et al.
10,799,697 B2 10/2020 Kim et al.
10,806,053 B1 10/2020 Toleno et al.
10,821,297 B2 11/2020 Binner et al.
10,881,849 B2 1/2021 Pisarev et al.
10,888,708 B2 1/2021 Stephens et al.
10,905,628 B2 2/2021 Hodges, IV
10,912,712 B2 2/2021 Tracey et al.
10,918,561 B2 2/2021 Wyatt et al.
10,918,859 B2 2/2021 Kang
10,925,803 B2 2/2021 Lattner
10,945,878 B2 3/2021 Deng et al.
10,945,915 B2 3/2021 Wersland et al.
10,964,179 B2 3/2021 Ebeling et al.
10,993,872 B2 5/2021 Novich et al.
11,031,117 B2 6/2021 Mayo et al.
11,033,708 B2 6/2021 Blahnik et al.
11,065,174 B2 7/2021 Lach et al.
11,079,851 B2 8/2021 Eagleman et al.
11,224,895 B2 1/2022 Brown et al.
11,247,039 B2 2/2022 Prouza et al.
11,253,717 B2 2/2022 Schwarz et al.
11,260,198 B2 3/2022 Rabin et al.
11,273,304 B2 3/2022 Wingeier et al.
11,275,441 B2 3/2022 Fainstain
11,285,291 B2 3/2022 Prattichizzo et al.
11,287,890 B2 3/2022 Yi et al.
11,311,232 B2 4/2022 Arrington et al.
11,363,980 B2 6/2022 Dauguet et al.
11,432,994 B2 9/2022 Wersland et al.
11,439,841 B2 9/2022 Zimmerman
11,464,993 B2 10/2022 Schwarz et al.
11,474,359 B2 10/2022 Samec et al.
11,478,606 B1 10/2022 English et al.
11,491,081 B2 11/2022 Akaikine et al.
11,504,497 B2 11/2022 Jin et al.
11,534,571 B2 12/2022 Rabin et al.
11,564,860 B2 1/2023 Wersland et al.
11,590,313 B2 2/2023 Lee
11,600,155 B2 3/2023 Gioioso et al.
11,622,909 B2 4/2023 Wersland et al.
11,625,994 B2 4/2023 Ebeling et al.
11,660,442 B2 5/2023 Siegle et al.
11,684,510 B2 6/2023 Nofzinger
11,693,481 B2 7/2023 Ollier et al.
11,701,253 B2 7/2023 Black et al.
11,712,367 B2 8/2023 Simons et al.
11,896,545 B2 2/2024 Merino et al.
11,975,359 B2 5/2024 Xu et al.
12,005,021 B2 6/2024 Smith et al.
12,008,892 B2 6/2024 Ebeling et al.
12,061,740 B2 8/2024 Niijima et al.
12,076,496 B2 9/2024 Hanbury
12,193,988 B2 1/2025 Tass et al.
12,201,448 B2 1/2025 Dar et al.
12,210,686 B2 1/2025 Gwak
12,230,124 B2 2/2025 Suzuki et al.
12,245,979 B2 3/2025 Mayo et al.
12,290,488 B2 5/2025 Blanche
12,290,640 B2 5/2025 Nofzinger et al.
12,311,116 B2 5/2025 English
12,387,577 B2 8/2025 Ebeling et al.
12,403,034 B2 9/2025 Liang et al.
12,453,853 B2 10/2025 Rosenbluth et al.
2001/0007952 A1 7/2001 Shimizu
2001/0043847 A1 11/2001 Kramer
2002/0143373 A1 10/2002 Courtnage et al.
2003/0023297 A1 1/2003 Byers et al.
2003/0032900 A1 2/2003 Ella
2003/0083599 A1 5/2003 Kitov
2003/0153961 A1 8/2003 Babaev
2003/0181116 A1 9/2003 Heerden et al.
2003/0187488 A1 10/2003 Kreindel et al.
2003/0212350 A1 11/2003 Tadlock
2004/0039254 A1 2/2004 Stivoric et al.
2004/0040800 A1 3/2004 Anastas et al.
2004/0082886 A1 4/2004 Timpson
2004/0171970 A1 9/2004 Schleuniger et al.
2004/0193078 A1 9/2004 Flick et al.
2004/0210122 A1 10/2004 Sieburg

(56) References Cited

U.S. PATENT DOCUMENTS

2004/0241623 A1 12/2004 Lenay et al.
2004/0260211 A1 12/2004 Maalouf
2005/0078846 A1 4/2005 Single
2005/0177093 A1 8/2005 Barry et al.
2005/0209537 A1 9/2005 Gleason et al.
2006/0036201 A1 2/2006 Cohen
2006/0041207 A1 2/2006 Gross
2006/0047342 A1 3/2006 Khoshnevis
2006/0052695 A1 3/2006 Adam
2006/0116611 A1 6/2006 Richter
2006/0135890 A1 6/2006 Tsai
2006/0247754 A1 11/2006 Greenberg et al.
2006/0253051 A1 11/2006 Milne et al.
2006/0258930 A1 11/2006 Wu et al.
2006/0264926 A1 11/2006 Kochamba
2007/0010810 A1 1/2007 Kochamba
2007/0016425 A1 1/2007 Ward
2007/0027411 A1 2/2007 Ella et al.
2007/0063849 A1 3/2007 Rosella et al.
2007/0103430 A1 5/2007 Nishi
2007/0255187 A1 11/2007 Branch
2007/0255355 A1 11/2007 Altshuler et al.
2007/0282400 A1 12/2007 Gorham
2007/0293762 A1 12/2007 Sawada et al.
2008/0014011 A1 1/2008 Rossen
2008/0023597 A1 1/2008 Wyner et al.
2008/0027363 A1 1/2008 Brueckmann et al.
2008/0168775 A1 7/2008 Windheim et al.
2008/0188911 A1 8/2008 Chao
2008/0195000 A1 8/2008 Spooner et al.
2008/0215039 A1 9/2008 Slatkine et al.
2008/0312647 A1 12/2008 Knopp et al.
2009/0005713 A1 1/2009 Podrazhansky et al.
2009/0048547 A1 2/2009 Chen
2009/0076421 A1 3/2009 Grant, Jr.
2009/0096746 A1 4/2009 Kruse et al.
2009/0098519 A1 4/2009 Byerly
2009/0112134 A1 4/2009 Avni
2009/0120105 A1 5/2009 Ramsay et al.
2009/0131840 A1 5/2009 Lee
2009/0143516 A1 6/2009 MacDonald et al.
2009/0143706 A1 6/2009 Acosta
2009/0156958 A1 6/2009 Mehta et al.
2009/0171251 A1 7/2009 Rybyanets et al.
2009/0180646 A1 7/2009 Vulfson et al.
2009/0216070 A1 8/2009 Hunt et al.
2009/0221938 A1 9/2009 Rosenberg et al.
2010/0004536 A1 1/2010 Rosenberg
2010/0016761 A1 1/2010 Rosenberg
2010/0042020 A1 2/2010 Ben-Ezra
2010/0069800 A1 3/2010 Hsu
2010/0073150 A1 3/2010 Olson et al.
2010/0134327 A1 6/2010 Dinh et al.
2010/0137752 A1 6/2010 Heine et al.
2010/0141407 A1 6/2010 Heubel et al.
2010/0145242 A1 6/2010 Tsai
2010/0145425 A1 6/2010 Jung et al.
2010/0162109 A1 6/2010 Chatterjee et al.
2010/0204619 A1 8/2010 Rosenberg
2010/0204694 A1 8/2010 Mehta et al.
2010/0259472 A1 10/2010 Radivojevic et al.
2010/0280582 A1 11/2010 Baker et al.
2010/0292746 A1 11/2010 Gorham
2010/0298745 A1 11/2010 Liu et al.
2010/0304864 A1 12/2010 Johnson et al.
2010/0305495 A1 12/2010 Anderson et al.
2011/0004261 A1 1/2011 Sham et al.
2011/0040204 A1 2/2011 Ivorra et al.
2011/0040235 A1 2/2011 Castel
2011/0046523 A1 2/2011 Altshuler et al.
2011/0112405 A1 5/2011 Barthe et al.
2011/0148607 A1 6/2011 Zeleny
2011/0166559 A1 7/2011 Eckhouse et al.
2011/0251532 A1 10/2011 Yang
2011/0270140 A1 11/2011 Israeli
2011/0319796 A1 12/2011 Campdera Lozano
2012/0010603 A1 1/2012 Milner et al.
2012/0022411 A1 1/2012 Wu
2012/0023785 A1 2/2012 Barnes et al.
2012/0035513 A1 2/2012 Afshar
2012/0070805 A1 3/2012 Wong et al.
2012/0123304 A1 5/2012 Rybyanets
2012/0165710 A1 6/2012 Nichols
2012/0232780 A1 9/2012 Delson et al.
2012/0253236 A1 10/2012 Snow et al.
2012/0253245 A1 10/2012 Stanbridge
2012/0253416 A1 10/2012 Erez et al.
2012/0277587 A1 11/2012 Adanny et al.
2012/0283605 A1 11/2012 Lewis, Jr.
2012/0316381 A1 12/2012 Teggatz et al.
2013/0041296 A1 2/2013 Tass et al.
2013/0046212 A1 2/2013 Nichols
2013/0073017 A1 3/2013 Liu et al.
2013/0085421 A1 4/2013 Gillespie et al.
2013/0123570 A1 5/2013 Ly et al.
2013/0131559 A1 5/2013 Vandenbelt et al.
2013/0178764 A1 7/2013 Eckhouse et al.
2013/0184693 A1 7/2013 Neev
2013/0202674 A1 8/2013 Ericson
2013/0204169 A1 8/2013 Poepperling et al.
2013/0218197 A1 8/2013 Tarumi
2013/0218456 A1 8/2013 Zelek et al.
2013/0331913 A1 12/2013 Levi et al.
2014/0007957 A1 1/2014 Vendramini
2014/0036053 A1 2/2014 Clingman et al.
2014/0070957 A1 3/2014 Longinotti-Buitoni et al.
2014/0085077 A1 3/2014 Luna et al.
2014/0107542 A1 4/2014 Schubert et al.
2014/0128780 A1 5/2014 Kennedy et al.
2014/0143737 A1 5/2014 Mistry et al.
2014/0163439 A1 6/2014 Uryash et al.
2014/0172062 A1 6/2014 Yoon
2014/0180181 A1 6/2014 Oepen et al.
2014/0184384 A1 7/2014 Zhu et al.
2014/0198034 A1 7/2014 Bailey et al.
2014/0198035 A1 7/2014 Bailey et al.
2014/0206947 A1 7/2014 Isserow et al.
2014/0206976 A1 7/2014 Thompson et al.
2014/0209594 A1 7/2014 Besner
2014/0214206 A1 7/2014 Steinberg et al.
2014/0215684 A1 8/2014 Hardy et al.
2014/0221879 A1 8/2014 Chu
2014/0266570 A1 9/2014 Sharma et al.
2014/0266571 A1 9/2014 Sharma et al.
2014/0276270 A1 9/2014 Ludlow et al.
2014/0276271 A1 9/2014 Stryker et al.
2014/0326241 A1 11/2014 Martin et al.
2014/0378555 A1 12/2014 Hung et al.
2015/0019135 A1 1/2015 Kacyvenski et al.
2015/0038886 A1 2/2015 Snow
2015/0045702 A1 2/2015 Lin
2015/0105129 A1 4/2015 Chapman
2015/0119771 A1 4/2015 Roberts
2015/0182762 A1 7/2015 Schafer et al.
2015/0190607 A1 7/2015 Sugio et al.
2015/0201181 A1 7/2015 Moore et al.
2015/0217142 A1 8/2015 Schafer
2015/0220199 A1 8/2015 Wang et al.
2015/0235529 A1 8/2015 Deschamps
2015/0257970 A1 9/2015 Mücke et al.
2015/0265214 A1 9/2015 De Kok et al.
2015/0283022 A1 10/2015 Lee et al.
2015/0283026 A1 10/2015 Rosenberg
2015/0283277 A1 10/2015 Schafer et al.
2015/0290454 A1 10/2015 Tyler et al.
2015/0297445 A1 10/2015 Gordon et al.
2015/0305969 A1 10/2015 Giraud et al.
2015/0306373 A1 10/2015 Bouton et al.
2015/0321000 A1 11/2015 Rosenbluth et al.
2015/0328474 A1 11/2015 Flyash et al.
2015/0335288 A1 11/2015 Toth et al.
2015/0339899 A1 11/2015 Ozaki et al.
2015/0351690 A1 12/2015 Toth et al.
2015/0364018 A1 12/2015 Mirov et al.

(56) References Cited

U.S. PATENT DOCUMENTS

| | | | |
|---|---|---|---|
| 2015/0366504 | A1 | 12/2015 | Connor |
| 2015/0379880 | A1 | 12/2015 | Sethi |
| 2016/0012688 | A1 | 1/2016 | Eagleman et al. |
| 2016/0012689 | A1 | 1/2016 | Evreinov et al. |
| 2016/0018920 | A1 | 1/2016 | Deokar et al. |
| 2016/0034742 | A1 | 2/2016 | Kim et al. |
| 2016/0058156 | A1 | 3/2016 | Chiasson |
| 2016/0095789 | A1 | 4/2016 | Baxter et al. |
| 2016/0101010 | A1 | 4/2016 | Hsu |
| 2016/0118566 | A1 | 4/2016 | Lee et al. |
| 2016/0129248 | A1 | 5/2016 | Creasey et al. |
| 2016/0136040 | A1 | 5/2016 | Li |
| 2016/0138144 | A1 | 5/2016 | Olsérius et al. |
| 2016/0165965 | A1 | 6/2016 | Ellis et al. |
| 2016/0187977 | A1 | 6/2016 | Cruz-Hernandez et al. |
| 2016/0195928 | A1 | 7/2016 | Wagner et al. |
| 2016/0235980 | A1 | 8/2016 | Berman et al. |
| 2016/0235983 | A1 | 8/2016 | Berman et al. |
| 2016/0246378 | A1 | 8/2016 | Sampanes et al. |
| 2016/0255733 | A1 | 9/2016 | Jung et al. |
| 2016/0267344 | A1 | 9/2016 | Yamamoto |
| 2016/0302721 | A1 | 10/2016 | Wiedenhoefer et al. |
| 2016/0310353 | A1* | 10/2016 | Barasch ................. A61H 19/00 |
| 2016/0338644 | A1 | 11/2016 | Connor |
| 2016/0346153 | A1 | 12/2016 | Hodges et al. |
| 2016/0346162 | A1 | 12/2016 | Powers |
| 2016/0349790 | A1 | 12/2016 | Connor |
| 2016/0360974 | A1 | 12/2016 | Lange |
| 2016/0374886 | A1 | 12/2016 | Wyatt et al. |
| 2017/0004685 | A1 | 1/2017 | Karsten |
| 2017/0011602 | A1 | 1/2017 | Brav et al. |
| 2017/0036002 | A1 | 2/2017 | Ignon et al. |
| 2017/0043150 | A1 | 2/2017 | Kim |
| 2017/0049611 | A1 | 2/2017 | Rosh Vora et al. |
| 2017/0080255 | A1 | 3/2017 | Law et al. |
| 2017/0095692 | A1 | 4/2017 | Chang et al. |
| 2017/0095693 | A1 | 4/2017 | Chang et al. |
| 2017/0098350 | A1 | 4/2017 | Ebeling et al. |
| 2017/0156662 | A1 | 6/2017 | Goodall et al. |
| 2017/0165486 | A1 | 6/2017 | Harry et al. |
| 2017/0165567 | A1 | 6/2017 | Walters |
| 2017/0188894 | A1 | 7/2017 | Chang et al. |
| 2017/0189227 | A1 | 7/2017 | Brunson et al. |
| 2017/0209708 | A1 | 7/2017 | Schwarz |
| 2017/0221323 | A1 | 8/2017 | Nakamura et al. |
| 2017/0246076 | A1 | 8/2017 | Miller et al. |
| 2017/0249810 | A1 | 8/2017 | Zerick et al. |
| 2017/0252534 | A1 | 9/2017 | Nofzinger |
| 2017/0273601 | A1 | 9/2017 | Wang et al. |
| 2017/0290732 | A1 | 10/2017 | Palomäki et al. |
| 2017/0291007 | A1 | 10/2017 | Dubey et al. |
| 2017/0296429 | A1 | 10/2017 | Mayo et al. |
| 2017/0304145 | A1 | 10/2017 | Pepe |
| 2017/0304646 | A1 | 10/2017 | Pryor et al. |
| 2017/0308165 | A1 | 10/2017 | Erivantcev et al. |
| 2017/0348049 | A1 | 12/2017 | Vrba et al. |
| 2017/0367654 | A1 | 12/2017 | Cheng et al. |
| 2018/0015299 | A1 | 1/2018 | Kawa |
| 2018/0021579 | A1 | 1/2018 | Kahana et al. |
| 2018/0078206 | A1 | 3/2018 | Aimone et al. |
| 2018/0081439 | A1 | 3/2018 | Daniels |
| 2018/0099143 | A1 | 4/2018 | Kim et al. |
| 2018/0140503 | A1 | 5/2018 | Kim et al. |
| 2018/0168915 | A1 | 6/2018 | Gwen |
| 2018/0207056 | A1 | 7/2018 | Howard et al. |
| 2018/0243161 | A1 | 8/2018 | Lenke |
| 2018/0280227 | A1 | 10/2018 | Quest et al. |
| 2018/0296166 | A1 | 10/2018 | LeBoeuf et al. |
| 2018/0296834 | A1 | 10/2018 | John et al. |
| 2018/0303702 | A1 | 10/2018 | Novich et al. |
| 2018/0307314 | A1 | 10/2018 | Connor |
| 2018/0318545 | A1 | 11/2018 | Jones et al. |
| 2019/0029878 | A1 | 1/2019 | Linder et al. |
| 2019/0064924 | A1 | 2/2019 | Nocon |
| 2019/0076643 | A1 | 3/2019 | Siegle et al. |
| 2019/0104953 | A1 | 4/2019 | Narasimhan |
| 2019/0105101 | A1 | 4/2019 | Narisawa |
| 2019/0110949 | A1 | 4/2019 | Bhatti |
| 2019/0125262 | A1 | 5/2019 | Markel |
| 2019/0151604 | A1 | 5/2019 | Harper et al. |
| 2019/0183388 | A1 | 6/2019 | Cohen et al. |
| 2019/0188976 | A1 | 6/2019 | Aleksov et al. |
| 2019/0278374 | A1 | 9/2019 | Sato et al. |
| 2019/0343205 | A1 | 11/2019 | Clausen |
| 2019/0350752 | A1 | 11/2019 | Aguiar et al. |
| 2019/0391648 | A1 | 12/2019 | Park et al. |
| 2020/0061377 | A1 | 2/2020 | Siegle et al. |
| 2020/0163572 | A1 | 5/2020 | Mann |
| 2020/0170534 | A1 | 6/2020 | Flaeschner et al. |
| 2020/0174583 | A1 | 6/2020 | Wang |
| 2020/0186104 | A1 | 6/2020 | Honda et al. |
| 2020/0222695 | A1 | 7/2020 | Simon et al. |
| 2020/0245931 | A1 | 8/2020 | Chmelik |
| 2020/0246520 | A1 | 8/2020 | Chang |
| 2020/0253485 | A1 | 8/2020 | Kang et al. |
| 2020/0324104 | A1 | 10/2020 | Labuschagne et al. |
| 2020/0356169 | A1 | 11/2020 | Belomoev |
| 2021/0052869 | A1 | 2/2021 | Chabal et al. |
| 2021/0186801 | A1 | 6/2021 | Thomas et al. |
| 2021/0244316 | A1 | 8/2021 | Khaled |
| 2021/0286180 | A1 | 9/2021 | Samec et al. |
| 2021/0290482 | A1 | 9/2021 | Wang et al. |
| 2021/0401664 | A1 | 12/2021 | Tass |
| 2022/0171464 | A1 | 6/2022 | Ollier et al. |
| 2022/0233123 | A1 | 7/2022 | Telfer et al. |
| 2022/0233860 | A1 | 7/2022 | Hamner et al. |
| 2022/0296894 | A1 | 9/2022 | Jung |
| 2022/0347010 | A1 | 11/2022 | Kerth et al. |
| 2023/0031613 | A1 | 2/2023 | Fleury et al. |
| 2023/0050278 | A1 | 2/2023 | Mcdaniel et al. |
| 2023/0053027 | A1 | 2/2023 | Yu et al. |
| 2023/0122309 | A1 | 4/2023 | Zhu et al. |
| 2023/0185376 | A1 | 6/2023 | Sembaluk et al. |

FOREIGN PATENT DOCUMENTS

| | | | |
|---|---|---|---|
| CN | 2097631 | U | 3/1992 |
| CN | 2348818 | Y | 11/1999 |
| CN | 1411793 | A | 4/2003 |
| CN | 2936240 | Y | 8/2007 |
| CN | 200970326 | Y | 11/2007 |
| CN | 101146496 | A | 3/2008 |
| CN | 201304136 | Y | 9/2009 |
| CN | 202637439 | U | 1/2013 |
| CN | 103239340 | A | 8/2013 |
| CN | 103284874 | A | 9/2013 |
| CN | 103550029 | A | 2/2014 |
| CN | 204033719 | U | 12/2014 |
| CN | 104368051 | A | 2/2015 |
| CN | 204562826 | U | 8/2015 |
| CN | 105726286 | A | 7/2016 |
| CN | 105769505 | A | 7/2016 |
| CN | 205698460 | U | 11/2016 |
| CN | 106511045 | A | 3/2017 |
| CN | 206026664 | U | 3/2017 |
| CN | 206434557 | U | 8/2017 |
| CN | 107320798 | A | 11/2017 |
| CN | 206660195 | U | 11/2017 |
| CN | 107811833 | A | 3/2018 |
| CN | 207679875 | U | 8/2018 |
| CN | 108938359 | A | 12/2018 |
| CN | 209347585 | U | 9/2019 |
| CN | 210228475 | U | 4/2020 |
| CN | 112470104 | B | 3/2021 |
| EP | 0528746 | A1 | 2/1993 |
| EP | 0556999 | A1 | 5/1998 |
| EP | 2203797 | A1 | 7/2010 |
| EP | 2450075 | A1 | 5/2012 |
| EP | 2506773 | A1 | 10/2012 |
| EP | 2203797 | B1 | 7/2014 |
| EP | 2790088 | A | 10/2014 |
| EP | 3003473 | A1 | 4/2016 |
| EP | 2506773 | B1 | 8/2018 |
| EP | 3003473 | B1 | 8/2018 |

(56) References Cited

FOREIGN PATENT DOCUMENTS

| | | | |
|---|---|---|---|
| EP | 2790088 | B1 | 5/2019 |
| EP | 3663894 | A4 | 6/2020 |
| EP | 3768217 | B1 | 1/2021 |
| GB | 2395027 | A | 5/2004 |
| JP | S6048741 | A | 3/1985 |
| JP | H059543 | U | 2/1993 |
| JP | 2000244991 | A | 9/2000 |
| JP | 4143114 | B2 | 6/2008 |
| JP | 4403474 | B | 1/2010 |
| JP | 4744968 | B2 | 8/2011 |
| JP | 5129032 | B | 1/2013 |
| JP | 2013091114 | A | 5/2013 |
| JP | 2017035414 | A | 2/2017 |
| JP | 6178566 | B2 | 8/2017 |
| JP | 6269171 | B | 1/2018 |
| JP | 2018010582 | A | 1/2018 |
| JP | 6652164 | B2 | 2/2020 |
| JP | 2020057030 | A | 4/2020 |
| JP | 2022050711 | A | 3/2022 |
| JP | 7133785 | B | 9/2022 |
| KR | 930001844 | A | 2/1993 |
| KR | 1019930010698 | B1 | 11/1993 |
| KR | 100235532 | B1 | 12/1999 |
| KR | 20010008111 | A | 2/2001 |
| KR | 20040042912 | A | 5/2004 |
| KR | 200359335 | Y1 | 8/2004 |
| KR | 200395260 | Y1 | 9/2005 |
| KR | 200412070 | Y1 | 3/2006 |
| KR | 1020070037576 | A | 4/2007 |
| KR | 100746214 | B1 | 8/2007 |
| KR | 100787874 | B1 | 12/2007 |
| KR | 100793861 | B1 | 1/2008 |
| KR | 100867408 | B1 | 11/2008 |
| KR | 200453862 | Y1 | 5/2011 |
| KR | 101064115 | B1 | 9/2011 |
| KR | 20110119468 | A | 11/2011 |
| KR | 20120018245 | A | 3/2012 |
| KR | 101123926 | B1 | 4/2012 |
| KR | 20120128427 | A | 11/2012 |
| KR | 20130043299 | A | 4/2013 |
| KR | 101301006 | B1 | 8/2013 |
| KR | 101315403 | B1 | 10/2013 |
| KR | 101319429 | B1 | 10/2013 |
| KR | 20130109422 | A | 10/2013 |
| KR | 101367893 | B1 | 2/2014 |
| KR | 101515410 | B1 | 4/2015 |
| KR | 101658513 | B1 | 9/2016 |
| KR | 101767485 | B1 | 8/2017 |
| KR | 20170108550 | A | 9/2017 |
| KR | 101810511 | B1 | 12/2017 |
| KR | 101827139 | B1 | 2/2018 |
| KR | 20180116653 | A | 10/2018 |
| KR | 101951917 | B1 | 4/2019 |
| KR | 20210126424 | A | 10/2021 |
| SG | 181413 | | 7/2012 |
| WO | 0240095 | A1 | 5/2002 |
| WO | 2004023235 | A2 | 3/2004 |
| WO | 2012074483 | A1 | 6/2012 |
| WO | 2013009814 | A2 | 1/2013 |
| WO | 2013118122 | A1 | 8/2013 |
| WO | 2014117125 | A1 | 7/2014 |
| WO | 2014194200 | A1 | 12/2014 |
| WO | 2015083183 | A1 | 6/2015 |
| WO | 2015127070 | A1 | 8/2015 |
| WO | 2016019250 | A1 | 2/2016 |
| WO | 2016050620 | A1 | 4/2016 |
| WO | 2016201366 | A1 | 12/2016 |
| WO | 2017029406 | A1 | 2/2017 |
| WO | 2017137930 | A1 | 8/2017 |
| WO | 2017158583 | A1 | 9/2017 |
| WO | 2017173436 | A1 | 10/2017 |
| WO | 2017175868 | A1 | 10/2017 |
| WO | 2018013835 | A1 | 1/2018 |
| WO | 2018013835 | A4 | 1/2018 |
| WO | 2018048907 | A1 | 3/2018 |
| WO | 2018143418 | A1 | 8/2018 |
| WO | 2019180677 | A1 | 9/2019 |
| WO | 2020146226 | A1 | 7/2020 |
| WO | 2020219350 | A1 | 10/2020 |
| WO | 2020222821 | A1 | 11/2020 |
| WO | 2021112922 | A1 | 6/2021 |

OTHER PUBLICATIONS

Precision MicroDrives, "6mm Linear Actuator—12 mm type". Website: https://www.precisionmicrodrives.com/product/c12-003-001-6mm-linear-resonant-actuator-12mm-type. Last accessed May 5, 2021.

Precision MicroDrives. Product Data Sheet, 6mm Linear Resonant Actuator Model No. C12-003.001. 2020.

Ashley Carman, "This ring will vibrate in coordination with your loved one's pulse; They're alive! And not answering your texts!," Circuit Breaker, The Verge, Aug. 10, 2016, https://www.theverge.com/circuitbreaker/2016/8/10/12423956/thetouch-hb-ring-heartrate-pulse.

David Eagleman, "Can we create new senses for humans?," Transcript of TED Talk, available at: https://www.ted.com/talks/david_eagleman_can_we_create_new_senses_for_humans/transcript?language=en (last accessed May 17, 2022).

International Preliminary Report on Patentability for International Patent Application No. PCT/US18/56814, dated Apr. 1, 2020 (50 pages).

International Search Report and Written Opinion for International Patent Application No. PCT/US18/56814, mailed Feb. 22, 2019 (21 pages).

Iwamoto et al., "Non-contact Method for Producing Tactile Sensation Using Airborne Ultrasound", Eurohaptics 2008, LNCS 5024, pp. 504-513, http://www.researchgate.net/publication/221011909_Non-contact_Method_for_Producing_Tactile_Sensation_Using_Airborne_Ultrasound.

Maereg et al., "Wearable Vibrotactile Haptic Device for Stiffness Discrimination during Virtual Interactions," Journal of Frontiers in Robotics and AI, vol. 4, 2017, https://www.frontiersin.org/article/10.3389/frobt.2017.00042.

Novich et al., "Using space and time to encode vibrotactile information: toward an estimate of the skin's achievable throughput," Experimental Brain Research. 233, p. 2777-2788(2015). available at: Http://link.springer.com/article/10.1007/s00221-015-4346-1.

Seneviratne et al., "A Survey of Wearable Devices and Challenges," Article, IEEE Communications Surveys & tutorials, Jul. 2017, (52 pages), (99)1-1, available at: http://www.researchgate.net/publications/318717275_A_Survey_of_Wearable_Devices_and_Challenges.

Shull et al., "Haptic wearables as sensory replacement, sensory augmentation andtrainer—a review," Journal of NeuroEngineering and Rehabilitation, vol. 12, Article #59, 2015, https://doi.org/10.1186/s12984-015-0055-z.

Singhal, Anshul et al., Perceptual Interactions in thermo-tactile displays, Jun. 2017, 5 pages, 2017 Institute of Electrical and Electronics Engineers (IEEE) World Haptics Conference, Munich, Germany, Jun. 6-9, 2017.

Supplemental European Search Report for European Patent App. No. EP18871368.9 (European national stage entry of PCT/US18/56814), mailed on Sep. 10, 2021 (2 pages).

Hussain, I., et al., "A wearable haptic ring for the control of extra robotic Cngers," Haptic Interaction; 323-325, Springer Nature Singapore, Netherlands (Jul. 2017).

Meli, L., et al., "The hBracelet: A Wearable Haptic Device for the Distributed Mechanotactile Stimulation of the Upper Limb," IEEE Robotics and AutomationLetters 3(3):2198-2205, Institute of Electrical and Electronics Engineers, United States (Jul. 2018).

* cited by examiner

COMMUNICATION DEVICES, METHODS, AND SYSTEMS

CROSS-REFERENCE TO RELATED APPLICATIONS

This application is a § 1.53(b) of pending prior U.S. patent application Ser. No. 18/626,317, filed Apr. 3, 2024, now U.S. Pat. No. 12,097,161, which is a continuation of U.S. patent application Ser. No. 18/526,980, filed Dec. 1, 2023, now U.S. Pat. No. 12,036,174 which is a continuation of U.S. patent application Ser. No. 18/388,489, filed Nov. 9, 2023, now U.S. Pat. No. 11,931,174, which is a continuation of U.S. patent application Ser. No. 18/143,142, filed May 4, 2023, now U.S. Pat. No. 11,864,914, which is a continuation of U.S. patent application Ser. No. 18/092,398, filed Jan. 2, 2023, now U.S. Pat. No. 11,684,313, which is a continuation of U.S. patent application Ser. No. 17/213,117, filed Mar. 25, 2021, now U.S. Pat. No. 11,589,816, which is a continuation of U.S. patent application Ser. No. 16/757,482, filed Apr. 20, 2020, now U.S. Pat. No. 10,959,674, which is a § 371 National Stage Entry of International Patent Application No. PCT/US18/56814, filed Oct. 22, 2018, claiming the benefit of priority of U.S. Provisional Patent Application No. 62/676,949, filed May 26, 2018, and U.S. Provisional Patent Application No. 62/575,951, filed Oct. 23, 2017, the entireties of which are incorporated by reference into the enclosed application.

TECHNICAL FIELD

Aspects of the present disclosure generally relate to communication devices, methods, and systems.

BACKGROUND

Computer screens have emerged as the most common means for person-to-computer communication. In 2015, for example, it was estimated that the average adult spends roughly 10 hours a day looking at a screen to consume information and/or communicate with others. The human eye was not designed for all this screen time, and numerous health problems have been associated therewith. For example, eyestrain from hours of screen time may cause instances of eye irritation, dryness, fatigue, and/or blurred vision that last for extended periods of time. These problems are increasingly common, and the near constant production of new screen-oriented devices (e.g., the next iPhone®) suggests further increases.

Alternate means for person-to-computer communications may reduce the negative effects of excessive screen time. For example, the human body includes many non-optical nerves that are capable of communicating data to the brain, such as the nerves associated with the skin. Further improvements are required to better leverage these and other communication capabilities of living tissue. Aspects of this disclosure may solve the above reference problems, solve other known problems, and/or overcome other deficiencies in the prior art.

SUMMARY

Numerous aspects are disclosed in this application. One exemplary aspect is a communication device comprising: a body comprising a distal surface compatible with skin; a tissue interface on the distal surface, the tissue interface comprising a plurality of energy generators, each energy generator being operable to output a plurality of energies in a signal direction toward the skin; an attachment element configured to maintain the tissue interface against the skin; and a processing unit configured to communicate with nerves associated with the skin by receiving input data from a data source and causing the plurality of energy generators to output an energy signal in the signal direction with one or more energies of the plurality of energies.

The body may be flexible. The body may comprise a plurality of communication bays, and each energy generator may be located in and configured to output the energy signal out of one of the communication bays. The body may comprise an insulating material configured to promote flows of the one or more energies out of each communication bay in the signal direction, and limit flows of the one or more energies between the plurality of communication bays. The attachment element may comprise a plurality of holes aligned with the plurality of communication bays, and each energy generator may be configured to output the plurality of energies through one of the holes. An interior surface of each communication bay or hole may be configured to direct the one or more energies in the signal direction. The interior surface of each communication bay or hole may be configured to focus at least one energy of the one or more energies in the signal direction.

The attachment element may comprise a biocompatible adhesive disposed on the distal surface of the body. The attachment element may comprise an elastic portion configured to maintain the tissue interface against the skin. The elastic portion may expand to receive a circular portion of the skin and contract to maintain the tissue interface against the circular portion of the skin. The body may be removably attached to the attachment element. The input data may comprise a measurement, and the processing unit may be configured to modify at the energy signal based on the measurement. The processing unit may be configured determine a change of the measurement and modify the energy signal based on the change of the measurement.

The plurality of energy generators may be spaced apart on the distal surface of the body in a pattern; each energy generator may be operable to output the one or more energies in the signal direction toward a different point on the pattern; and the energy signal may comprise a plurality of symbols based on the pattern. Each symbol may comprise a plurality of dots, and each dot may correspond with one of the different points on the pattern. The plurality of symbols may comprise at least one alphanumeric symbol. The processing unit may be operable with the plurality of energy generators to scroll the plurality of symbols across the skin at a scroll rate in a communication direction transverse with the signal direction.

The input data may comprise vital signs of a subject, and the plurality of symbols may comprise a symbol associated with each vital sign. The plurality of symbols may comprise a symbol associated with an identity or location of the subject. The processing unit may be configured to: determine a change of the vital signs; and modify the one or both of the plurality of symbols and the scroll rate based on the change of the vital signs. The processing unit may be configured to: output one or more of the plurality of symbols with a first combination of the one or more energies when the change is within a predetermined range; and output the one or more of the plurality of symbols with a second combination of the one or more energies when the change is outside the predetermined range.

The data source may comprise one or more data sources, and the processing unit may be configured to: receive the input data from the one or more data sources; generate a control signal based on the input data; and cause the plurality of energy generators to output the energy signal according to the control signal. The processing unit may be configured to: determine a change in the input data; and modify the control signal based on the change of the input data. The control signal may comprise a scroll rate for the energy signal the processing unit may be configured to: determine the scroll rate based on the input data; and cause the plurality of generators to scroll the energy signal across the skin at the scroll rate.

Each energy generator may comprise a plurality of generator elements and a controller operable with the plurality of generator elements to output the plurality of energies; the control signal may comprise output commands for each controller of each energy generator; and each controller may be configured to receive the control signal, select one of the output commands, and cause one or more of the plurality of generator elements to output the one or more energies based on the selected one of the output commands.

Each energy generator may comprise a plurality of generator elements, and each generator element may be operable to output one of the plurality of energies in the signal direction. The plurality of generator elements may comprise one or more of: an impact generator element; a heat generator element; a shock generator element; and a pressure generator element. Each generator element may be configured to output the one of the plurality of energies toward a similar point or area on the skin. The plurality of generator elements may be arranged coaxially with a communication axis parallel to the signal direction.

The data source may comprise a local sensor that is attached to the body and configured to output a portion of the input data. The data source may comprise at least one remote sensor that is remote from the body and configured to output a portion the input data. The processing unit may be configured to receive the input data from a server in communication with the at least one remote sensor. The at least one remote sensor may comprise a health monitoring device. The device may comprise a power generator attached to the body. The power generator may comprise a photovoltaic cell mounted to a proximal surface of the body. The one or more energies may comprise: a first energy configured to communicate the energy signal; and a second energy configured to modify a penetration depth of the first energy. The first energy may be communicable with a first portion of the nerves, and the second energy may be communicable with a second portion of the nerves.

The body may comprise an impact absorbing material; and the attachment element may comprise a garment configured to maintain a position of the impact absorbing material relative to a user body. The processing unit may be configured to determine a direction of movement for the user body and output the energy signal based on the direction of movement. The processing unit may be configured to determine a change in the direction of movement and modify the energy signal based on the change in the direction of movement. The attachment element may comprise a shoe, and the distal surface of the body may comprise an interior surface of the shoe. The input data may comprise GPS signals, the processing unit may be configured to determine a direction of movement for a user body based on the GPS signals.

The attachment element may comprise a grip, and the body may comprise an exterior surface of the grip. The grip may be integral with a weapon comprising a sight, the input data may comprise data associated with an orientation of the sight, and the energy signal may be configured to communicate a status of the weapon based on the orientation of the sight. The input data may comprise data associated with an alignment of the sight with a target, and the processing unit may be configured to output the energy signal with a first combination of the one or more energies when the target is not aligned with the sight and a second combination of the one or more energies when the target is aligned with the sight.

The device may be implantable. The attachment element may comprise a bone plate engageable with a bone to orient the tissue interface toward an underside of the skin. The attachment element may comprise a tissue in-growth structure interactable with living tissue to maintain an orientation of the tissue interface toward an underside of the skin.

The plurality of energy generators may be arranged in bands; the attachment element may be configured to maintain each band against the skin; the input data may comprise input data for each band; and the processing unit may be configured to communicate with nerves associated with the skin by causing the plurality of energy generators in each band to output a different energy signal based on the input data for each band. The body may extend along a longitudinal axis; and the bands may be spaced apart along the longitudinal axis. The body may be configured to wrap around a limb so that the longitudinal axis of body is aligned with a longitudinal axis of the limb, and the bands wrap around the limb about the longitudinal axis. The processing unit may be operable with the plurality of energy generators to scroll each different energy signal in each band in a communication direction transverse with the signal direction. The input data for each band may comprise different vital signs, and each different energy signal may be based on one of the different vital signs.

The signal direction may comprise a first signal direction and the device may comprise an optical interface on a proximal surface of the body; the optical interface may comprise at least one display element operable to output at least one color toward eyes in a second signal direction opposite of the first signal direction; and the processing unit may be operable with the tissue interface and the optical interface to communicate simultaneously with nerves associated the skin and the eyes by outputting the energy signal with the one or more energies of the plurality of energies in the first signal direction and outputting an optical signal with the at least one color in the second signal direction.

The body may extend along a longitudinal axis, and the first and second signal directions may be transverse with the longitudinal axis. The energy signal and the optical signal may be scrolled together along or about the longitudinal axis. The processing unit may be configured to: receive the input data from the data source; generate a control signal based on the input data; cause the plurality of energy generators to output the energy signal according to the control signal; and cause the at least one display element to simultaneously output the optical signal according to the control signal. The energy signal may correspond with the optical signal.

The input data may comprise vital signs of a subject, the energy signal may comprise a plurality of symbols associated with the vital signs, and the optical signal may comprise the plurality of symbols. The processing unit may be configured to: determine a change of the vital signs; and modify the plurality of symbols based on the change of the vital signs. The device may comprise a motion sensor attached to the body, and the processing unit may be configured to selectively output the optical signal in response to the motion sensor.

Another exemplary aspect may comprise a system. For example, the system may comprise: a plurality of any communication devices described herein; and at least one processor that is in communication with the plurality of communication devices and configured to: generate a corrective motion signal based on position data for the plurality of communication devices; and cause each communication device to output its energy signal based on the corrective motion signal.

The system may comprise at least one position sensor configured to determine the position data and output the position data to the at least one processor. The position data may comprise an actual location of each communication device; and the at least one processor may be configured to generate the corrective motion signal based on the actual location of each communication device and a target location of each communication device. The position data may comprise an actual spatial configuration of the plurality of communication devices; and the at least one processor may be configured to generate the corrective motion signal based on the actual spatial configuration and a target spatial arrangement for the plurality of communication devices. The at least one processor may be configured to: determine a movement direction for each communication device based on the actual and target spatial arrangements; and cause each communication device to scroll its energy signal across the skin in the movement direction.

Each communication device may be mounted to a different part of a user body; and the target spatial arrangement may comprise a physical position of the user body defined by relative positions of each different part of the user body. The physical position of the user body may comprise a pose or a stance. The at least one processor may be configured to guide the user body through a series of different positions by determining the movement direction at intervals and modifying the energy signal for each interval.

Another exemplary aspect may comprise another communication device. In keeping with above, the device may comprise: a body comprising a distal surface compatible with skin; a tissue interface on the distal surface, the tissue interface comprising a plurality of energy generators, each energy generator being operable to output a plurality of energies in a signal direction toward the skin; and a processing unit configured to communicate with nerves associated with the skin by receiving input data, and causing the plurality of energy generators to output one or more energies of the plurality of energies in the signal direction.

The body may be flexible. The device may further comprise an attachment element configured to maintain the tissue interface in a position on or adjacent the skin. The distal surface of the body may comprise a biocompatible adhesive that is adherable to the skin. The body may comprise a plurality of communication bays, and each energy generator may be located in one of the communication bays. The attachment element may comprise a plurality of holes aligned with the plurality of communication bays, and each energy generator may be configured to output the plurality of energies through one of the holes. An interior surface of each communication bay or hole may be configured to direct the one or more energies in the signal direction. The interior surface may be configured to focus the at least one energy of one or more energies. The attachment element may comprise an elastic band. The body may be removably attached to the attachment element.

Another exemplary aspect may comprise another communication device. The communication device may comprise: a body comprising a distal surface compatible with skin; a tissue interface on the distal surface, the tissue interface comprising a plurality of energy generators, each energy generator being operable to output a plurality of energies in a signal direction toward the skin; an attachment element configured to maintain the tissue interface against the skin; and a processing unit configured to communicate an energy signal to nerves associated with the skin by receiving input data, and causing the plurality of energy generators to output one or more energies of the plurality of energies in the signal direction.

The plurality of energy generators may be spaced apart in a grid pattern, and each energy actuator may be operable to output the plurality of energies towards a different point on the grid pattern. The energy signal may comprise a plurality of symbols, each symbol may comprise a plurality of dots, and each dot may correspond with one of the different points on the grid pattern. The plurality of dots in each symbol may be arranged in a dot pattern within the grid pattern. The processing unit may be operable with the plurality of energy generators to scroll the plurality of symbols across the skin in a communication direction transverse with the signal direction. For example, the processing unit may be operable with the plurality of energy generators to output and scroll each symbol using a different combination of the one or more energies of the plurality of energies.

The input data may comprise a measurement, and the processing unit may be configured to communicate the energy signal by selecting the one or more energies of the plurality of energies based on the measurement. For example, the processing unit may be configured to communicate the energy signal by determining a change of the measurement and modifying the one or more energies of the plurality of energies based on the change of the measurement.

Another exemplary aspect may comprise another communication device. For example, the communication device may comprise: a body comprising a distal surface compatible with skin; a tissue interface on the distal surface, the tissue interface comprising a plurality of energy generators, each energy generator being operable to output a plurality of energies in a signal direction toward the skin; an attachment element configured to maintain the tissue interface on or adjacent the skin; and a processing unit configured to communicate an energy signal to nerves associated with the skin by: (i) receiving input data; (ii) selecting one or more energies of the plurality of energies based on the input data; and (iii) causing the plurality of energy generators to output the one or more energies in the signal direction.

The processing unit may be further configured to communicate the energy signal by: (iii) determining a change in the input data; and (iv) modifying the one or more energies based on the change. The processing unit may be further configured to communicate the energy signal by: (v) selecting a scroll rate based on the input data; and (vi) causing the plurality of generators to scroll the one or more energies across the skin at the scroll rate. The energy signal may comprise a plurality of symbols scrolled across the skin in a communication direction transverse with the signal direction. At least one symbol of the plurality of symbols may be an alphanumeric symbol.

Another exemplary aspect may comprise a communication method. The method may comprise: receiving, with a processing unit, input data for a communication device comprising a tissue interface maintainable on or adjacent skin, the tissue interface comprising a plurality of energy generators, each energy generator being operable to output a plurality of energies in a signal direction toward the skin; and operating, with the processing unit, the plurality of energy generators to communicate with nerves associated with the skin by outputting one or more energies of the plurality of energies in the signal direction based on the input data.

The receiving step may comprise receiving the input data from one or more data sources. For example, the one or more data sources may comprise at least one of patient monitoring device, a remote server, and a sensor. The receiving step may comprise receiving the input data from the one or more data sources at regular intervals, and the operating step may comprise outputting the one or more energies based on the input data received during each regular interval. The input data may comprise a control signal, and the operating step may comprise outputting the one or more energies based on the control signal.

The method may further comprise generating, with the processing unit, a control signal based on the input data, wherein the operating step comprises outputting the one or more energies based on the control signal. Generating the control signal to may comprise associating the input data with a plurality of symbols, and the operating step may comprise communicating the plurality of symbols to the skin with the one or more energies. For example, the input data may comprise vital signs of a patient, and each symbol may be associated with one or more of the vital signs. The one or more energies may comprise a first combination of the plurality of energies followed by a second combination of the plurality of energies. The one or more energies also may comprise a first energy communicable with a first portion of the nerves, and a second energy communication with a second portion of the nerves.

Another exemplary aspect may comprise another communication method. The method may comprise: receiving, with a processing unit, input data for a communication device comprising a tissue interface maintainable on or adjacent skin, the tissue interface comprising a plurality of energy generators, each energy generator being operable to output a plurality of energies in a signal direction toward the skin; and operating, with the processing unit, the plurality of energy generators to communicate an energy signal to nerves associated with the skin by outputting one or more energies of the plurality of energies in the signal direction based on the input data.

The operating step may comprise outputting different combinations of the one or more energies, and each different combination may communicate a different portion of the energy signal. The energy signal may comprise one or more symbols, and the operating step may comprise outputting the one or more energies to communicate the one or more symbols. The operating step may comprise scrolling the one or more symbols across the skin in a communication direction transverse with the signal direction. The one or more symbols may comprise an alphanumeric symbol.

The operating step may comprise: outputting a first combination of the one or more energies to communicate a first symbol of the one or more symbols, and outputting a second combination of the one or more energies to communicate a second symbol of the one or more symbols. The operating step may comprise: outputting a first combination of the one or more energies to communicate the energy signal, and outputting a second combination of the one or more energies to communicate a characteristic of the energy signal. The input data may comprise a measurement, and the operating step may comprise outputting the one or more energies based on the measurement. For example, the operating step may comprise modifying the one or more energies based on a change of the measurement.

Another exemplary aspect may comprise another communication method. For example, the method may comprise: receiving, with a processing unit, input data for a communication device comprising a tissue interface maintainable on or adjacent skin, the tissue interface comprising a plurality of energy generators, each energy generator being operable to output a plurality of energies in a signal direction toward the skin; generating, with the processing unit, a control signal based on the input data; and operating, with the processing unit, the plurality of energy generators to communicate with to nerves associated with the skin by outputting one or more energies of the plurality of energies in the signal direction based on the control signal.

Another exemplary aspect may comprise another communication device. The device may comprise: a body comprising a distal surface compatible with skin; a tissue interface on the distal surface, the tissue interface comprising a plurality of energy generators arranged in bands, each energy generator being operable to output a plurality of energies in a signal direction toward the skin; and a processing unit configured to communicate with nerves associated with the skin by receiving input data, and causing the plurality of energy generators in each band to output one or more energies of the plurality of energies in the signal direction.

The body may be flexible. The device may further comprise an attachment element configured to maintain the tissue interface in a position on or adjacent the skin. For example, the attachment element may comprise a distal surface adherable to the skin. The attachment element may be proximal of the tissue interface and configured to maintain the bands against the skin. The attachment element may be configured to maintain the bands against the skin by applying a tensile force to the body.

Another exemplary aspect may comprise another communication device. The device may comprise: a body extending along a longitudinal axis, and comprising a distal surface compatible with skin; a tissue interface on the distal surface, the tissue interface comprising a plurality of energy generators arranged in bands spaced apart along the longitudinal axis, each energy generator being operable to output a plurality of energies in a signal direction toward the skin; an attachment element configured to maintain the bands of the tissue interface against the skin; and a processing unit configured to communicate energy signals to nerves associated with the skin by receiving input data, and causing the plurality of energy generators to output an energy signal in each band with one or more energies of the plurality of energies.

The body may be configured to wrap around a limb so that the longitudinal axis of body is aligned with a longitudinal axis of the limb, and the bands wrap around the limb about the longitudinal axis. The processing unit may be configured to move the energy signal in each band so as to scroll the energy signal around the limb. The one or more energies may comprise: a first energy configured to communicate one or more symbols; and a second energy configured to modify the one or more symbols.

Another exemplary aspect may comprise another communication method. The method may comprise: receiving, with a processing unit, input data for a communication device comprising a tissue interface maintainable on or adjacent skin, the tissue interface comprising a plurality of energy generators arranged in bands, each energy generator being operable to output a plurality of energies in a signal direction toward the skin; and causing, with the processing unit, the plurality of energy generators in each band to communicate with nerves associated with the skin by outputting one or more energies of the plurality of energies in response to the input data.

The receiving step may comprise receiving the input data from one or more data sources. For example, the receiving step may comprise: receiving input data comprise a plurality of measurements; and causing the plurality of energy generators in each band to output the one or more energies based on one measurement of the plurality of measurements. The method may further comprise outputting a first combination of the one or more energies when the one measurement is inside of an acceptable range; and outputting a second combination of the one or more energies when the one measurement is outside of the acceptable range.

The receiving step may comprise receiving input data comprising a plurality of vital signs; and the causing step may comprise causing the plurality of energy generators in each band to output the one or more energies based on one vital sign of the plurality of vital signs. The input data may comprise a control signal for each band, and the operating step may comprise outputting the one or more energies based on the control signal for each band. The method may further comprise generating, with the processing unit, a control signal for each band based on the input data, wherein the operating step may comprise outputting the one or more energies based on the control signal for each band.

Another exemplary aspect may comprise another communication method. The method may comprise: receiving, with a processing unit, input data for a communication device comprising a tissue interface maintainable on or adjacent skin, the tissue interface comprising a plurality of energy generators arranged in bands, each energy generator being operable to output a plurality of energies in a signal direction toward the skin; and causing, with the processing unit, the plurality of energy generators to communicate energy signals to nerves associated with the skin by outputting an energy signal in each band with one or more energies of the plurality of energies. The energy signal may comprise one or more symbols based on the input data, and the operating step may comprise outputting the one or more symbols to the skin with one or more energies. The operating step may comprise scrolling the one or more symbols across the skin in a communication direction transverse with the signal direction.

Another exemplary aspect may comprise a communication system. The system may comprise: (A) a plurality of communication devices, each communication device comprising: a body comprising a distal surface compatible with skin; and a tissue interface on the distal surface, the tissue interface comprising a plurality of energy generators, each energy generator being operable to output a plurality of energies in a signal direction toward the skin; and (B) a processing unit in communication with at least one of the plurality of communication devices and configured to: generate, with one or more processors, a corrective motion signal based on position data for the plurality of communication devices; and operate, with the one or more processors, the plurality of energy generators of each communication device to output one or more energies of the plurality of energies in the signal direction based on the corrective motion signal.

The system may further comprise at least one position sensor configured to determine the position data and output the position data to the processing unit. The position data may comprise an actual location of each device of the plurality of communication devices; and the processing unit may be configured to generate, with the one or more processors, the corrective motion signal based on the actual locations and a target location for each device of the plurality of communication devices.

The position data may comprise an actual spatial arrangement of the plurality of communication devices; and the processing unit may be configured to generate, with the one or more processors, the corrective motion signal based on the actual spatial arrangement and a target spatial arrangement for the plurality of communication devices. The processing unit may be configured to: determine, with the one or more processors, a movement direction for each communication device based on the actual and target spatial arrangements; and operate, with the one or more processors, the plurality of energy generators of each communication device to output the one or more energies toward the skin in the signal direction and move the one or more energies across the skin the movement direction.

Another exemplary aspect may comprise another communication method. The method may comprise: generating, with one or more processors, a corrective motion signal for a plurality of communication devices based on position data, each communication device comprising a tissue interface with a plurality of energy generators, each energy generator being operable to output a plurality of energies in a signal direction toward the skin; and operating, with the one or more processors, the plurality of energy generators of each communication device to output one or more energies of the plurality of energies in the signal direction based on the corrective motion signal. The method may comprise receiving the position data from the plurality of communication devices or a remote position sensor.

Another exemplary aspect may comprise another communication method. The method may comprise: receiving, with one or more processors, position data for a plurality of communication devices mountable on or adjacent skin, each device comprising a tissue interface with a plurality of energy generators, each energy generator being operable to output a plurality of energies in a signal direction toward the skin; receiving or generating, with the one or more processors, a corrective motion signal for the plurality of communication devices based on position data for each communication device; and operating, with the one or more processors, the plurality of energy generators of each communication device to output one or more energies of the plurality of energies in the signal direction based on the corrective motion signal.

At least one of the communication devices may comprise a position sensor, and the method may comprise receiving, with the one or more processors, the position data from the position sensor. The method may comprise: determining, with the one or more processors, an actual spatial arrangement of the plurality of communication devices based on the position data; and identifying, with the one or more processors, a target spatial arrangement for the plurality of communication devices, wherein the generating step comprises generating, with the one or more processors, the corrective motion signal based on the actual spatial arrangement and the target spatial arrangement. The method may comprise: determining, with the one or more processors, a movement direction for each communication device based on actual and target spatial arrangements; and operating, with the one or more processors, the plurality of energy generators of each communication device to output one or more energies toward the skin in a shape associated with the movement direction for each communication device.

The method may comprise operating, with the one or more processors, the plurality of energy generators of each communication device to move the shape across the skin in the movement direction. Each communication device may be mounted to a different portion of a body; and the target spatial arrangement may comprise a physical position of the body defined by the relative positions of each different portion of the body. The physical position of the body may comprise at least one of a stretching position, a lifting position, a pose, or a stance.

The target spatial arrangement may comprise a series of target spatial arrangements, and the method may comprise: selecting arrangements from the series of target spatial arrangements; and repeating the determining, generating, and operating steps for each selected arrangement. The selecting step may be performed at predetermined intervals so as to coordinate relative movements between each selected arrangement. The series of target spatial arrangements may comprise one or more stretches, yoga poses, or defensive postures.

Another exemplary aspect may comprise another communication device. The device may comprise: a body comprising a proximal surface compatible with eyes, and a distal surface compatible with skin; a tissue interface on the distal surface, the tissue interface comprising a plurality of energy generators, each energy generator comprising a tissue interface operable to output a plurality of energies in a first signal direction toward the skin; an optical interface on the proximal surface, the optical interface comprising at least one display element operable to output at least one color in a second signal direction toward the eyes; and a processing unit operable with the tissue interface and the optical interface to communicate simultaneously with nerves associated with skin and eyes by outputting one or more energies of the plurality of energies in the first signal direction and at least one color in the second signal direction.

The body may extend along a longitudinal axis, and the first signal direction may be transverse with the longitudinal axis. The second signal direction may be transverse with the longitudinal axis. The first and second signal directions may extend oppositely along a signal axis transverse with the longitudinal axis. The body may be conformable with a curved shape. The body comprises a flexible body configured to wrap around a limb so that the longitudinal axis has a circular shape.

The processing unit may receive input data from one or more sources, the one or more energies may be output as an energy signal based on the input data, and the one or more colors may be simultaneously output as an optical signal based on the input data. The energy signal may correspond with the optical signal. The outputs may be flashed or scrolled together. For example, the optical signal and the energy signal may be scrolled together along the longitudinal axis. The input data may comprise a vital sign of the patient, the energy signal may communicate the vital sign to the skin, and the optical signal may simultaneously communicate the vital sign to the eyes. The processing unit may be configured to determine a change of the vital sign over time and simultaneously modify one or both of the optical signal and the energy signal based on the change. The input data may comprise alphanumeric symbols, the optical signal may communicate the alphanumeric symbols to the eyes, and the energy signal may simultaneously communicate the symbols to skin.

Another exemplary aspect may comprise another communication device. The device may comprise: a body extending along a longitudinal axis, the body comprising a proximal surface compatible with eyes and a distal surface compatible with skin; a tissue interface on the distal surface of the body, the tissue interface comprising a plurality of energy generators, each energy generator being operable to output a plurality of energies in a first signal direction toward the skin; an optical interface on the proximal surface, the optical interface comprising at least one display element operable to output at least one color in a second signal direction toward the eyes; a sensor on the body; and a processing unit configured to communicate simultaneously with nerves associated with the eyes and the skin by: receiving input data from the sensor or a remote data source, causing the plurality of energy generators to output one or more energies of the plurality of energies in the first signal direction as an energy signal, and causing the display element to output the at least one color in the second signal direction as an optical signal.

The first and second communication signals may be scrolled together along the longitudinal axis. The energy signal may be output continuously. The optical signal may be output in response to a movement detected by the sensor. The movement may comprise aligning the optical interface with the eyes.

Another exemplary aspect may comprise another communication device. The device may comprise: a body comprising a proximal surface compatible with eyes and a distal surface compatible with skin; a tissue interface on the distal surface of the body, the tissue interface comprising a plurality of energy generators, each energy generator being operable to output a plurality of energies in a first signal direction toward the skin; at least one sensor; an optical interface on the proximal surface, the optical interface comprising at least one display element operable to output at least one color in a second signal direction toward the eyes; a processing unit configured to communicate simultaneously with nerves associated with the eyes and the skin by: receiving vital sign data from the at least one sensor, causing the plurality of energy generators to output one or more energies of the plurality of energies in the first signal direction as an energy signal, and causing the at least one display element to output the at least one color in the second signal direction as an optical signal.

The energy signal and the optical signal may be scrolled across the body in a communication direction transverse with the longitudinal axis. The at least one display element may comprise a touchscreen, and the energy signal may be moveable together with optical signal along or around the longitudinal axis by operation of the touchscreen. The first direction may be transverse with the second direction.

BRIEF DESCRIPTION OF THE DRAWINGS

The accompanying drawings are incorporated in and constitute a part of this specification. These drawings illustrate exemplary aspects of the present disclosure that, together with the written descriptions provided herein, serve to explain the principles of this disclosure.

DETAILED DESCRIPTION

Figure 1A:
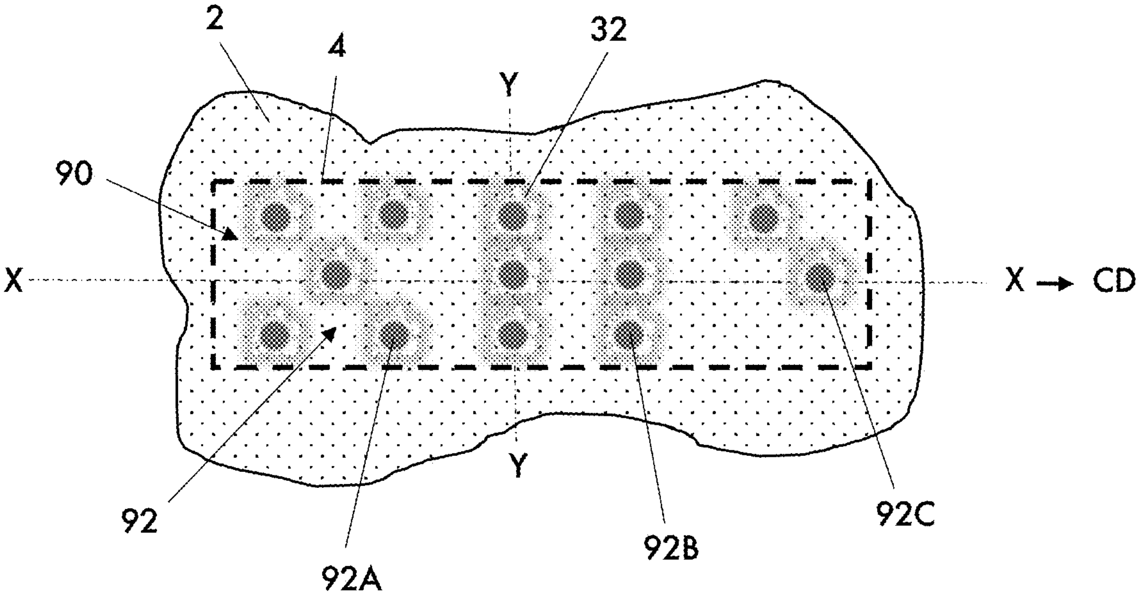
FIG. 1A depicts an exemplary energy signal output onto a living tissue.

Aspects of the present disclosure are now described with reference to exemplary communication devices, methods, and systems. Particular aspects reference a healthcare setting, wherein the described devices, methods, and systems may allow a single caregiver to monitor vital signals for a plurality of patients without using a screen, or at least with a reduced amount of screen time. Any references to a particular setting, such as healthcare; a particular user, such as a caregiver; a particular data, such as vital signals; or particular amount of screen time, are provided for convenience and not intended to limit the present disclosure unless claimed. Accordingly, the aspects disclosed herein may be utilized for any analogous communication device, method, or system-healthcare-related or otherwise.

The terms "proximal" and "distal," and their respective initials "P" and "D," may be used to describe relative components and features. Proximal may refer to a position closer to a hand of user, whereas distal may refer to a position further away from said hand. With respect to a hand adjacent a living tissue, for example, proximal may refer to a position away from the tissue, whereas distal may refer to a position toward said tissue. As a further example, with respect to energy directed toward the living tissue, proximal may refer to energy directed away from the tissue and distal may refer to energy directed toward the tissue. Appending the initials P or D to a number may signify its proximal or distal location or direction. Unless claimed, these directional terms are provided for convenience and not intended to limit this disclosure.

Aspects of this disclosure may be described with reference to one or more axes. For example, an element may extend along an axis, be moved along said axis in first or second direction, and/or be rotated about said axis in a first or second direction. One axis may intersect another axis, resulting in a transverse and/or perpendicular relationship therebetween. For example, two or three perpendicular axes may intersect at an origin point to define a Cartesian coordinate system. The directional terms proximal and distal may be used with reference to any axis. One axis may be a longitudinal axis extending along a length of an element, such as a central longitudinal axis extending along the length and through a centroid of the element.

Terms such as "may," "can," and like variation, are intended to describe optional aspects of the present disclosure, any of which may be covered by the claims set forth below. Terms such as "comprises," "comprising," or like variation, are intended to describe a non-exclusive inclusion, such that a device, method, or system comprising a list of elements does not include only those elements, but may include other elements not expressly listed or inherent thereto. The term "and/or" indicates a potential combination, such that a first and/or second element may likewise be described as a first element, a second element, or a combination of the first and second elements. These potential combinations are provided as examples. Numerous other combinations are inherent to this disclosure. Unless stated otherwise, the term "exemplary" is used in the sense of "example" rather than "ideal."

Aspects of this disclosure are directed to devices, methods, and systems for communicating with the brain through nerves associated with a living tissue. Some aspects are described with reference to an energy signal including one or more energies output to communicate symbols to the living tissue. The symbols may be used to communicate data, and the one or more energies may be used to communicate aspects of the data. The living tissue may be a portion of skin, as shown in FIGS. 1A-8D. In a healthcare setting, the energy signal may be output towards the skin of a caregiver to communicate symbols associated with a status of a patient. For example, an intensity of the one or more energies may escalate responsive to a measure of the status, providing a non-visual alert to the caregiver if the measure changes.

Exemplary energies and energy signals are now described with reference to FIG. 1A, which depicts an exemplary energy signal 90 including a plurality of symbols 92 output onto a communication area 4 of a skin 2 with one or more energies 32. For illustrative purposes, the symbols 92 of FIG. 1 are shown from a proximal-to-distal direction, as they would be output to skin 2 by an energy transceiver. Each energy 32 may be configured to communicate aspects of the data to the brain through nerves associated with skin 2, such as nerves located distal of communication area 4. For example, the one or more energies 32 shown in FIG. 1A may be recognizable by touch receptors, such as the Meissner's corpuscle; temperature receptors, such the Ruffini corpuscle and Krause corpuscle; electrical receptors, such as the muscles and pain receptors located in the dermis layer; pressure receptors such as the Pacinian corpuscle; and/or other cutaneous or subcutaneous nerves that innervate the skin or other living tissue.

Each symbol 92 may be associated with different data. For example, in the healthcare setting, each symbol 92 may be associated with a vital sign of the patient, such as body temperature, pulse rate, respiration rate, and/or blood pressure. As shown in FIG. 1A, the plurality of symbols 92 may include a first symbol 92A, a second symbol 92B, and a third symbol 92C. In keeping with the previous example, first symbol 92A may be associated with temperature and pulse rate, second symbol 92B may be associated with respiration rate, and third symbol 92C may be associated with blood pressure. Any number of symbols 92 may be provided and/or associated with a measurable or non-measurable characteristic of the patient.

Symbols 92A, 92B, and 92C are shown as pip patterns of dots in FIG. 1A, wherein each dot is a shaded area. Each dot may represent an output of the one or more energies 32. Aspects of energies 32 and/or each symbol 92A, 92B, and 92C may increase the complexity of energy signal 90, and thus the amount of data transmitted therewith. As shown in FIG. 1A, symbols 92A, 92B, and 92C may be scrolled across communication area 4 by outputting energies 32 toward the skin in the pip patterns; and moving the patterns across the skin in a communication direction CD. In FIG. 1A, first symbol 92A is a pip five dot pattern; second symbol 92B is a pip six dot pattern; and a third symbol 92C is a pip three dot pattern that has been truncated by an end of communication area 4 due to the scrolling. Symbols 92 may be flashed and scrolled. For example, the five dots of first symbol 92A in FIG. 1A may be output to communicate a temperature range of the patient (e.g., a normal range), and flashed on-and-off to communicate the pulse rate of the patient.

Figure 1B:
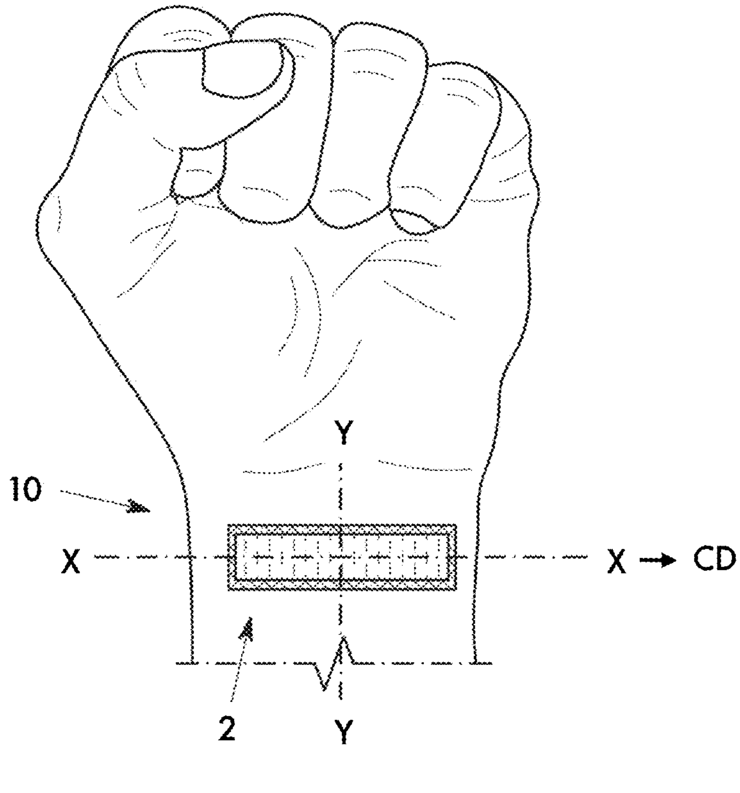
FIG. 1B depicts an exemplary communication device configured to output the energy signal of FIG. 1A.

An exemplary energy transceiver 10 is depicted in FIG. 1B as being configured output energy signal 90 to communication area 4 of skin 2. As shown, energy transceiver 10 may be attached to a portion of skin 2, including any portion located on a limb, such as the underside of a human wrist shown in FIG. 1B for example. Communication area 4 may be sized approximate to a perimeter of transceiver 10. In this configuration, transceiver 10 may be configured to communicate energy signal 90 to skin 2 by outputting the one or more energies 32 toward communication area 4 in a signal direction oriented toward skin 2. As shown in FIG. 1A, the energies 32 may be output individually and/or in combination to communicate aspects of any of symbols 92A, 92B, and 92C to skin 2.

Additional aspects of exemplary energy transceiver 10 are now described with reference to FIGS. 2A-C. As shown, transceiver 10 may comprise: a body 20; a tissue interface 30; a processing unit 60; and an attachment element 70. With these elements, and the variations described herein, energy transceiver 10 may be configured to communicate energy signal 90 to nerves associated with skin 2 by outputting the one or more energies 32 towards skin 2 with tissue interface 30.

Figure 2A:
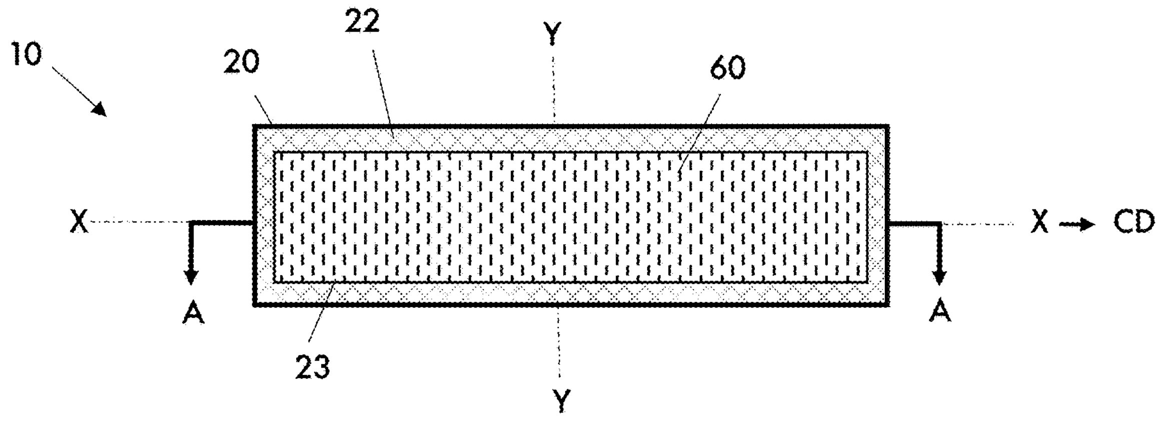
FIG. 2A depicts a top-down view of the FIG. 1B device.
Figure 2B:
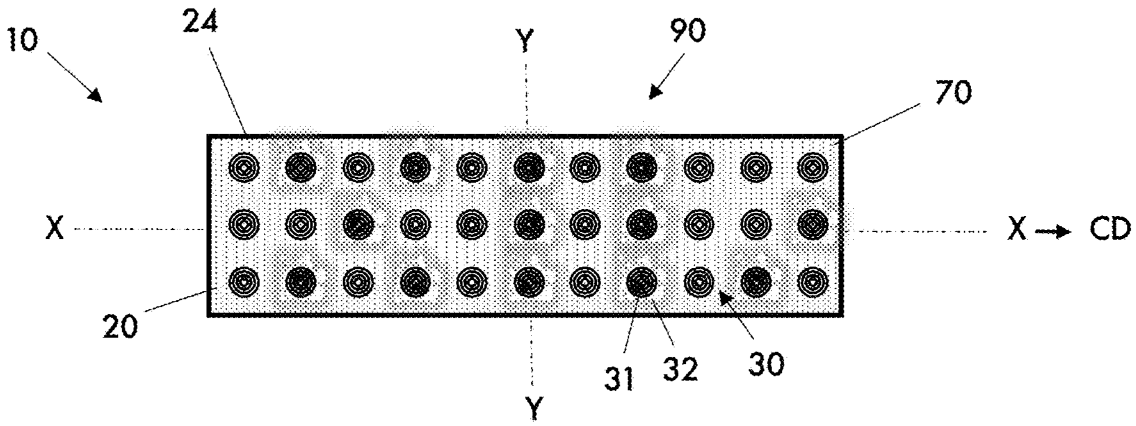
FIG. 2B depicts a bottom-up view of the FIG. 1B device.
Figure 2C:
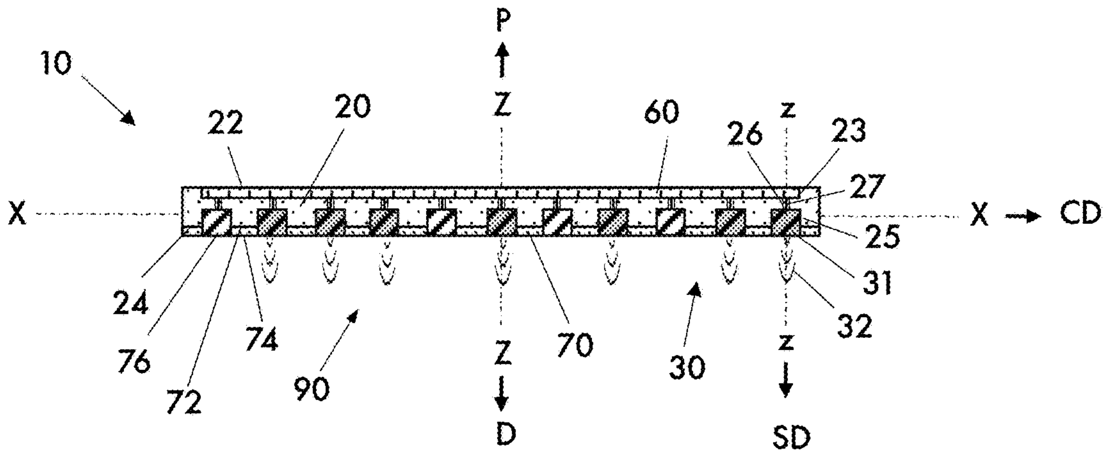
FIG. 2C depicts a cross-section view of the FIG. 1B device taking along section line A-A of FIG. 2A.

As shown in FIGS. 2A-C, body 20 may contain the elements of energy transceiver 10. For example, body 20 of FIGS. 2A-C has a length extending along a longitudinal axis X-X, a width extending along a lateral axis Y-Y, and a thickness extending along a proximal-distal axis Z-Z. The length, width, and/or thickness of body 20 may be compatible with skin 2. For example, body 20 may be composed of a flexible biocompatible base material, such as a polymeric material, so that the length and width of body 20 are conformable against a curvature of skin 2.

Body 20 may include any shape and be conformable with any curvature. For example, body 20 may be conformable with a cylindrical shape of a human forearm (e.g., FIG. 1B), a semi-spherical shape a human forehead (e.g., FIG. 6B), or an irregular curved shape of a human foot (e.g., FIG. 7A). A plurality of bodies 20 may be joined together to accommodate some curvatures. For example, side surfaces of body 20 of FIGS. 2A-C may be removable engageable with side surfaces of additional bodies 20 to create a joined layer conformable with the curvature.

The base material of body 20 may have insulating and/or energy-directing properties. For example, the base material may include compositions and/or coatings that promote energy flows along proximal-distal axis Z-Z, and limit energy flows along axes X-X and/or Y-Y. Body 20 may be manufactured from the base material using any known process. For example, body 20 may be molded or 3D printed from a base material that is biocompatible, dielectric, impact resistance, sound absorbing, and/or thermally resistant, such as polyether ether ketone (PEEK) and like polymeric materials. Additional materials and/or coatings may be included with the base material and/or applied to body 20 to further promote biocompatibility.

As shown in FIGS. 2A-C, body 20 may define a proximal surface 22 (FIG. 2A) opposite of a distal surface 24 (FIG. 2B) along proximal-distal axis Z-Z (FIG. 2C). In FIGS. 2A and 2C, for example, proximal surface 22 includes a processor compartment 23 configured to receive processing unit 60. As shown, and described further below, processing unit 60 may be removable engageable (e.g., snap-fit into) with processor compartment 23. Body 20 may include and/or be compatible with additional mechanisms for securing and/or releasing the snap-fit, such as a retaining screw and/or a lever.

Body 20 of FIGS. 2A-C includes a plurality of communication bays 25. As shown, each communication bay 25 may be spaced apart from the next on distal surface 24 in a grid pattern. The spacing may be uniform or non-uniform. In FIGS. 2B and 2C, the bays 25 are spaced apart uniformly for communication with the skin 2 of FIG. 1B, which has a fairly planar surface area. Non-uniform spacing may be used to accommodate a curvature of skin 2. As shown in FIG. 2C, each communication bay 25 may extend proximally into body 20 through distal surface 24 along a communication axis z-z that is parallel with the proximal-distal axis Z-Z of transceiver 10. In FIG. 2C, a conduit 26 extends proximally from each bay 25, through an interior portion of body 20, and into processor compartment 23, placing the plurality of bays 25 in communication with compartment 23.

Aspects of tissue interface 30 are now described with reference to FIGS. 2B and 2C. As shown, tissue interface 30 may include a plurality of energy generators 31, and each generator 31 may be located in one of communication bays 25. Each generator 31 may be operable with processing unit 60 to output energies 32 individually and/or in combination. In FIGS. 2B and 2C, for example, the one or more energies 32 are being output from the shaded generators 31 to communicate energy signal 90 of FIG. 1A. As shown in FIG. 2C, one or more conductors 27 may extend through each conduit 26 to connect processing unit 60 to each energy generator 31, allowing control signals to be transmitted between processing unit 60 and the plurality of energy generators 31 along one or more pathways.

As shown in FIG. 2C, the one or more conductors 27 may include any number of electrical wires and/or optical fibers configured to transmit the control signals. For example, the conductors 27 may comprise a plurality of electrical conductors interconnecting the plurality of generators 31 with processing unit 60, and allowing electricity-based control signals, energies, and communications to be transmitted between unit 60 and generators 31. In addition or alternatively, the conductors 27 may comprise a plurality of optical fibers interconnecting the plurality of generators with processing unit 60, and allowing light-based control signals, energies, and communications to be transmitted between unit 60 and generators 31. For example, each conductor 27 may comprise a twisted pair including at least one electrical conductor and at least one optical fiber. A flexible energy-insulating medium, such as an epoxy, may be used to seal conductors 27 in conduits 26.

Figure 3A:
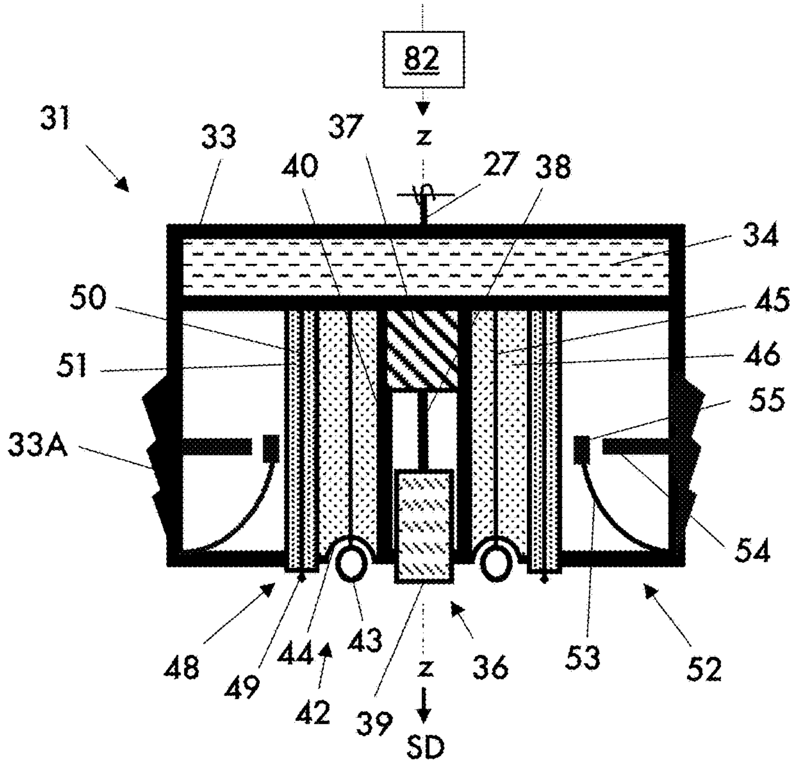
FIG. 3A depicts a cross-section of an exemplary energy generator.

A cross-section of an exemplary energy generator 31 is depicted in FIG. 3A. As shown, each generator 31 may include: a housing 33; a controller 34; and a plurality of generator elements, such as: an impact generator element 36; a heat generator element 42; a shock generator element 48; and a pressure generator element 52. Examples of each generator element are now described.

Similar to body 20, housing 33 may include an insulating material that surrounds portions of each generator 31 and/or defines mounting surfaces for generator elements 36, 42, 48, and/or 52. For example, housing 33 may be made of the same base material as body 20 or a compatible material; and/or formed together with body 20 by a molding, printing, or like process. As described below, portions of each generator element 36, 42, 48, and/or 52 may extend distally from housing 33 to contact skin 2. Housing 33 of FIG. 3A includes an attachment feature 33A configured to secure each generator 31 in one of the communication bays 25. For example, attachment feature 33A may include a set of threads on housing 33 that are engageable with an interior surface of bays 25. Other types of chemical or mechanical attachment may be used, including biocompatible adhesives, snap-fit connections, and the like.

Figure 3B:
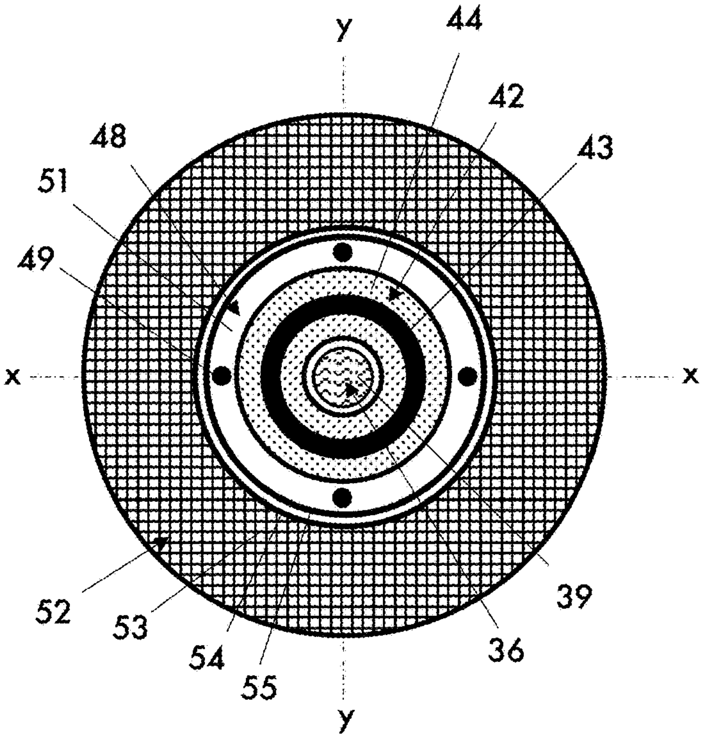
FIG. 3B depicts a bottom-up view of the FIG. 3A generator.

Exemplary generator elements 36, 42, 48, and 52 may be arranged to output their respective energies 32 in approximately the same direction. As shown in FIGS. 3A and 3B, each generator element 36, 42, 48, and 52 may be arranged coaxially with communication axis z-z so that each energy 32 may be output toward skin 2 in signal direction SD. Because of this coaxial configuration, each energy 32 may be output toward approximately the same point or area on skin 2, making the energies 32 interchangeable. For example, any of the dots included in energy signal 90 of FIG. 1A may be interchangeably communicated to approximately the same point on skin 2 with any of the energies 32.

As shown in FIG. 3A, controller 34 may be configured receive a control signal 82 from processing unit 60, and activate generator elements 36, 42, 48, and 52 according to signal 82. The one or more conductors 27 may transmit the control signal 82 to generator elements 36, 42, 48, and 52 from processing unit 60 and/or direct electricity to generator elements 36, 42, 48, and 52 from a power source 66 of processing unit 60 (e.g., FIG. 5). Energy transceiver 10 may be an all-electrical device, wherein control signal 82 is an electrical signal and first and the conductors 27 are electrical wires. For varied response times, and energy requirements, transceiver 10 also may be an electro-optical device, wherein control signal 82 includes an optical signal, and at least one of the conductors 27 includes an optical fiber. For example, controller 34 may receive control signal 82 from processing unit 60 with a first one of conductors 27 (e.g., a first electrical and/or optical conductor), and direct electricity to one or more of the generator elements 36, 42, 48, and 52 with a second one of conductors 27 (e.g., a second electrical conductor) according to signal 82.

Figure 4A:
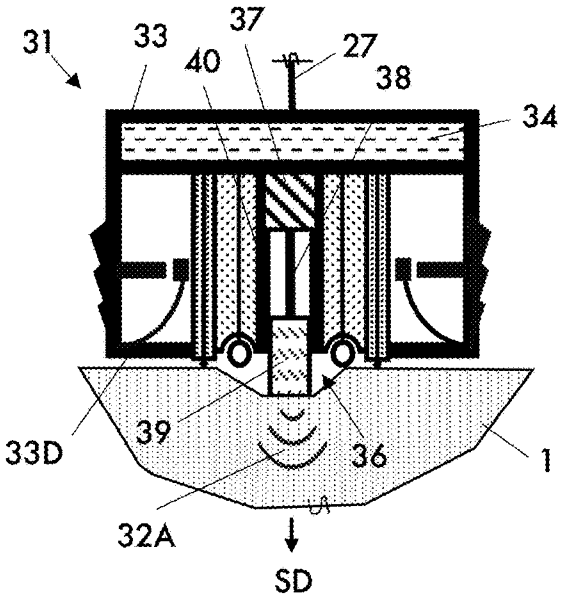
FIG. 4A depicts an impact energy output with the FIG. 3A generator.

Additional aspects of generator elements 36, 42, 48, and 52 are now described with reference to FIGS. 4A-D. As shown in FIG. 4A, for example, impact generator element 36 may be configured to communicate an impact energy 32A to the brain through nerves associated with skin 2. For example, impact generator element 36 may be a mechanical actuator that converts electricity from power source 66 into a mechanical movement recognizable by touch receptors of skin 2, such as Meissner's corpuscle. As shown, generator element 36 may include a drive mechanism 37, a piston 38, a tissue contact 39, and a guide tube 40. Drive mechanism 37 may include a motor assembly that is attached to controller 34 and conductively engaged therewith. In this configuration, controller 34 may direct electricity to drive mechanism 37, causing the motor assembly to move piston 38 distally along communication axis z-z, outputting impact energy 32A in signal direction SD. Different force transfer components also may be used to apply energy 32A, including levers and like actuators.

As shown, drive mechanism 37 may be configured to move piston 38 between a retracted position, wherein tissue contact 39 is contained housing 33 (e.g., FIG. 3A); and an extended position, wherein at least a portion of contact 39 is distal of housing 33 (e.g., FIG. 4A). Accordingly, impact energy 32A may be output in signal direction SD as a physical movement of skin 2 caused by moving tissue contact 39 distally. Aspects of impact energy 32A may be modified. For example, outer tube 40 may be attached to housing 33 and include interior surfaces configured to modify the timing of energy 32A by guiding the proximal-distal movements of tissue contact 39 (e.g., by rotating or stabilizing contact 39). A resilient element may be added between drive mechanism 37 and contact 39 to dampen such movements.

Figure 4B:
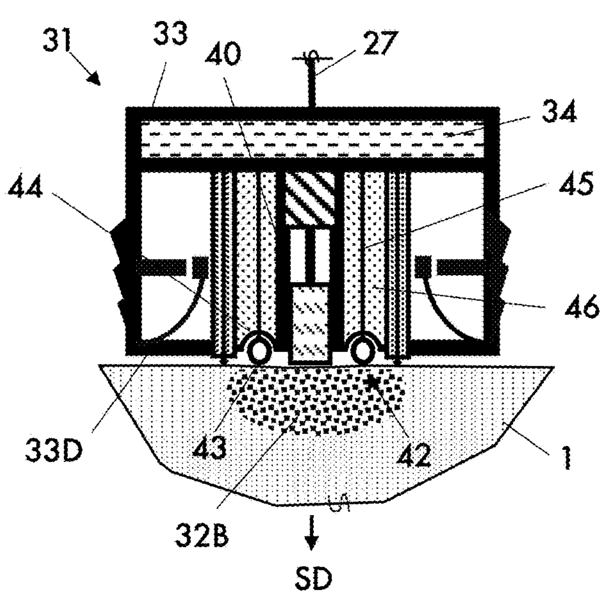
FIG. 4B depicts a heat energy output with the FIG. 3A generator.

Heat generator element 42 may be configured to communicate a heat energy 32B to the brain through nerves associated with skin 2. As shown in FIG. 4B, generator element 42 may include an electrical resistor that converts electricity from power source 66 into an amount of heat recognizable by temperature receptors of skin 2, such the Ruffini corpuscle. For example, heat generator element 42 may include an electrical resistor 43, a heat reflecting groove 44, a conductor 45, and an insulating material 46. Groove 44 may include a metal plate attached to an exterior surface of outer tube 40 of generator element 36. Resistor 33 may include an electrical wire or coil attached to groove 44. Conductor 45 may include an electrical wire extend between controller 34 and resistor 43, and material 46 may including an epoxy surrounding conductor 45.

As shown in FIG. 3B, electrical resistor 43 and heat-reflecting groove 44 may be circular elements arranged coaxially with communication axis z-z. Conductor 45 may be configured to transmit electricity to electric resistor 43 for conversion into heat energy 32B. Groove 44 may include a concave shape extending proximally into housing 33 to contain resistor 43, and the shape may include a distal surface configured to reflect heat energy 32B toward skin 2. In this configuration, heat signal 32B may be output in signal direction SD as an amount of heat transferred to skin 2 by resistor 43. Aspects of heat signal 32B may be modified. For example, the size, shape, and/or exterior coating of resistor 43 or groove 44 may be configured to modify the intensity of heat energy 32B.

Figure 4C:
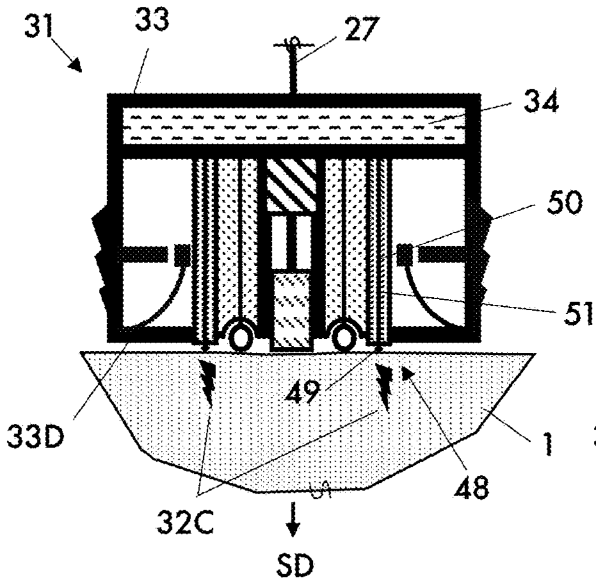
FIG. 4C depicts an electrical energy output with the FIG. 3A generator.

Shock generator element 48 may be configured to communicate an electrical energy 32C to the brain through nerves associated with skin 2. As shown in FIG. 4C, shock generator element 48 may be an electroshock generator that converts electricity from power source 66 into an electrical shock recognizable by electricity-sensitive receptors, such as the muscles and pain receptors located in the dermis layer of skin 2. For example, energy generator element 48 may include at least two electric contacts 49, a conductor 50, and an insulating material 51. The conductors 50 may be metallic rods or wires extending distally from controller 34. Insulating material 51 may be an epoxy surrounding each conductor 50. Each contact 49 may include a discharge shape located on the distal-most end of one of conductors 50. In this configuration, controller 34 may direct electricity through conductors 50, and into the discharge shape of contact 49, allowing electricity to flow through skin 2 between the contacts 49 to output electrical energy 32C.

As shown in FIG. 3B, the electrical contacts 49 may be spaced apart in a radial pattern coaxial with communication axis z-z. Any number of contacts 49 may be used, in any geometrical and/or spatial configuration. Insulating material 51 may be used to define and maintain the spacing. As shown, insulating materials 51 and 46 may be the same material, such as an epoxy. Four contacts 49 are shown in FIG. 3B, for example, as being arranged in two pairs. Aspects of electrical energy 32C may be modified. For example, the arrangement of contacts 49 may be changed; and/or the size of or spacing between each contact 49 changed to modify the intensity of energy 32C.

Figure 4D:
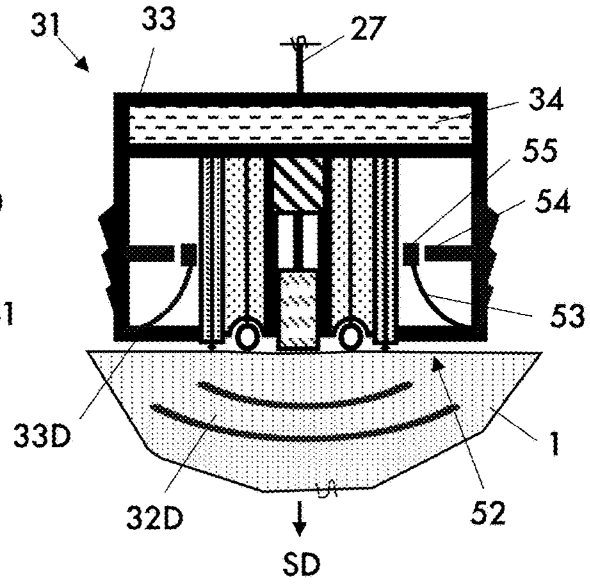
FIG. 4D depicts a pressure energy output with the FIG. 3A generator.

Pressure generator element 52 may be configured to communicate a pressure energy 32D to the brain through nerves associated with skin 2. As shown in FIG. 4D, pressure generator element 52 may be an electroacoustic transducer that converts electricity from power source 66 into a sound wave recognizable by pressure receptors of skin 2, such as the Pacinian corpuscle. For example, pressure generator element 52 may include a cone 53, a voice coil 54, and a magnet 55. In this configuration, controller 34 may direct electricity into voice coil 54 for interaction with magnet 55, causing movements of cone 53 that generate the pressure energy 32D in signal direction SD.

As shown in FIGS. 3B and 4D, cone 53 may have a frustoconical shape that is coaxial with communication axis z-z. An outer edge of cone 53 may be attached an interior surface of housing 33, and an inner edge of cone 53 may be attached to voice coil 54, which may be coupled to controller 34 and power source 66 by one or more conductors. As shown, coil 54 may have a circular shape, and generator elements 36, 42, and 48 may be located in the interior of said shape. Aspects of pressure energy 32D may be modified. For example, cone 53 and/or voice coil 54 may include a surround, a spider, a secondary frame, or any other structures configured to modify signal responsiveness; the strength of magnet 55 may be varied; and/or controller 34 may include an amplifier configured to modify an intensity of pressure energy 32D.

Different generator element types also may be used to communicate signals to the skin with different energies 32, and/or different combinations of energies 32. For example, the plurality of generators 31 may be modified to vary individual or combined outputs of energies 32A, 32B, 32C, and 32D; and/or include additional generator elements configured to output additional signals to skin 2, including optical signals, magnetic signals, and/or any physically recognizable signals. Any type of generator element may be used and likewise coaxially arranged according to FIGS. 3A through 4D.

Additional aspects of an exemplary processing unit 60 are now described with reference to FIG. 5. As shown, processing unit 60 may be configured to receive input data 80 from a data source 81 and output control signal 82 and/or electricity to each controller 34 via conductors 27, causing activation of one or more energy generators 31. For example, processing unit 60 of FIG. 5 includes a housing 61, a data transceiver 62, one or more processors 63, a memory 64, a communication bus 65, and a power source 66.

Data source 81 may include any combination of local and/or remote data sources. For example, source 81 may include a local sensor that is located in one of communication bays 25 and configured to send input data 80 to unit 60 using conductors 27 and/or bus 65, This configuration may allow for closed loop communications in which energy signal 90 is based on data from the local sensors. For example, the local sensor may generate the input data 80 based on chemical and/or physical outputs related to skin 2.

Data source 81 also may include a remote data source in constant communication with processing unit 60 via data transceiver 62, such as a remote sensor configured to send input data 80 to processing unit 60 with data transceiver 62 over a wired or wireless connection. This configuration may allow for open loop communications in which energy signal 90 is based on data from the local sensor and/or the remote sensor.

Any number and type of local sensors may be used to generate input data 80, and the sensor(s) may be located at any position on or relative to energy transceiver 10. In the healthcare setting, for example, one local sensor may include a personal health tracker (e.g., a Fitbit® or an iWatch®) configured to generate input data 80 based on chemical and/or physical outputs of the wearer (e.g., heart rate, temperature), and communicate input data 80 to data transceiver 62 at regular intervals (e.g., once per second or once per minute).

Housing 61 may contain the elements of processing unit 60, and/or provide a means for removing processing unit 60 from body 2, allowing for easy repairs and upgrades. As shown in FIGS. 1B and 5, for example, exterior surfaces of housing 61 may be snap-fit with interior surfaces of compartment 23 so that the distal surface of processing unit 60 is maintained against the proximal surface of compartment 23. For example, the exterior surfaces of housing 61 of may include protrusions biased outwardly along the X-X and Y-Y axes, and the interior surfaces of compartment 23 may include grooves configured to receive said protrusions.

Transceiver 62 may include any wired or wireless communication technology configured to receive input data 80 form any data source(s) 81, such as Bluetooth, Wi-Fi_33, and the like. As shown in FIG. 5, input data 80 may be generated with or stored on data source 81 and received with transceiver 62. In a healthcare setting, for example, data source 81 may include at least one patient monitoring device configured to send input data 80 to a remote server at regular intervals (e.g., once per minute). Data 80 may include various measures regarding the patient, such as body temperature, pulse rate, respiration rate, and/or blood pressure. For example, transceiver 62 may be configured to retrieve and/or receive data 80 from the remote server at regular intervals (e.g., once per second or once per minute).

Each control signal 82 may be received with input data 80. Data transceiver 62 may be configured to relay the signals 82 to the one or more processors 63 and/or memory 64. Alternatively, processing unit 60 may be configured to generate each control signal 82 based on input data 80. For example, memory 64 may include a signal generating program, and the one more processors 63 may be configured to generate each control signal 82 with the program. In keeping with previous examples, the signal generating program may be configured to: analyze the input data 80 sent from data sources 81 including a patient monitoring device during an interval; generate symbol 92A from the temperature and pulse rate, symbol 92B from the respiration rate, and symbol 92C from the blood pressure; and output a control signal 82 for communicating the symbols 92A, 92B, and 92C to skin 2.

Figure 5:
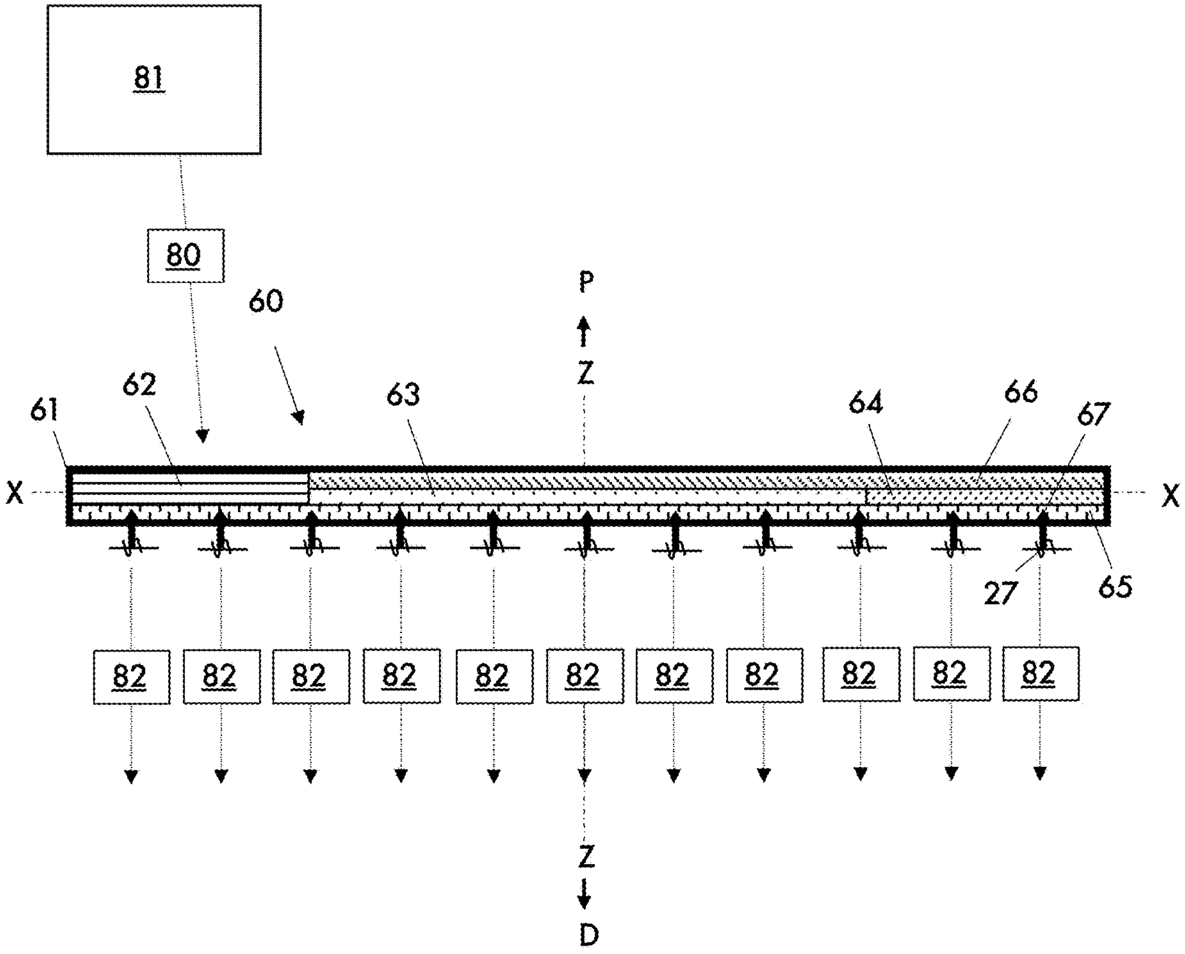
FIG. 5 depicts an exemplary processing unit.

As shown in FIG. 5, communication bus 65 may be configured to connect the one or more processors 63 and memory 64 to each generator 31, such as to each controller 34. Bus 65 may include electrical and/or optical connectors 67 located on and/or extending distally through housing 61. For example, communication bus 65 may comprise a flexible circuit board including a proximal surface supporting elements of processing unit 60, and a distal surface including an electrical and/or optical network extending from power source 66 to the connectors 67. Any type of network may be used, such as a mesh network. Connectors 67 may be engageable with corresponding connectors of conductors 27 to provide at least one pathway for outputting control signal 82 from processing unit 60 to one or more generators 31, and/or electricity from power source 66 to one or more generators 31. Control signal 82 may include electrical and/or optical signals. For example, control signal 82 may be include a string of output commands for each generator 31, and the entire string may be output to each generator 31 utilizing the electrical and/or optical signals, adding resiliency, in which the optical signals may be utilized for faster transmission.

As described above, the snap-fit connection between housing 61 and compartment 23 may place connectors 67 in communication with conductors 27, and maintain that communication over time, allowing for continuous output of control signals 82 from processing unit 60 and/or electricity from power source 66. A cover element may be attached to the proximal surface 24 of body 20 to seal processing unit 60 within compartment 23, and/or reinforce or supplant the snap-fit connection between housing 61 and compartment 23. For example, the cover may include a graphic design, a textual element, a writing surface, and/or like decorative feature. As a further example, the cover may provide a mounting surface for other technologies, such as an antenna, signal amplifier, and/or supplemental data transceiver.

Power source 66 may include any means for supplying electricity to processing unit 60 and/or the plurality of generators 31 (e.g., to each controller 34). As shown in FIG. 5, power source 66 may include a rechargeable battery, such as a lithium ion battery, chargeable by connection to an external power source, such as a wall outlet. Power source 66 may include power generation technologies. For example, a proximal surface of power source 66 may include a power generator, such as photovoltaic cells configured to charge the battery. As shown in FIG. 5, power source 66 also may include an optical energy source, such as a laser generator that is powered by power source 66 and configured to output optical energy to one or more generators 31 via optical pathways defined by communication bus 65 and conductors 27.

Aspects of attachment element 70 are now described with reference to FIG. 2C. As shown, attachment element 70 may be configured to maintain a position of tissue interface 30 against or adjacent skin 2. For example, element 70 may include an adhesive, elastic, and/or fastening element configured to apply a maintaining force in signal direction SD. In FIG. 2C, element 70 includes a proximal surface 72 adhered to the distal surface 24 of body 20, and a distal surface 74 adherable with skin 2. Distal surface 74 of element 70 may include a biocompatible adhesive configured to apply the maintaining force.

Attachment element 70 may be removably and/or semi-permanently attached to skin 2 by the biocompatible adhesive. For example, a first adhesive material may be used to attach the proximal surface 72 to distal surface 24, and a second adhesive material may be used to attach distal surface 74 to skin 2. As a further example, the first adhesive may be stronger so that energy transceiver 10 may be removed from skin 2 without separating surfaces 72 and 24. Either the first or second adhesive material may be biocompatible, and may include anti-bacterial and/or moisture resistant coatings and/or compositions configured for prolonged contact with skin 2. For example, at least the second adhesive material may be configured for contact with skin 2 during the entirety of a 4-hour, 8-hour, 12-hour, 24-hour shift, or longer shift. One or both adhesives also may be configured for semi-permanent contact with skin 2, such as during the entirety of a multi-month or multi-year treatment period. For example, at least the second adhesive material may include medicinal coatings and/or compositions that promote prolonged or semi-permanent contact with skin 2 by time-releasing treatments configured to prevent or minimize contact-based injuries.

Body 20 and/or attachment element 70 may be configured to boost the efficacy of energy signal 90 by minimizing and/or maintaining the distance between tissue interface 30 and skin 2, allowing signal 90 to be communicated with less energy. For example, any of the one or more energies 32 may be output through body 20 and/or attachment element 70. As shown in FIGS. 2B and 2C, attachment element 70 may include a plurality of openings 76. Each opening 76 may be sized approximate to one of communication bays 25, allowing the energies 32 to be output towards skin 2 in signal direction SD through openings 76. For example, each opening 76 may have an inner diameter approximate to an outer diameter of the communications bay 25 or housing 33 for each generator 31. As shown in FIG. 2C, attachment element 70 may have a thickness that allows tissue contact 39, electrical resistor 43, and/or electrical contacts 49 to contact skin 2 through opening 76 or be adjacent to skin 2 within opening 76.

Aspects of body 20 and/or attachment element 70 may direct and focus the energies 32, making it easier for the brain to distinguish one output of energies 32 from another. In keeping with previous examples, body 20 and attachment element 70 of FIGS. 2B and 2C may be composed of base materials including an impact absorbing material configured to absorb any excessive vibrations of skin 2 caused by impact energy 32A. One or both base materials may include an insulating material configured to direct heat energy 32B, electrical energy 32C, and pressure energy 32D through openings 76 along axis Z-Z; and prevent transmission of energies 32B, 32C, and 32D along axis X-X and Y-Y. For example, body 20 and element 70 of FIG. 2C may be configured to absorb any portion of energies 32 output incidentally in directions transverse to signal direction SD to promote signal distinction by limiting unwanted communications. As a further example, each opening 76 of attachment element 70 in FIG. 2C may have a reflective coating and/or a frustoconical interior shape centered about axis z-z to further focus the energies 32 towards skin 2.

As described herein, energy transceiver 10 may be operable to communicate energy signal 90 to skin 2 by outputting any energy 32, such as impact energy 32A, heat energy 32B, electrical energy 32C, and/or pressure energy 32D, individually or together. For example, any energies 32A-D may be used interchangeably or in combination to communicate any of the dots shown in FIG. 1A as symbols 92A, 92B, and 92C. As now described, aspects of each energy 32 may be modified to increase the complexity of signal 90, and thus the amount of data transmitted therewith. Modifiable aspects may include energy type, energy intensity, output duration, scroll rate, symbol shape, and the like.

Energy signal 90 may be communicated to skin 2 with energies 32, individually or together. In FIG. 1A, for example, each dot within first symbol 92A may be output with impact energy 32A; each dot within second symbol 92B may be output with heat energy 32B; and each dot within third symbol 92C may be output with electrical energy 32C. The energies 32 may be combined for additional emphasis. For example, the first symbol 92A may be output with impact energy 32A in response to a baseline measure, and output with a combination of impact energy 32A and heat energy 32B if the measure changes. The energies 32 also may be combined to enhance the penetration depth of energy signal 90. For example, first symbol 92A may be formed by first outputting pressure energy 32D to activate a portion of the nerves associated with skin 2, and second outputting heat energy 32B to the activated nerves. Any individual dot may be similarly modified relative to any other dot.

The intensity of energies 32 may be modified for emphasis. For example, processing unit 60 may be configured to output first symbol 92A with impact energy 32A at a first intensity level in response to a baseline measure, and a second intensity level to highlight signal 92A if the measure changes. Output duration may be similarly modified. For example, the output duration of energies 32 may be instantaneous for normal measures, like a quick tap (e.g., about 100 ms); extended for abnormal measures, like a short hold (e.g., 500 ms to 1 s); or a combination thereof, as with Morse code. Scroll rate may be similarly modified. For example, symbols 92 may not be scrolled at all (i.e., a scroll rate of zero), and output duration may be used to communicate change over time by flashing symbols 92 off and or in a fixed position. As a further example, in the healthcare setting, the scroll rate may be based on an update schedule (e.g., one revolution per minute), and/or the output duration may be based on patient status (e.g., faster for more critical patients).

Symbol shape also may be modified. The plurality of symbols 92 are shown as pip pattern shapes in FIG. 1A, but any symbol shape may be used, particularly those amenable to dot-matrix representation. For example, the plurality of symbols 92 may include known Morse code, binary symbols, lines, and/or directional arrows that are scrolled across communication area 4 in communication direction CD. Alphanumeric symbols also may be communicated. For example, input data 80 may include a control signal 82 generated from a Twitter® feed, and the symbols 92 may include alphanumeric symbols for communicating the author, date, and content of each Tweet® contained in the feed. As a further example, input data 80 may include the subject and sender of an email, and the signal generating program included in memory 64 may be configured to: prioritize the email based on the sender; and generate a control signal 82 for outputting a set symbols 92 based on the subject, sender, and priority of the email. For example, first symbols 92 may be output with impact energy 32A to communicate the subject and/or sender of prioritized emails in a shorthand notation, and at least one of heat energy 32B, electrical energy 32C, pressure energy 32D to communicate the priority level of the shorthand notation.

The resolution of tissue interface 30 may match or exceed the distinguishing capabilities of the nerves associated with skin 2. For example, in the grid formation shown in FIG. 2B, the resolution of tissue interface 30 may be measured as energy output per square inch, which may exceed the natural energy receptivity limits of the nerves associated with skin 2. As shown, the resolution of interface 30 may be relative to the spacing between each bay 25, the configuration of body 20 and/or attachment element 70, and/or the intensity of energies 32. The energy receptivity limits of skin 2 may vary by location. For example, energy transceiver 10 may be attached to a portion of skin 2 located in a highly innervated or sensitive area, such as the face, allowing even more complex symbol shapes to be communicated.

With sufficient resolution, tissue interface 30 may likewise be configured to output signal 90 to replicate image patterns and/or other sensory perceptions with energies 32, including any of the symbols described herein and even more complex interactions. As described herein, the multi-energy capabilities of energy transceiver 10 may be configured to layer energies 32 so as to communicate far more complex image patterns and/or sensory perceptions that would otherwise be possible by communicating with a single energy because of the natural receptivity limits of the nerves, and their tendency to become less receptive during prolonged exposures.

Figure 6A:
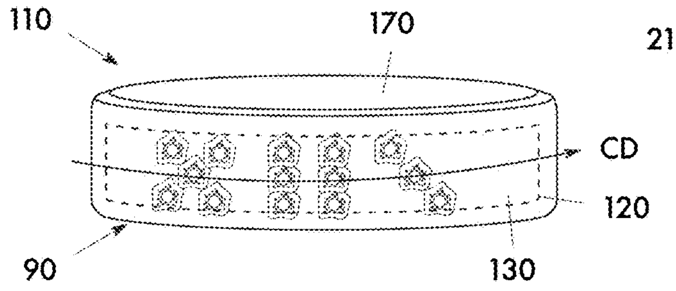
FIG. 6A depicts another exemplary communication device.

Additional aspects of this disclosure are now described with reference to numerous additional examples of energy transceiver 10, including: an exemplary energy transceiver 110 shown conceptually in FIG. 6A; an exemplary energy transceiver 210 shown conceptually in FIG. 6B; an exemplary energy transceiver 310 shown conceptually in FIG. 6C; an exemplary energy transceiver 410 shown conceptually in FIG. 6D; an exemplary energy transceiver 510 shown conceptually in FIG. 7A; an exemplary energy transceiver 610 shown conceptually in FIG. 7B; an exemplary energy transceiver 710 shown conceptually in FIG. 7C; an exemplary energy transceiver 810 shown conceptually in FIG. 7D; and an exemplary energy transceiver 910 shown conceptually in FIGS. 9A-B.

Each variation of transceiver 10, such as transceivers 110, 210, 310, 410, 510, 610, 710, 810, 910, may include elements similar to those of transceiver 10, but within the respective 100, 200, 300, 400, 500, 600, 700, 800, or 900 series of numbers, whether or not those elements are depicted in FIGS. 6A through 9B. Any aspects described with references to transceivers 110, 210, 310, 410, 510, 610, 710, 810, and 910 may be included within any variation of transceiver 10 described herein, each possible combination or iteration being part of this disclosure. For example, any variation of transceiver 10 may comprise any combination of the wearable aspects of transceivers 110, 210, 310, and 410; the contact-based aspects of transceivers 510 and 610; and the implantable aspects of transceivers 710 and 810; and/or any multi-signal aspects of transceiver 910.

Additional wearable aspects are now described with reference to FIGS. 6A-D. As shown in FIG. 6A, energy transceiver 110 may include: a body 120 and a tissue interface 130, both shown conceptually with a dotted line; and an attachment element 170, shown conceptually as a sweat band. Any type of band may be used, such as a head band, an arm band, or a bandana. Body 120 may wrap around a portion of skin 2, such as circular portion of skin 2, like around a human forearm or forehead. As shown in FIG. 6A, body 120 may be mounted on attachment element 170; and tissue interface 130 may be mounted on a distal surface of body 120. For example, body 120 may be mounted on a distal surface of element 170; and tissue interface 130 may wrap around the circular portion of skin 2 with body 120, providing a curved rectangular communication area 4 and a semi-circular (e.g., less than 360°) or circular (e.g., 360°) communication direction CD for energy signal 90.

Attachment element 170 (e.g., a sweat band) may be configured to maintain tissue interface 130 against or adjacent a portion of skin 2, such as against the arm or forehead, allowing energy signal 90 to be output in signal direction SD and/or scrolled around the head to communication are 4 in communication direction CD. For example, the band may include an elastic portion that pushes body 120 and tissue interface 130 distally toward skin 2 when placed around the circular portion of skin 2, i.e., when the sweat band of FIG. 6A is worn. As shown, the elastic portion may be proximal of energy transceiver 110, attached to a proximal surface of body 120, and configured to apply a circumferential maintaining force that maintains the position of interface 130 when element 170 is worn.

Figure 6B:
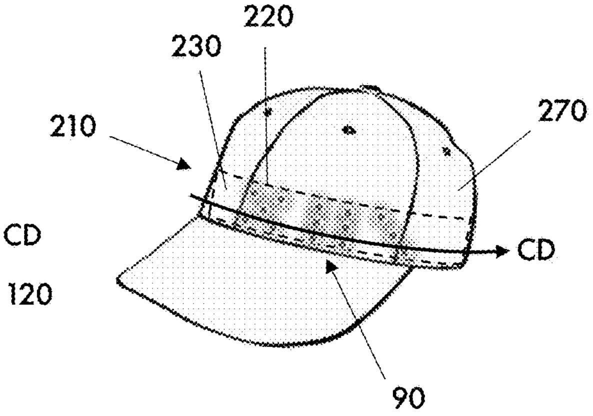
FIG. 6B depicts another exemplary communication device.

As shown in FIG. 6B, energy transceiver 210 may include: a body 220 and a tissue interface 230, both shown conceptually with a dotted line; and an attachment element 270, shown conceptually as a baseball cap. Any cap, hat, helmet, or like headwear may be used. Body 220 may wrap around a circular portion of skin 2 including the forehead and/or scalp. As shown in FIG. 6B, body 220 may be mounted on attachment element 270; and tissue interface 230 may be mounted on a distal surface of body 220. For example, body 220 may be mounted on a distal surface of element 270; and tissue interface 230 may wrap around the circular portion of skin 2 with body 220, providing a semi-circular (e.g., less than 360°) or circular (e.g., 360°) communication area 4 and communication direction CD for energy signal 90. As a further example, body 220 and tissue interface 230 may have a semi-spherical shape covering interior surfaces of cap 270 for output of energy signal 90 to a semi-spherical communication area 4 of skin 2 in any communication direction(s) CD.

Similar to attachment element 170 of FIG. 6A, attachment element 270 (e.g., a cap) also may include an elastic or non-elastic portion configured to maintain tissue interface 230 against or adjacent a portion of skin 2, such as against the forehead, allowing energy signal 90 to be output in signal direction SD and/or scrolled around the head in communication direction CD. For example, the elastic or non-elastic portion may push body 220 and tissue interface 230 distally toward skin 2 when placed around the circular portion of skin 2, i.e., when the cap of FIG. 6B is worn. As shown, the elastic or non-elastic portion may be proximal of energy transceiver 210, attached to a proximal surface of body 220, and configured to apply a circumferential maintaining force that maintains the position of interface 230 when attachment element 270 is worn. For example, the elastic or non-elastic portion may comprise a tension fastening mechanism, such any snaps, Velcro®, or other typically found on headwear.

Figure 6C:
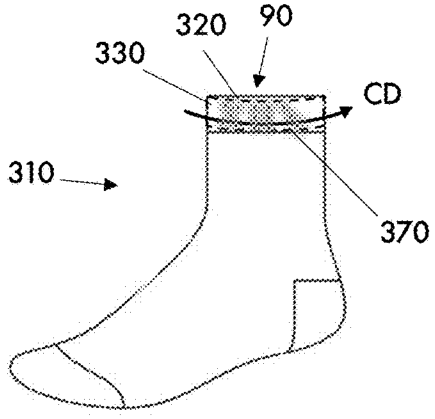
FIG. 6C depicts another exemplary communication device.

As shown in FIG. 6C, energy transceiver 310 may include a body 320 and a tissue interface 330, both shown conceptually a dotted line; and an attachment element 370, shown conceptually as a sock. Any tube-like garment may be used, including gloves, shoes, stockings, and the like. Body 320 may wrap around a circular portion of skin 2, such as around a leg. As shown in FIG. 6C, body 320 may be mounted on attachment element 370; and tissue interface 330 may be mounted on a distal surface of body 320. For example, body 320 may be mounted on a distal surface of element 370, and tissue interface 330 may wrap around the circular portion of skin 2 with body 320, providing a semi-circular (e.g., less than 360°) or circular (e.g., 360°) communication area 4 and direction(s) CD.

Similar to above, attachment element 370 (e.g., a sock) may include an elastic layer configured to maintain tissue interface 330 against or adjacent a portion of skin 2, such as against the leg, allowing energy signal 90 to be output in signal direction SD and/or scrolled around the head in communication direction CD. For example, the elastic layer may push body 320 and tissue interface 330 distally toward skin 2 when placed around the circular portion of skin 2, i.e., when the sock of FIG. 6C is worn. As before, the elastic layer may be proximal of energy transceiver 310, attached to a proximal surface of body 320, and configured to apply a circumferential maintaining force that maintains the position of interface 330 when attachment element 370 is worn.

As shown in FIG. 6C, transceiver 310 may be removably attached to attachment element 370, and thus operable with a plurality of elements 370, such as plurality of socks or other tube-like garments that typically become soiled during use. For example, element 370 may include a pouch configured to receive and secure body 320, orient tissue interface 330 toward skin 2, and/or maintain the position tissue interface 330 on or adjacent skin 2. As a further example, the elastic layer and/or the pouch may include an opening, and portions of body 320 may be engageable with (e.g., snap fit into) the opening to further maintain interface 330.

Figure 6D:
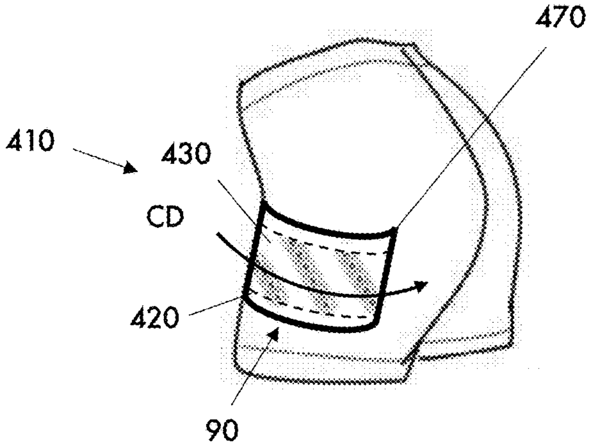
FIG. 6D depicts another exemplary communication device.

As shown in FIG. 6D, for example, energy transceiver 410 may include a body 420 and a tissue interface 430, both shown conceptually with a dotted line; and an attachment element 470, shown conceptually as a compression garment. Any type of compressive garment may be used, such as those made by Under Armour®. Body 420 of FIG. 6D may wrap around a portion of skin 2, and be composed of an impacting absorbing material (e.g., foam) configured to dissipate external impact forces directed toward the skin 2. For example, body 420 may be a thigh pad used in hockey or American football, a shin guard used in soccer, or any other type of protective pad with a distal surface that is desirably maintained against skin 2. Similar to above, body 420 may be mounted on attachment element 470; and tissue interface 430 may be mounted on a distal surface of body 420. For example, body 420 may be mounted on a distal surface of element 470; and tissue interface 430 may wrap around the circular portion of skin 2 with body 420, providing a curved communication area 4 and direction CD for signal 90.

Attachment element 470 (e.g., the compression garment) may include an elastic weave configured to maintain tissue interface 430 against or adjacent a portion of skin 2, such as against the arm or forehead, allowing energy signal 90 to be output in signal direction SD and/or scrolled around the head to communication area 4 in communication direction CD. For example, the elastic weave may push body 420 and tissue interface 430 distally toward skin 2 when placed around the circular portion of skin 2, i.e., when the compression garment of FIG. 6D is worn. In this example, the elastic weave may be attached to body 420, and configured to apply a circumferential maintaining force that maintains the position of interface 430 when attachment element 470 is worn.

Similar to above, energy transceiver 410 may be removably attached to attachment element 470, and thus operable with a plurality of elements 470, such as plurality of compressive garments. For example, impact absorbing body 420 may be mounted in a pocket of attachment element 470, and tissue interface 430 may be mounted on a distal surface of impact absorbing body 420, such as in a distal compartment of body 420. Transceiver may be a game-time accessory. For example, as shown in FIG. 6D, signals 90 may comprise a plurality of arrows scrolled along communication direction CD to communicate movements to the user. In this example, the user may be trained to move in a particular direction (e.g., left or right) and intensity (e.g., slow or fast) based on the output of energy signal 90 and the particular combination of energies 32 associated therewith.

Although not shown in FIGS. 6A-D, attachment elements 170, 270, 370, and 470 may include any adhesive and/or energy focusing elements, including those described above. For example, any aspects of attachment element 70 of FIG. 2C may be combined with any aspects of attachment elements 170, 270, 370, or 470 of FIG. 6A-D to further maintain a position of tissue interface 430 relative to skin 2 and/or focus the energies 32 according to aspects of this disclosure. Aspects of any attachment elements may be combined and operable together. For example, attachment element 470 may be include an opening, body 420 may be snapped into the opening, and a second attachment element (e.g., a biocompatible low-tack adhesive) may be configured to further fix the position of interface 430 relative to skin 2 during rigorous physical activity, such as running.

As described above, aspects of energy transceivers 110, 210, 310, and 410 may be included with any wearable item, giving aspects of this disclosure incredible breadth. For example, aspects of any of attachment elements 170, 270, 370, and 470 may be integrated into any wearable item including any type of band, strap, or like item including any combination elastic and/or non-elastic layers or portions. Exemplary attachment elements may include: bandages, wherein the tissue interface may be located on a distal surface of a skin-attachment portion; belts, wherein the tissue interface may be located on a distal surface of the belt; bras, wherein the tissue interface may be located on a distal surface of a bra strap; earrings, wherein the tissue interface may be located on a distal surface of an earring front or back; pants, wherein the tissue interface may be located on a distal surface of a waste line or seam; rings, wherein the tissue interface may be located on an interior distal surface; shirts, wherein the tissue interface may be located on a distal surface of a neckline; underwear, wherein the tissue interface may be located on a distal surface of the legs or waistline; watches, wherein the tissue interface may be located on a distal surface of the watch strap; and any known or obvious variation of the same.

Aspects of transceivers 10, 110, 210, 310, and 410 may be likewise included on any non-wearable object with a distal surface that is desirably maintained against skin 2 during use by application of an external force, such as a gravity force, a gripping force, or other externally applied maintaining force. Additional external force-based aspects are now described with reference energy transceiver 510 of FIG. 7A and energy transceiver 610 of FIG. 7B.

Figure 7A:
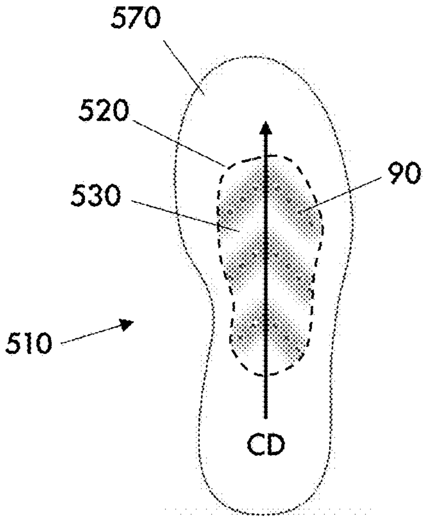
FIG. 7A depicts another exemplary communication device.

As shown in FIG. 7A, energy transceiver 510 may include: a body 520 and a tissue interface 530, both shown conceptually with a dotted line; and an attachment element 570, shown conceptually as a shoe or a shoe insert. Any type of footwear and/or foot support with equivalent surfaces may be used. Body 520 may include a surface contoured for placement against skin 2, such as an underside of a foot. As shown in FIG. 7A, body 520 may be mounted on attachment element 570; and tissue interface 530 may be mounted on or embedded in a distal portion of body 520, allowing gravity to at least partially maintain interface 530 against or adjacent skin 2, and providing a foot-shaped communication area 4 and communication direction CD for energy signal 90.

Attachment element 470 may additionally comprise any tensioning elements configured apply a maintaining force that maintains the position of interface 530 when attachment element 570 is worn, such as shoe laces, Velcro, pumping mechanisms, elastic straps or structures, and the like. As a further example, attachment element 570 may be composed of an impact absorbing material, such as a polymeric material configured to distribute forces around body 520 when walking or running; and include bolster shapes contoured to further maintain tissue interface 530 by limiting lateral movements of the foot relative thereto.

Accordingly, energy signal 90 may be communicated to the communication area 4 of skin 2 by tissue interface 530 in any communication direction CD with any combination of energies 32. As shown in FIG. 7A, energy signal 90 may include a plurality of directional shapes (e.g., the arrows of FIG. 7A) flashed and/or scrolled in a linear direction to communication directional movements. The directional shapes may be responsive to directional data. For example, transceiver 510 may be configured to receive the directional data from one or more sources (e.g., GPS signals), determine communication direction CD based on the directional data, and scroll energy signal 90 across skin 2 as directional shapes scrolling along communication direction CD to compel movement of the user in a direction.

In keeping with above, transceiver 510 also may be configured to determine an importance measure based on the directional data, and communicate energy signal 90 with a particular combination of energies 32 and/or at a particular scroll rate based on the importance measure to direct a movement aspect, such as pace or direction. In the healthcare setting, for example, the directional data may include a vital sign of a patient and the GPS location of the patient; and transceiver 510 may determine the scroll rate based on the vital sign, allowing energy signal 90 to guide a healthcare provider toward the patient at walking pace appropriate for the condition of the patent. For example, energy signal 90 may be communicated a faster scroll rate with high intensity energies 32 to alert the provider to run if needed.

Figure 7B:
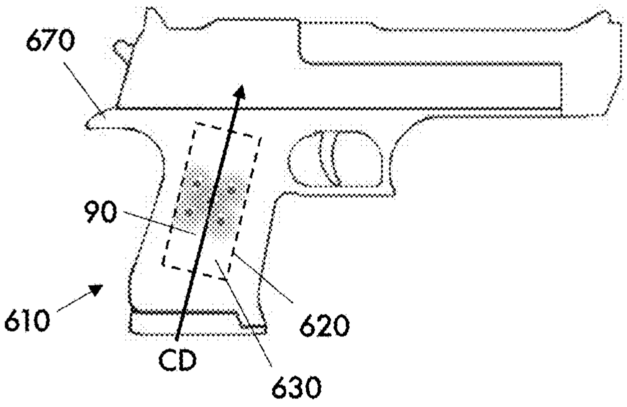
FIG. 7B depicts another exemplary communication device.
Figure 7C:
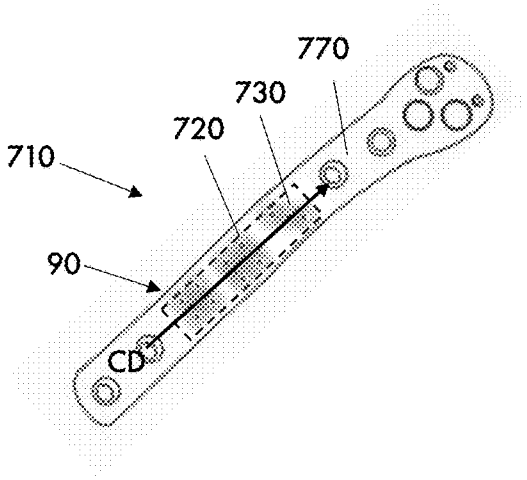
FIG. 7C depicts another exemplary communication device.

As shown in FIG. 7B, for example, energy transceiver 610 may include a body 620 and a tissue interface 630, both shown conceptually with a dotted line; and an attachment element 670, shown conceptually as a grip panel attached to the grip of a gun. Any type of gun may be used, including the handgun with a pistol grip and any other type of gun with similar surfaces that are gripped during use. In FIG. 7A, tissue interface 630 may be located on a distal surface of element 670 that is typically pushed toward a portion of skin 2 of a hand by a grip force applied by the hand during use, providing a regular or irregular shaped communication area 4. Attachment element 630 may further maintain interface 630 by limiting movements the hand. For example, element 630 may be 3D printed based on a scan of the hand to include an outwardly curving surface shaped that maintains interface 630 against skin 2 by limiting movements of the hand relative to tissue interface 430 when gripped.

Accordingly, energy signal 90 may be communicated to the communication area 4 of skin 2 by tissue interface 630 in any communication direction CD with any combination of energies 32. Aspects of energy signal 90 may be responsive to data, as with previous examples. For example, as shown in FIG. 7B, attachment element 670 (e.g., the gun) may include a sight, and energy signal 90 may include at least one decisional shape flashed and/or scrolled to communicate a status associated with gun based on a position of the sight. For example, energy transceiver 610 may include an elevation or motion sensor, and signal 90 may be output to skin 2 as a first shape (e.g., a circle) with a first energy (e.g., any combination of energies 32A-D) whenever the sensor indicates that the sight of the gun has been raised with the safety off, alerting the user to a status of the gun. As a further example, energy transceiver 10 and/or the gun may be configured to determine whether the sight is aligned with a specific target, and output signal 90 as a second shape (e.g., an X shape) with a second energy (e.g., any combination of energies 32A-D), alerting the user to a status of the target.

Any individual or combined aspects of energy transceivers 10, 110, 210, 310, 410, 510, and 610 may likewise be included on any non-wearable object with a distal surface that is desirably maintained against skin 2 during use by application of an external force, such as a gravity, a gripping force, or other externally applied maintaining force. For example, aspects of tissue interfaces 510 and 610 may likewise be included on a distal surface of any load bearing surface of any type of attachment element. For example, aspects of attachment element 570 or 670 of FIGS. 7A-B alternatively may include a bar, a chair, a handle, a floor, a rope, a wall, or any like object with a skin facing surface that is generally maintained against skin 2 during use; and aspects of issue interfaces 530 or 630 of FIGS. 7A-B alternatively may be mounted therewith so that energy signal 90 may be output to skin 2 whenever the alternative attachment element 570 or 670 is used.

Additional implantable aspects are now described with reference to energy transceiver 710 of FIG. 7C and energy transceiver 810 of FIG. 7D. As shown in FIG. 7C, for example, energy transceiver 710 may include a body 720 and a tissue interface 730, both shown conceptually with a dotted line; and an attachment element 770, shown conceptually as a portion of a bone plate. Any type of bone plate or other implantable object may be used. Attachment element 770 of FIG. 7C includes a proximal bone-facing surface and a distal skin-facing surface. The bone-facing surface may be maintained against the bone by any combination of adhesives, screws, wires, and/or other bone fixation technologies. The skin-facing surface may maintain the position of tissue interface 730 relative to the bone, allowing for movement of skin 2 relative to interface 730. For example, tissue interface 730 may be mounted in a compartment on the skin-facing surface.

As above, energy signal 90 may be communicated to the communication area 4 of skin 2 by tissue interface 730 in any communication direction CD with any combination of energies 32. As shown in FIG. 7C, signal 90 may include any combination of shapes moving in any communication direction CD, including any combination of shapes and/or directions, any of which may be flashed and/or scrolled with any energies 32. In contrast to above, energy signal 90 of FIG. 7C may be output toward the underside of skin 2, allowing for more direct communication with nerves associated with skin 2. Aspects of transceiver 710 and energy signal 90 may be modified according to the implanted location of attachment element 770. For example, tissue interface 730 may be embedded in an attachment element 770 sized for placement against a radius or finger bone wherein the distance between skin 2 and bone is minimal, allowing signal 90 to be communicated with less energy. As a further example, interface 730 may be mounted on an attachment element 770 sized for placement against a radius or ulna, wherein the distance between skin 2 and the bone is larger.

Similar to above, aspects of body 720 and/or attachment element 770 may direct and focus the energies 32, making it easier to distinguish one output of energies 32 from another and/or prevent the energies 32 from being output to bone. Alternatively, all or portion of the energies 32 may be output toward the bone-facing surface of element 770 to communicate signals and/or apply treatments to the bone. For example, the energies 32 may be output through body 720 and/or attachment element 770 in a proximal and/or distal direction, such as through a plurality of openings extending through element 770. As a further example, the distal surface of body 720 may include a first tissue interface 730 and/or the bone-facing surface of body 730 may include a second tissue interface 730, allowing a corresponding set of first and/or second energy signals 90 to be toward in a first direction toward skin 2 and/or a second direction toward the bone.

Figure 7D:
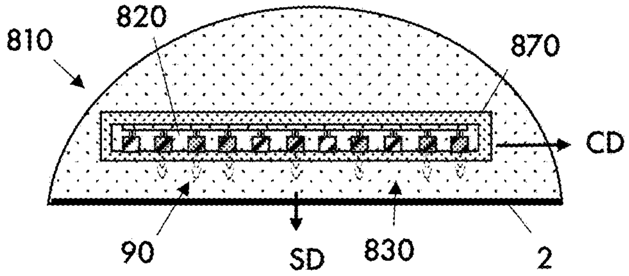
FIG. 7D depicts another exemplary communication device.

As shown in FIG. 7D, for example, energy transceiver 810 may include a body 820 and a tissue interface 830, both shown conceptually with a dotted line; and an attachment element 870, shown as a biocompatible outer surface layer surrounding body 820. Any type of biocompatible material or containing structure may be used. In this example, attachment element 870 may comprise a tissue in-growth promoting exterior layer that maintains the orientation and/or position of tissue interface 30 over time by interacting with living tissue. For example, element 870 may be composed of a polymeric material, such as a variant of polyether ether ketone (or "PEEK"); and/or include an outer surface textured to promote tissue ingrowth.

Energy signal 90 may be output from tissue interface 830 as above. As shown in FIG. 7D, tissue interface 830 may be oriented so that the signals 90 are output through attachment element 870 and toward a communication area 4 under skin 2 in a signal direction SD. For example, aspects of body 820 and/or attachment element 870 may direct and focus the energies 32 toward discrete areas 4 on the underside of skin 2, making it easier for the brain to distinguish one output of energies 32 from another and/or preventing the energies 32 from being output other living portions, such as bone or muscle. Alternatively, all or portion of the energies 32 may be output simultaneously from proximal and distal sides of element 870 to communicate with nerves associated with skin 2 and the other living portions. For example, the energies 32 may be output through body 820 and/or attachment element 870 in either direction through a plurality of openings extending therethrough. Also similar to above, transceiver 810 may include a first interface 830 disposed opposite a second interface 830, allowing for output of a corresponding set of first and second energy signals 90.

Figure 8A:
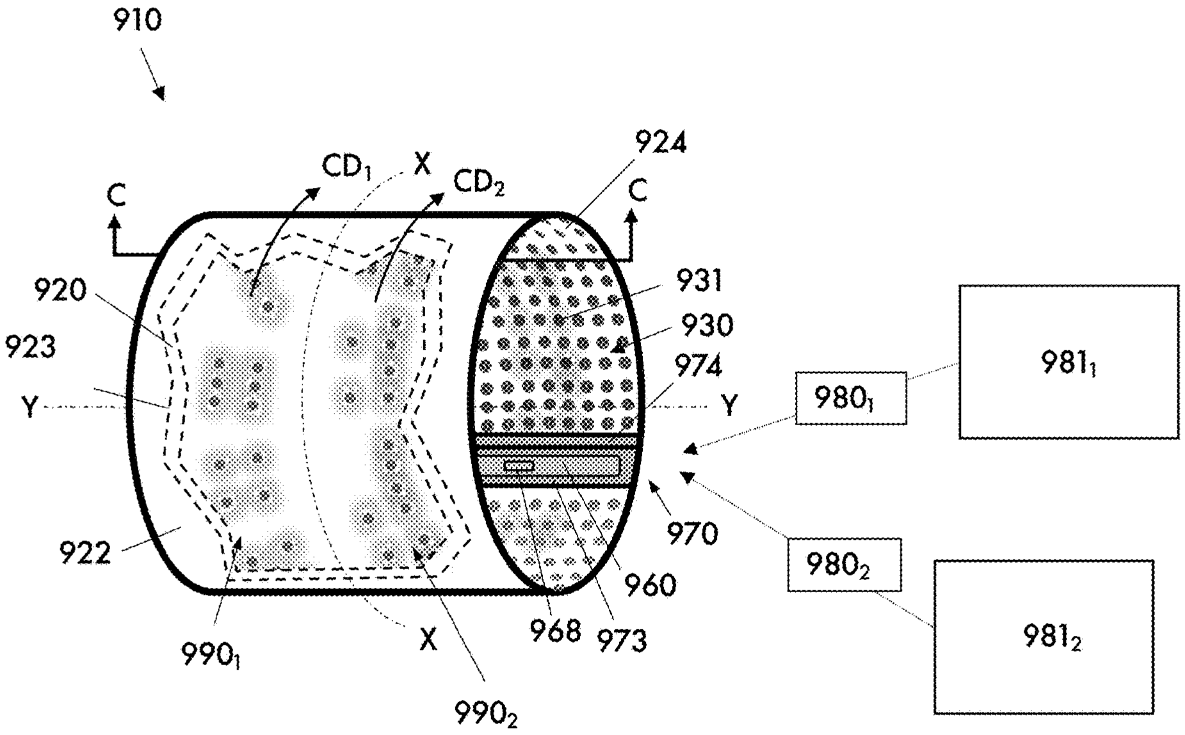
FIG. 8A depicts another exemplary communication device.

Additional aspects are now described with reference to energy transceiver 910 of FIGS. 8A and 8D, demonstrating that any variation of transceiver 10 described herein may be configured to output a plurality of signals 90. For example, energy transceiver 910 may be configured to output a plurality of energy signals 90 in a signal direction SD toward skin 2. As shown in in FIGS. 8A and 8B, transceiver 910 may output a first signal $\mathbf{990}_1$ in a first divided area or band $\mathbf{924}_1$, and a second signal $\mathbf{990}_2$ in a second divided area or band $\mathbf{924}_2$. Each signal $\mathbf{990}_1$ and $\mathbf{990}_2$ may include a plurality of symbols. In FIG. 8A, for example, the symbols include dots made visible through an exemplary cut-out in transceiver 910 as they would be communicated to skin 2, similar to FIG. 1A. Likewise, some of the generators 931 are shaded in FIG. 8A indicate output of energies 32, similar to FIG. 2B.

Figure 8B:
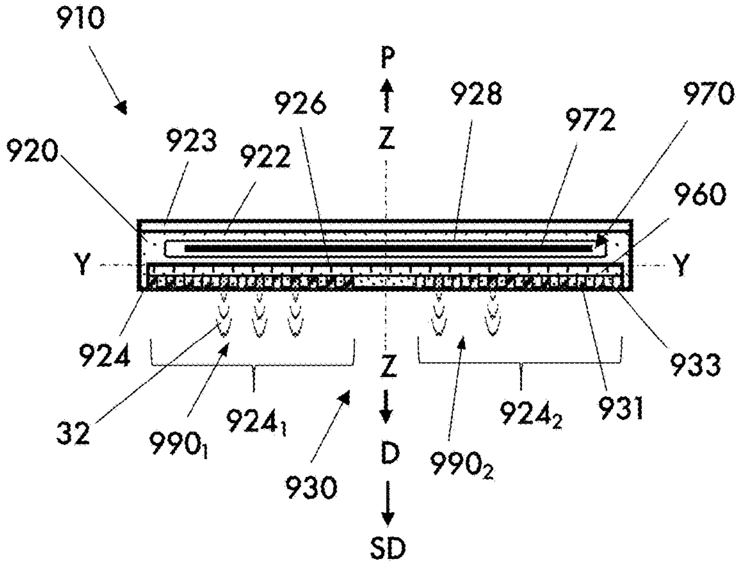
FIG. 8B depicts a cross-section view of the FIG. 8A device.

Transceiver 910 may comprise: a body 920; a tissue interface 930; a processing unit 960; and an attachment element 970. Similar to above, body 920 may contain elements of transceiver 10 within a flexible biocompatible base material that is conformable against skin 2, and maintainable against skin 2 for prolonged and/or semi-permanent durations. As shown in FIGS. 8A and 8B, body 920 may have a length extending along a longitudinal axis X-X, a width extending along a lateral axis Y-Y, and a thickness extending along a proximal-distal axis Z-Z, similar to body 20 of FIGS. 2A-C. The length, width, and/or thickness of body 920 may be compatible with a curved portion of skin 2, as in FIG. 8A, where body 920 is curved along axis X-X. For example, body 920 may be curved and/or wrapped around any body shape, such as a human forearm, a human shin, and/or portions of a human torso.

As also shown in FIGS. 8A and 8B, body 920 may define a proximal surface 922, a distal surface 924, a distal compartment 926, and an interior conduit 928. The proximal surface 922 may include a cover 923 mounted thereto. Cover 923 may include a graphic design, a textual element, a writing surface, and/or like decorative feature. As shown in FIG. 8B, a distal surface of cover 923 may include a first attachment element (e.g., a first Velcro strip) engageable with a second attachment element (e.g., a second Velcro strip) on the proximal surface 922, allowing cover 923 to be switched-out as needed. The second attachment element also may attach body 920 to another object such as the inside of a garment.

Tissue interface 930 may be similar to any variation of tissue interface 30 described herein. As shown in FIG. 8B, tissue interface surface 930 may be mounted in the distal compartment 926 of body 920, and include plurality of energy generators 931 directed toward skin 2. Each generator 931 may be similar to generators 31 described above. For example, each generator 931 may be operable with processing unit 960 to output energies 32 individually and/or in combination in a signal direction SD; and contained with base material 933 (e.g., epoxy) that directs and/or focusses energies 32 in the signal direction SD. Each generator 931 may likewise include a plurality of generator elements arranged (e.g., coaxially) to output their respective energies 32 in approximately the same direction along an axis z-z, making the outputs interchangeable. As before, the energies 32 may include impact energy 32A (e.g., FIG. 4A), heat energy 32B (e.g., FIG. 4B), shock energy 32C (e.g., FIG. 4C), pressure energy 32D (e.g., FIG. 4D); and/or any like energies.

In contrast to above, the plurality of generators 931 may be arranged into a plurality of divided areas or bands. As shown in FIG. 8B, the width of body 920 along lateral axis Y-Y may include the first band $\mathbf{924}_1$ of generators 931, which may extend around the length of body 920 along a first longitudinal axis $X_1$-$X_1$ of transceiver 910; and the second band $\mathbf{924}_2$ of generators 931, which may extend around the length of body 20 along a second longitudinal axis $X_2$-$X_2$. The generators 931 located in first band $\mathbf{924}_1$ may be configured to output first signal $\mathbf{990}_1$, and the generators 931 located in second band $\mathbf{924}_2$ may be configured to output second signal $\mathbf{990}_2$. To enhance distinguishability, an interior portion of compartment 926 and/or base material 933 may physically separate first band $\mathbf{924}_1$ from second band $\mathbf{924}_2$, as in FIG. 8B.

As shown in FIG. 8A, processing unit 960 may be configured to: receive first input data 980A from a first data source 981A; receive second input data 980B from a second data source 981B; and output a control signal 982 and/or to electricity to generators 931, causing various combinations of said generators 931 to output first signal $\mathbf{990}_1$ and second signal $\mathbf{990}_2$. For example, processing unit 960 of FIGS. 8A and 8B may include any elements of processor 60 of FIG. 5, such as transceiver 62, one or more processors 63, memory 64, communication bus 65, and power source 66. Each of these elements may perform a similar function within processing unit 960. Similar to above, one or more wired and/or wireless connections (e.g., such as conductors 27) may extend between processing unit 960 and each generator 931.

Attachment element 970 may maintain a position of tissue interface 930 against or adjacent skin 2. As shown in FIG. 8B, attachment element 970 may be proximal of tissue interface 930, and configured to maintain the position of interface 930 by applying a distally-directed force to body 920. The distally-directed force may press tissue interface 930 against skin 2, and/or cause portions of interface 930 to conform against a curvature of skin 2. As also shown in FIG. 8B, attachment element 970 may include a strap 972 extending through an interior conduct 928 of body 920. Strap 972 may apply the distally-directed force. For example, strap 972 may be composed of a resilient material (e.g., metal) having a cross-sectional shape (e.g., a semi-circular shape) that maintains body 920 in either an elongated configuration (e.g., FIGS. 2A-C) or a curved configuration (e.g., FIG. 8A), like a slap bracelet.

Attachment element 970 also may apply the distally-directed force by applying a tensile force to strap 972. As shown in FIG. 8A, a first end 973 of strap 972 may extend from one end of conduit 928, a second end 977 of strap 972 may extend from another end of conduit 928, and the tensile force may be imparted by removably attaching ends 973 and 974. For example, a proximal surface of the first end 973 may include a first attachment element (e.g., a first Velcro strip), a distal surface of second end 974 may include a second attachment element (e.g., a second Velcro strip), and the first and second attachment elements may be overlapped to impart the tensile force. Any type of attachment element may be used to attached ends 973 and 974, including buckles, ratchets, and the like. In some aspects, band 972 may be an elastic band, and ends 973 and 974 may be permanently attached together.

Processing unit 960 may be removably attached to transceiver 910, allowing for easy repairs and upgrades. As shown in FIG. 8A, processing unit 960 may be attached to a distal surface of the first end 973 of strap 972, and connected to tissue interface 930 by one or more conductors. For example, similar to conductors 27 described above, the conductors may include a network that is located in distal compartment 926 with tissue interface 930, and configured to transmit power and/or control signals between processing unit 960 and generators 931. As shown in FIG. 8A, a distal surface of processing unit 960 may include one or more sensors 968, and attachment element 970 may be configured to maintain a position of the one or more sensors 968 one or adjacent to skin 2, allowing characteristics of the user to be monitored and/or output with processing unit 960.

Signals $\mathbf{990}_1$ and $\mathbf{990}_2$ may be similar to signal 90 of FIG. 1A. For example, first signal $\mathbf{990}_1$ may include a plurality of first symbols output in first band $\mathbf{924}_1$, and second signal $\mathbf{990}_2$ may include a plurality of second symbols output in second band $924_2$. As shown in FIGS. 8A and 8B, each of first and second symbols and/or dot may be associated with different data. For example, in the healthcare setting, first signal $990_1$ may include first symbols associated with a first patient, and each first symbol may be associated with a vital sign for the first patient; whereas second signal $990_2$ may include second symbols associated with a second patient, and each second symbol may be associated with a vital sign for the second patient, allowing the user to simultaneously monitor the first and second patients with transceiver 910.

As shown in FIG. 8A, first signal $990_1$ may be scrolled around first band $924_1$ by outputting energies 32 toward skin 2 in signal direction SD, and moving the output across skin 2 in a first communication direction $CD_1$; and second signal $990_2$ may be scrolled around second band $924_2$ by outputting energies 32 toward skin 2 in signal direction SD, and moving the output across skin 2 in a second communication direction $CD_2$. Each signal $990_1$ and $990_2$, and/or each first or second symbol included therein, may be configured for increased complexity, allowing more data to be transmitted therewith. In keeping with the previous healthcare example, each signal $990_1$ and $990_2$ may be scrolled in one of communication directions $CD_1$ or $CD_2$ at a scroll rate associated with a vital sign of the respective first and second patients (e.g., pulse rate); each first and second symbol may be associated with another vital sign for said first and second patients (e.g., body temperature, pulse rate, respiration rate, and/or blood pressure); and the first and second symbols may be output with different combinations of energies 32 to communicate different aspects the vital signals (e.g., an increase or decrease in body temperature, pulse rate, respiration rate, and/or blood pressure).

Although shown as having two divided areas (e.g., first band $924_1$ and second band $924_2$) configured to output two different energy signals (e.g., first signal $990_1$ and second signal $990_2$), transceiver 910 may include any number of divided areas having any shape. For example, the width of body 920 may accommodate a plurality of divided areas, at least one tissue interface 930 may be located in each divide area, and attachment element 970 may be configured to maintain each tissue interface 930 against a different portion of skin 2. For example, body 920 of FIG. 8A may accommodate a plurality of bands spaced apart along a length of a limb (e.g., a forearm), and each band (e.g., similar to bands $924_1$ and $924_2$) may output a different energy signal (e.g., similar to signals $990_1$ and $990_2$) based on input data from a different data source (e.g., similar to sources $981_1$ and $981_2$). In a healthcare setting, each data source may include a patient monitoring device, allowing the user to simultaneously monitor a plurality of different patients with transceiver 910.

Various methods associated with transceiver 10 are now described, including methods of operating transceiver 10. Aspects of each method may be used with any variation of transceiver 10 described herein, such as transceivers 110, 210, 310, 410, 510, 610, 710, 810, and 910 described above. For ease of description, aspects these methods are now described with various references to these exemplary transceivers, including numerous references to energy transceiver 10. Unless claimed, these references are exemplary and non-limiting.

Figure 9:
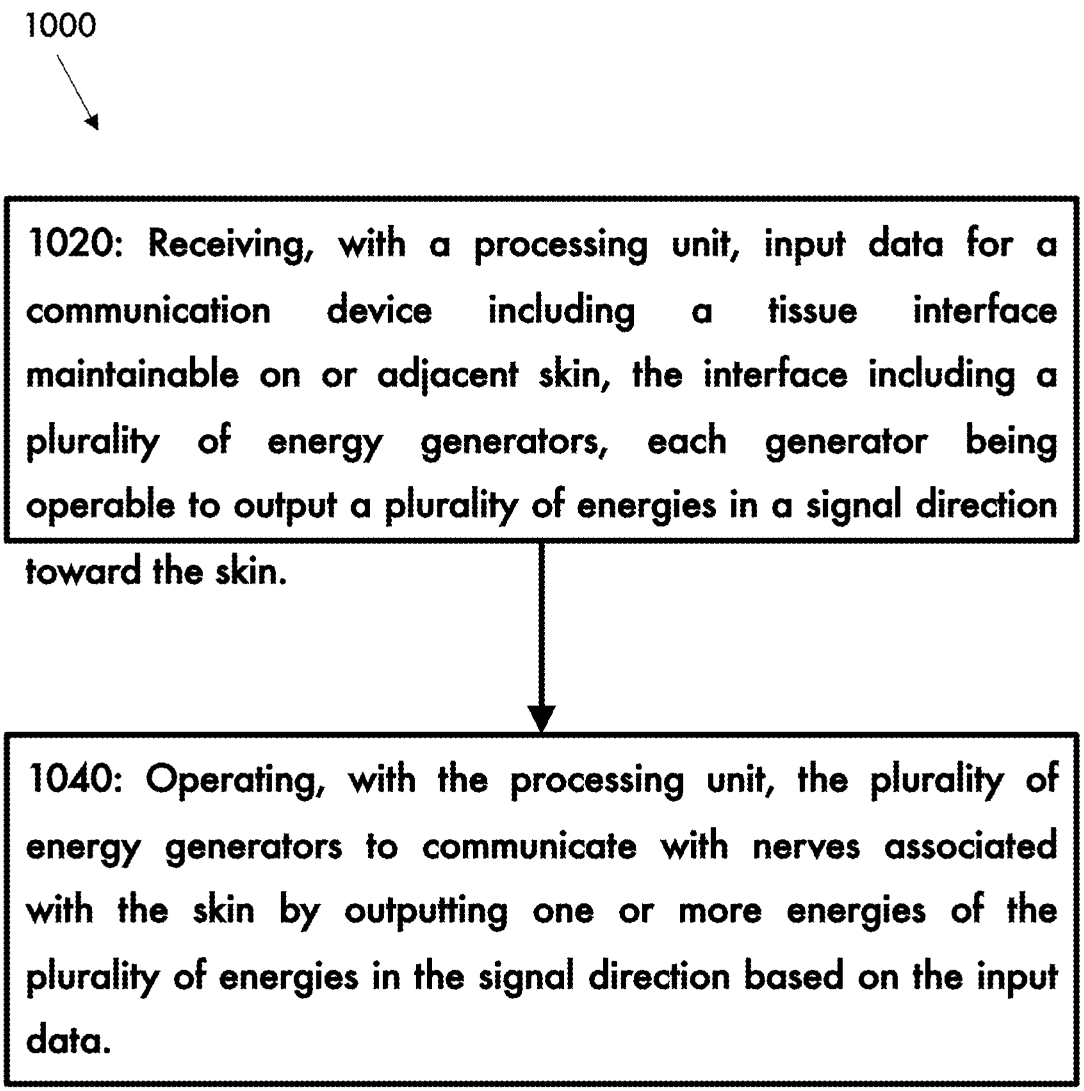
FIG. 9 depicts an exemplary method.

As shown in FIG. 9, an exemplary method 1000 may comprise: receiving, with processing unit 60, input data 80 for a communication device 10 including a tissue interface 30 maintainable on or adjacent skin 2, the interface 30 including a plurality of energy generators 31, each generator 31 being operable to output a plurality of energies 32 in a signal direction SD toward skin 2 (a receiving step 1020); and operating, with processing unit 60, the plurality of energy generators 31 to communicate with nerves associated with the skin 2 by outputting one or more energies (e.g., any of energies 32A, 32B, 32C, and 32D) of the plurality of energies 32 in the signal direction SD based on input data 80 (an operating step 1040).

Receiving step 1020 may comprise receiving input data 80 from one or more data sources 81. For example, the one or more data sources 81 may include at least one of patient monitoring device, a remote server, and a sensor. In this example, receiving step 1020 may comprise receiving input data 80 from the one or more data sources 81 at regular intervals, and operating step 1040 may comprise outputting the one or more energies based on the input data 80 received during each regular interval.

Input data 80 may include a control signal 80, and operating step 1040 may comprise outputting the one or more energies based on the control signal 82. Alternatively, method 1000 may comprise: generating, with processing unit 60, control signal 82 based on input data 80, wherein operating step 1040 may comprise outputting the one or more energies based on control signal 82. For example, the generating step 1030 may include associating the input data 80 with a plurality of symbols 92, and operating step 1040 may comprise communicating the symbols 92 with the one or more energies. In this example, the input data 80 may include measurements (e.g., vital signs of a patient), and each symbol may be associated with one or more of the measurements (e.g., one or more of the vital signs).

In any of these examples, the one or more energies may include a first combination of the plurality of energies 32 (e.g., impact energy 32A and pressure energy 32D); and a second combination of the plurality of energies 32 (e.g., heat energy 32B and pressure energy 32D). The first combination may be followed by any second combination(s). For example, the one or more energies may include a first energy (e.g., impact energy 32A) communicable with a first portion of the nerves (e.g., Meissner's corpuscle); and a second energy (e.g., heat energy 32D) communication with a second portion of the nerves (e.g., the Ruffini corpuscle).

Operating step 1040 may alternatively comprise: operating, with processing unit 60, the plurality of energy generators 31 to communicate energy signal 90 to nerves associated with the skin 2 by outputting one or more energies of the plurality of energies 32 in signal direction SD based on input data 80. For example, step 1040 may comprise outputting different combinations of the one or more energies, and each different combination may communicate a different portion of the energy signal 90. Similar to above, energy signal 90 may include one or more symbols 92, and operating step 1040 may comprise outputting the one or more energies to communicate the one or more symbols 92. Step 1040 may comprise scrolling the one or more symbols 92 across skin 2 in a communication direction CD transverse with the signal direction SD; and/or flashing any of symbols 92 on-and-off. The plurality symbols 92 may include any type of signal, including pip patters, alphanumeric symbols, and the like.

Various energy types may be used. For example, operating step 1040 may comprise outputting a first combination of the one or more energies to communicate a first symbol of the one or more symbols (e.g., symbol 92A), and outputting a second combination of the one or more energies to communicate a second symbol of the one or more symbols (e.g., symbol 92B). In some aspects, operating step 1040 may comprise: outputting a first combination of the one or more energies to communicate energy signal 90 and outputting a second combination of the one or more energies to communicate a characteristic of energy signal 90, so as to highlight energy signal 90 or a portion thereof. Input data 80 may include a measurement, and step 1040 may comprise outputting a first combination of the one or more energies based on the measurement. In this example, step 1040 may comprise modifying the first combination based on a change of the measurement, and/or outputting a second combination of the one or more energies based on the change of the measurement.

Figure 10:
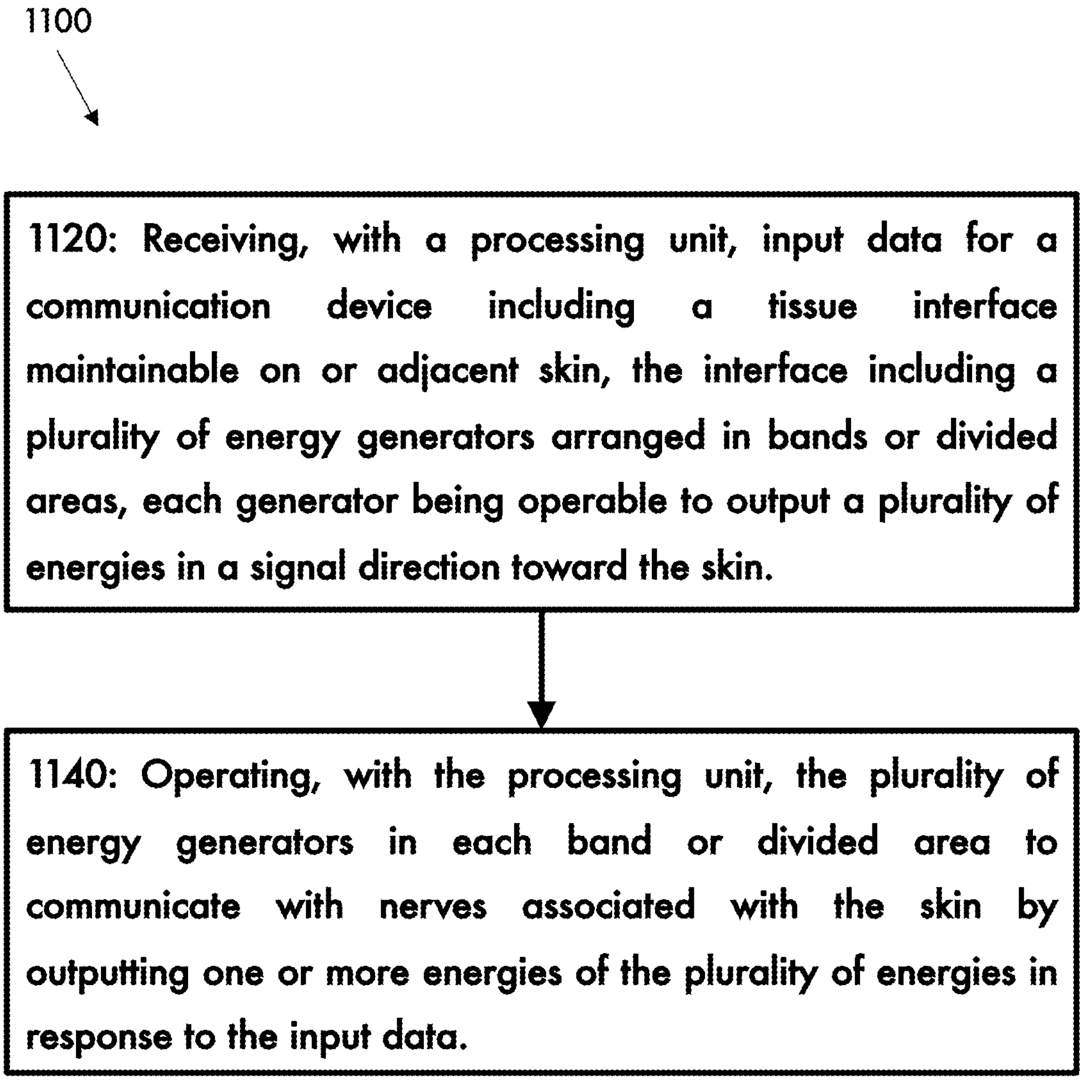
FIG. 10 depicts another exemplary method.

The larger size of transceiver 910 relative to transceivers 10 may allow for different methods of operation. As shown in FIG. 10, for example, an exemplary method 1100 may comprise: receiving, with processing unit 960, input data 980 for a communication device 910 including a tissue interface 930 maintainable on or adjacent skin 2, the interface 930 including a plurality of energy generators 931 arranged in bands $\mathbf{924}_1$ and $\mathbf{924}_2$, each generator 931 being operable to output a plurality of energies 32 in a signal direction SD toward the skin 2 (a receiving step 1120); and operating, with processing unit 60, the plurality of energy generators 931 in each band $\mathbf{924}_1$ and $\mathbf{924}_2$ to communicate with nerves associated with the skin 2 by outputting one or more energies of the plurality of energies 32 in response to the input data 80 (an operating step 1140).

Receiving step 1020 may comprise receiving input data 980 from one or more data sources 981. As shown in FIG. 10, for example, step 1020 may comprise receiving a first input data 980A from a first data source 981A, and a second input data 980B from a second data source 981B. Input data 980 may include a plurality of measurements. Accordingly, receiving step 1020 may comprise receiving input data include a plurality of measurements; and operating step 1040 may comprise operating the plurality of energy generators 931 in each band $\mathbf{924}_1$ and/or $\mathbf{924}_2$ to output the one or more energies based on one measurement of the plurality of measurements.

In the healthcare setting, first data source 981A may include a patient monitoring device or sensor configured to output measurements associated with a first patient, and second data source 981AB may include a patient monitoring device or sensor configured to output measurements associated with a second patient. The measurements may include vital signs for the respective first and second patients. In this example, receiving step 1120 may comprise receiving input data 980 including a plurality of vital signs; and operating step 1140 may comprise operating the plurality of energy generators 931 in each band $\mathbf{924}_1$ and $\mathbf{924}_2$ to output the one or more energies based on one vital sign of the plurality of vital signs. For example, step 1140 may comprise operating the generators 931 in band $\mathbf{924}_1$ to output energies 32 based on the vital signs for the first patient, and/or operating the generators 931 in band $\mathbf{924}_2$ to output energies 32 based on the vital signs for the second patient.

Aspects of energies 32 may be modified based on the measurements. For example, operating step 1040 may comprise: outputting a first combination of energies 32 when the at least one of the measurements is inside of an acceptable range; and outputting a second combination of energies 32 when at least one of the measurements is outside of the acceptable range. In the healthcare setting, one of the vital signs of the patient (e.g., pulse rate) may serve as the baseline measure.

Similar to above, input data 980 may include a control signal for each band $\mathbf{924}_1$ and $\mathbf{924}_2$, and operating step 1140 may comprise outputting the energies 32 based on the control signal for each band $\mathbf{924}_1$ or $\mathbf{924}_2$. Alternatively, method 1100 may further comprise: generating, with the processing unit 960, a control signal for each band $\mathbf{924}_1$ and $\mathbf{924}_2$ based on input data 980, wherein the operating step 1140 comprises outputting the energies 32 based on the control signal for each band.

Also similar to above, operating step 1140 also may comprise operating the plurality of energy generators 931 to simultaneously communicate a plurality of energy signals to nerves associated with the skin 2 by outputting an energy signal in each band with energies 32, and/or scrolling the energy signal in its respective band. As shown in FIG. 10, step 1140 may comprise outputting first energy signal $\mathbf{990}_1$ in first band $\mathbf{924}_1$ with a first combination of energies 32, and outputting second energy signal $\mathbf{990}_2$ in second band $\mathbf{924}_2$ with a second combination of energies 32. Each signal $\mathbf{990}_1$ and $\mathbf{990}_2$ may include a plurality of symbols (e.g., symbols 92), and operating step 1140 may comprise scrolling the symbols across one of bands $\mathbf{924}_1$ and $\mathbf{924}_2$. In keeping with above, first signal $\mathbf{990}_1$ (and any symbols contained therein) may be scrolled along a first communication direction $CD_1$ transverse with signal direction SD, and second signal $\mathbf{990}_2$ (and any symbols contained therein) may be scrolled along a second communication direction $CD_2$ transverse with signal direction SD.

Although described with reference to two divided areas (e.g., first band $\mathbf{924}_1$ and second band $\mathbf{924}_2$) configured to output two energy signals (e.g., first signal $\mathbf{990}_1$ and second signal $\mathbf{990}_2$), it is contemplated that method 1100 may be configured for any number of divided areas. Accordingly, variations of method 1100 may allow the user to simultaneously monitor a plurality of sources of input data, from one or more data sources, with aspects of transceiver 910 described herein.

Figure 11:
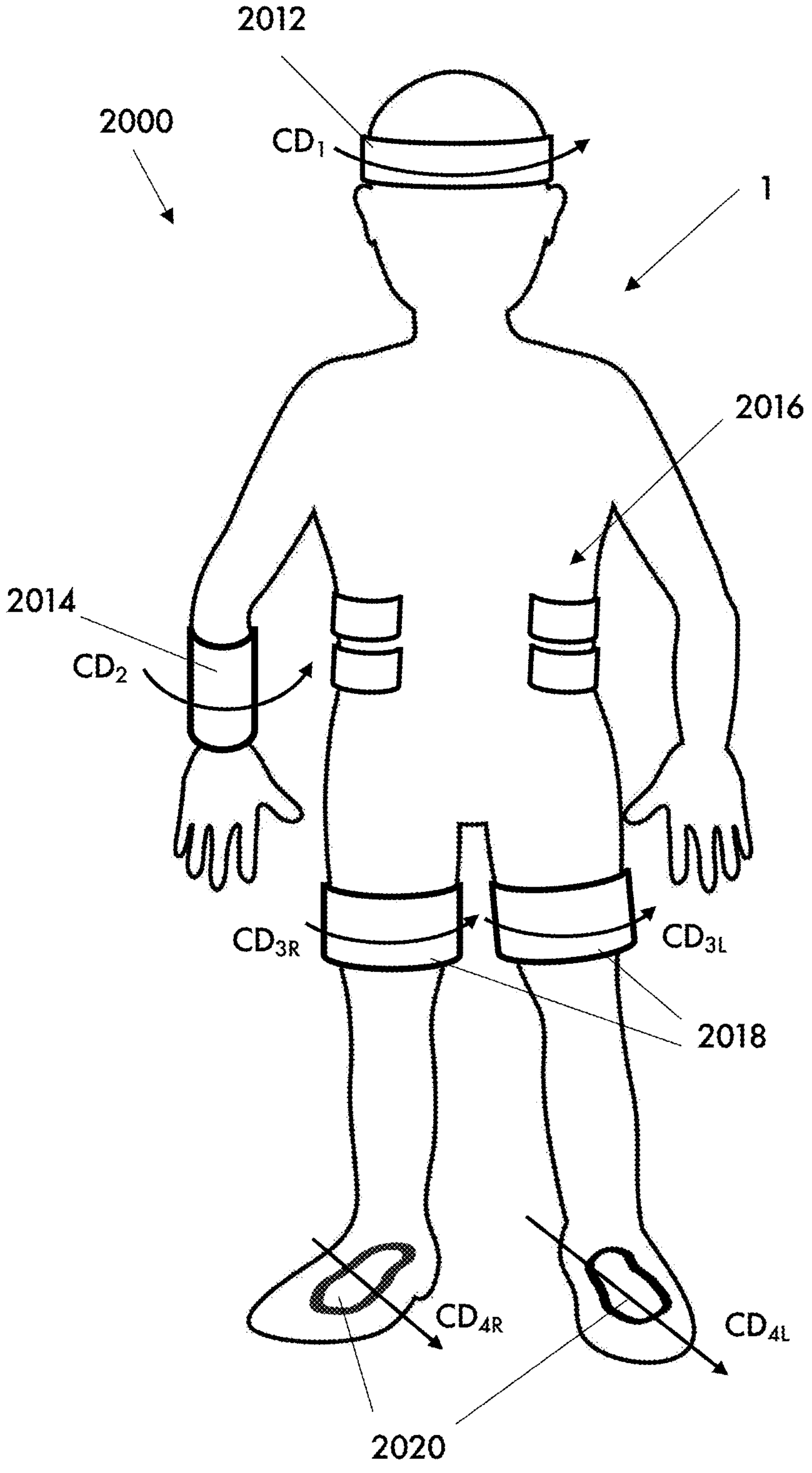
FIG. 11 depicts an exemplary communication system.
Figure 12:
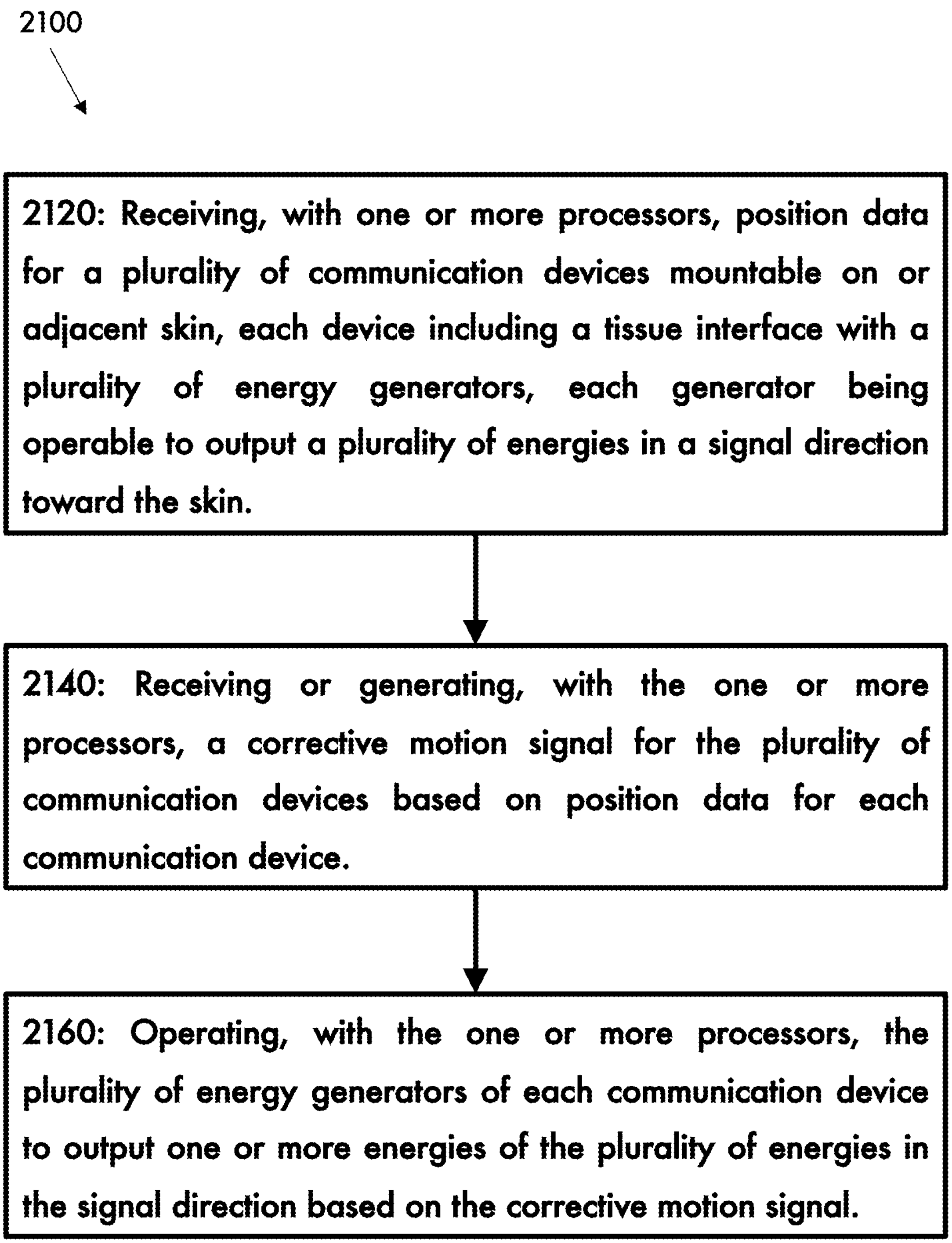
FIG. 12 depicts another exemplary method.

Additional aspects described above with reference to transceivers 10, 110, 210, 310, 410, 510, 610, 710, 810 and 910, and methods 1000 and 1100, are now described with reference to a communication system 2000. Aspects of an exemplary system 2000 are depicted in FIGS. 11 and 12. As shown in FIG. 11, communication system 2000 may comprise a plurality of energy transceivers configured to receive input data and output one or more of a plurality of energies 32 to different locations of skin 2 according to the input data. Each transceiver may include any element and perform any function described above with reference to transceivers 10, 110, 210, 310, 410, 510, 610, 710, 810 and 910, and methods 1000 and 1100. Different aspects may be combined in system 2000. For example, as shown in FIG. 11, system 2000 may comprise: a first energy transceiver 2012 on a head of a user 1, similar to transceiver 110 of FIG. 6A; a second energy transceiver 2014 on one arm of user 1, similar to transceiver 900 of FIGS. 9A-B; a plurality of energy transceivers 2016 attached to a torso of user 1, similar to transceiver 10 of FIGS. 2A-C; an energy transceiver 2018 on each leg of user 1, similar to transceiver 410 of FIG. 6D; and an energy transceiver 2020 in each shoe of user 1, similar to transceiver 510 of FIG. 7A.

Each transceiver 2012, 2014, 2016, 2018, and 2020 may be interconnected in system 2000 so that coordinated control signals may be output to each transceiver for output of a corresponding signal 90 with a corresponding one or more of energies 32. The coordinated control signals may be used to coordinate activities or movements of user 1 in response to the input data. As shown in FIG. 11, each of said transceivers may output data associated with a first form or position of user 1, receive input data regarding a second form or position, and output signals 90 in the same or communication directions CD to direct the user 1 to move according to the desired form or position. In one aspect, the first form or position may be a first pose or stance, and the second form or position may be a second pose; in other aspects, the first form or position may be a first (e.g., GPS) position on a field, and the second form or position may be a second (e.g., GPS) position on the field.

As shown in FIG. 11, for example, transceiver 2012 may scroll a first signal 90 in a first communication direction $CD_1$ around the head; transceiver 2014 may scroll a second signal 90 around the arm in a second communication direction $CD_2$; transceivers 2016 may output third signals 90 without scrolling; transceivers 2018 may scroll fourth signals 90 in communication directions $CD_{3R}$ and $CD_{3L}$ around the legs; transceivers 2020 may scroll fourth signals 90 in communication directions $CD_{4R}$ and $CD_{4L}$ across the feet. Accordingly, each of the respective signals and communication directions may be coordinated in system 2000 to direct the user to move in a particular direction and/or move one or more of their limbs into a particular form or position.

Aspects of methods 1000 and 1100 may be modified for use within system 2000. As shown in FIG. 12, for example, an exemplary method 2100 may comprise: receiving, with one or more processors, position data for a plurality of communication devices (e.g., transceivers 2012, 2014, 2016, 2018, 2020) mountable on or adjacent skin, each device including a tissue interface with a plurality of energy generators 31, each generator 31 being operable to output a plurality of energies 32 in a signal direction SD toward skin 2 (a "receiving step 2120"); receiving or generating, with the one or more processors, a corrective motion signal for the plurality of communication devices based on position data for each communication device (a "receiving or generating step 2140"); and operating, with the one or more processors, the plurality of energy generators 31 of each communication device to output one or more energies of the plurality of energies 32 in signal direction SD based on the corrective motion signal. Although described with reference to elements of transceiver 10, method 2100 may be performed with any transceiver described herein.

Additional aspects described above with reference to transceivers 10, 110, 210, 310, 410, 510, 610, 710, 810 and 910, methods 1000 and 1100, system 2000, and method 2100 are now described with reference to aspects of an energy transceiver 3010 shown in FIGS. 13A, 13B, 14A, and 14B. As before, any aspect of energy transceiver 3010 may be combined with any aspect described above.

Figure 13A:
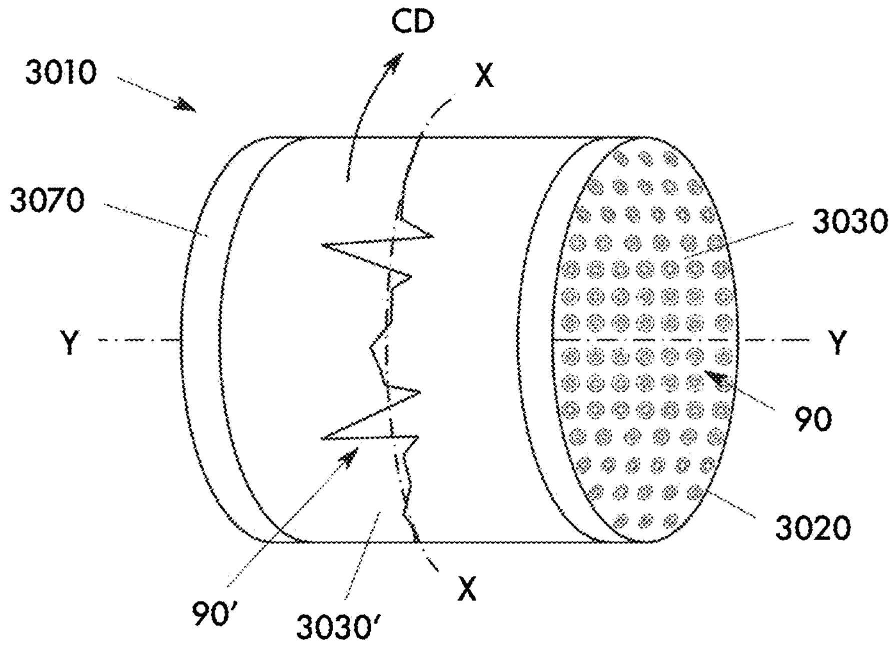
FIG. 13A depicts another exemplary communication device.

As shown in FIG. 13A, energy transceiver 3010 may include: a body 3020 and a tissue interface 2030; and an attachment element 3070, shown conceptually as a band in this example. As above, body 3020 may wrap around a circular portion of skin 2, such as around the human forearm shown in FIG. 13B. For example, as before, body 3020 may be mounted on attachment element 3070; and tissue interface 3030 may be mounted on a distal surface of body 3020, providing a curved rectangular communication area 4 and a semi-circular (e.g., less than 360°) or circular (e.g., 360°) communication direction CD for energy signal 90. In keeping with above, attachment element 3070 (e.g., the band) may be configured to maintain tissue interface 3030 against or the forearm when element 3070 is worn, allowing energy signal 90 to be output communication area 4 in signal direction SD and/or scrolled across area 4 in communication direction CD.

As described above, aspects of each energy 32 may be modified to increase the complexity of energy signal 90, and thus the amount of data transmitted therewith; and the modifiable aspects may include energy type, energy intensity, output duration, scroll rate, symbol shape, and the like, providing an incredibly broad range of obtainable complexity. Training may be required to leverage the full communicative capabilities of tissue interface 3030 and signal 90. For example, within a repetition program, the user may be trained to more easily and/or quickly to distinguish between: any number of known shapes output by one of energies 32, such as between a pip two dot pattern output with impact energy 32A and a pip four dot pattern output with energy 32A; or the same shape output with different energies 32, such as a pip five dot pattern with impact energy 32A or heat energy 32B.

Communicating more complex variations, unknown signals, and/or unknown shapes may require additional training. For example, interface 3030 may output energy signal 90 to include pip patterns in which each dot is output with a different combination of energies 32, allowing the pattern to be associated with a target, and each dot to be associated with a characteristic thereof. In the healthcare setting, for example, the pattern may be associated with a patient, and each dot may be associated with a different vital sign of the patient, providing immediate insight into patient health that may be updated continuously. Further training may be required to quickly distinguish between the characteristics communicated by each dot in these examples, particularly if energy signal 90 includes a plurality of pip patterns, as shown in FIG. 2C; or a dynamic shape, such as the echocardiogram depicted in FIGS. 13A and 13B; the plurality of echocardiograms depicted in FIG. 14A; or the alphanumeric symbol stream depicted in FIG. 14B.

Aspects of energy transceiver 3010 may be configured to provide additional communicative capabilities to, for example, assist with training. As shown in FIG. 13A, transceiver 3010 may further comprise an optical interface 3030' compatible with eyes of the user. For example, optical interface 3030' may comprise at least one display element operable to output an optical energy signal 90' to the eyes, such as a flexible LED configured to output a plurality of colors. Any display technology may be used. As shown in FIG. 13A, interface 3030' may provide a curved optical communication area that wraps around apparatus 3010 along an axis X-X and/or substantially corresponds with the communication area 4. For example, tissue interface 330 may be configured to output non-optical energy signal 90 toward skin 2 with one or more energies 32 in a first or distal direction toward skin 2; and optical interface 330' may be configured to output optical signal 90' with one or more colors in a second or proximal direction toward the eyes.

Energy transceiver 3010 may comprise a processing unit similar to any variation of processing unit 60 described herein. For example, the processing unit may be operable with tissue interface 3030 and optical interface 3030' to simultaneously communicate with nerves associated with skin 2 and the eyes by outputting signal 90 distally and signal 90' proximally at the same time. Additional training capabilities may be realized by the simultaneous outputs. For example, the user may already be trained to react to optical signal 90', whether or not signal 90 is communicated, such as when transceiver 3010 excludes interface 3030. Accordingly, by consistently outputting energy signal 90 with optical signal 90', the user may be trained to react to recognize and react to energy signal 90 with or without optical signal 90'.

Figure 13B:
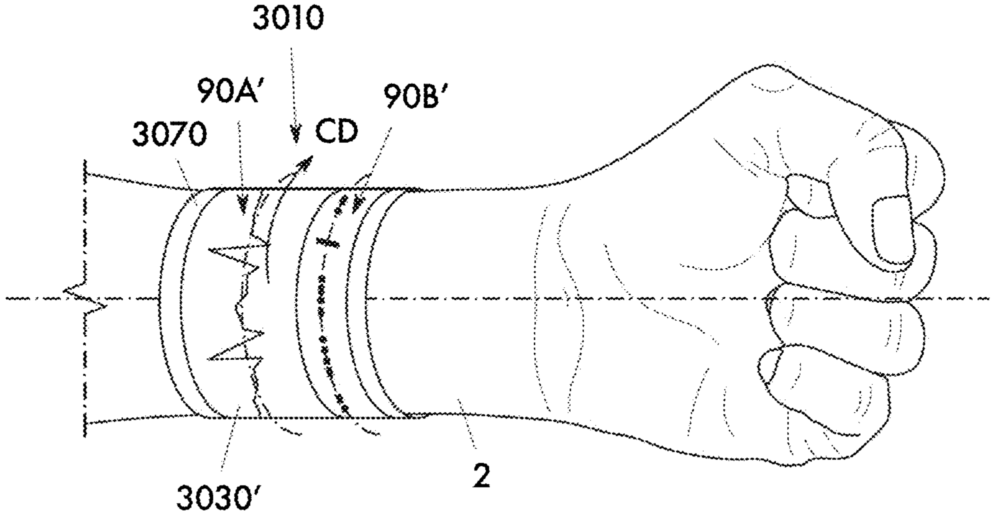
FIG. 13B depicts another view of the device of FIG. 13A.

In a healthcare setting, for example, optical signal 90' may communicate a vital sign of a patient to the eyes of a provider, such as the echocardiogram of FIG. 13A; and energy signal 90' may communicate the same vital sign to skin 2 of the provider at the same time. For example, signals 90' and 90 may be scrolled together in communication direction CD along axis X-X to simultaneously communicate aspects of the vital sign over time. As a further example, signal 90' may comprise a plurality of colors, and the output of energies 32 in signal 90 may be modified according to a color matching algorithm to communicate similar aspects to skin 2 at the same time. Reactions to different vital signs may be trained in this manner. As shown in FIG. 13B, for example, a first portion of optical interface 3030' may output a first optical signal 90A', a second portion of interface 3030' may output a second optical signal 90B', corresponding portions of tissue interface 3030 may output corresponding energy signals 90, much like interface 930 described above. As also shown in FIG. 13B, the signals 90A' and 90B' may be different, in which one may be a vital sign and other may include symbols communicating related patient data as above.

Figure 14A:
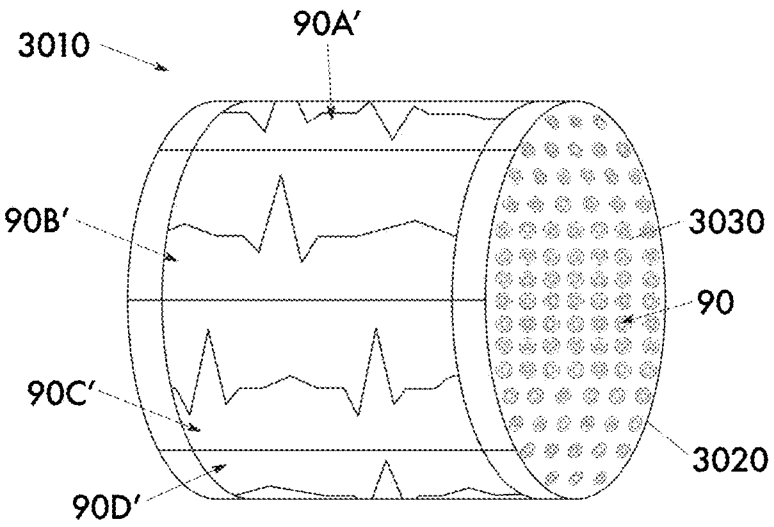
FIG. 14A depicts another view of the device of FIG. 13A.
Figure 14B:
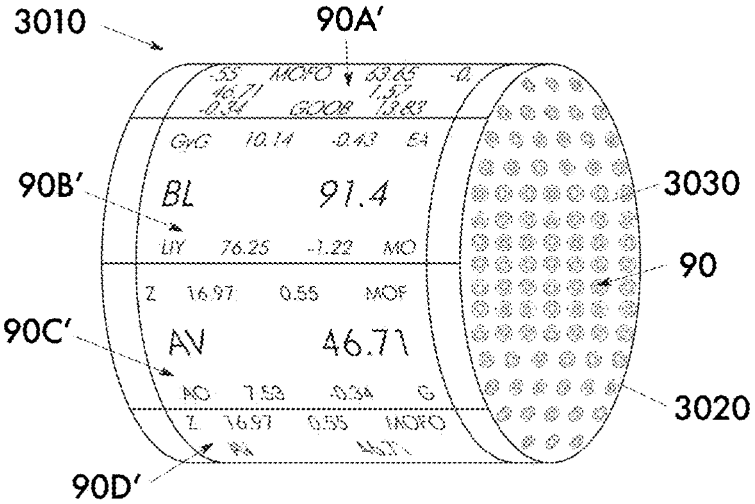
FIG. 14B depicts another view of the device of FIG. 13A.

Accordingly, by simultaneously outputting optical signal 90' together with energy signal 90, transceiver 3010 may train reactions to any stimulus, such as the exemplary vital signs and signals depicted in FIGS. 13 and 13B. As shown in FIGS. 14A and 14B, the complexity of the stimulus may be increased. For example, as shown in FIG. 14A, optical interface 3030' and tissue interface 3030 may output their respective signals in a plurality of rows arranged around axis X-X, wherein each row includes a different set of corresponding signals movable along a communication direction CD that is transverse with axis X-X. In this example, four rows are shown as outputting four different optical signals, including a first optical signal 90A', a second optical signal 90B', a third optical signal 90C', and a fourth optical signal 90D'. A corresponding set of rows and outputs may be realized by tissue interface 90.

In the healthcare setting, for example, each output of optical signals 90A', 90B', 90C' and 90D' together with its corresponding energy signal 90 may communicate a different vital sign of a different patient to a provider, training them to simultaneously monitor all of the different patients at once. As described above, aspects of each energy signal 90, such as energies 32, may be modified to communicate changes in the associated vital sign. For training purposes, the color of optical signals 90A, 90B, 90C, and 90D may be varied based on these changes so that the provider may be trained to first recognize the changes based one of the optical signals; and second recognize the same changes based on one of the energy signals based on the color matching algorithm. For example, the color matching algorithm may comprise a correspondence between visual colors and energy intensity, in which warmer colors (e.g., red) are associated with higher intensities and cooler colors (e.g., blue) are associated with lower intensities.

Another example is provided in FIG. 14B, in which each output of signals 90A', 90B', 90C' and 90D' together with its corresponding signal 90 may communicate aspects of an alphanumeric stream. As shown in FIG. 14B, for example, each alphanumeric stream may comprise a stock ticker so that the user may be trained to simultaneously monitor a plurality of tickers. As before, aspects of the different optical signals 90A', 90B', 90C', and 90'D may be modified simultaneously with aspects of their corresponding energy signals 90 to communicate changes over time.

In keeping with above, optical interface 3030' and tissue interface 3030 may be configured to individually and/or simultaneously output signals 90' and 90 to include any symbols and shapes, as well as more complex depictions, such as graphics. For example, for more complex depictions, the color matching algorithm may be used to output different combinations of energies 32 based on color.

Optical interface 3030' may comprise touchscreen capabilities allowing manipulation of signals 90 and/or 90' by interaction therewith. For example, the position of each row depicted in FIGS. 14A and 14B may be movable via a tactile interaction with interface 3030'. As shown in FIG. 13B, for example, attachment element 3070 may maintain the position of tissue interface 3030 on or adjacent skin 2 of a forearm, meaning that at least some portion of optical interface 3030' may not be aligned with the eyes of the user at all times. Accordingly, because of the dynamic capabilities of interfaces 3030 and 3030', the touchscreen capabilities of apparatus 3010 may allow the user to move a particular row into alignment with the eyes by scrolling the rows together around axis X-X, in which the outputs of signals 90A', 90B', 90C', and 90'D and corresponding energy signal 90 move with each row. Any type of touchscreen-enabled two-way communication means may be used, including buttons, sliders, textual inputs, graphic inputs, and the like.

Aspects of methods 1000, 1100, and 2100 and/or system 200 may be modified according to aspects of energy transceiver 3010. For example, any method steps described herein may be modified to comprise training and/or communication steps according to the above-described aspects of transceiver 3010. As a further example, the second energy transceiver 2014 shown in FIG. 11 may comprise transceiver 3010, which may be further operable with each of transceivers 2012, 2016, 2018, and 2020 to train the user. To provide another example, aspects of each transceiver within system 2000 also may be configured to placement at a particular sensory zone of skin 2, and transceiver 3010 may be used to both tune the respective energy signals 90 for output to each zone and train the user to react accordingly based on one or more of the signals 90. In this example, the receptive capabilities of the nerves associated with skin 2 in each zone may vary, and transceiver 3010 may be configured to operate the transceivers in system 2000 so that the most complex signals are communicated to the most receptive zones.

While principles of the present disclosure are disclosed herein with reference to illustrative aspects for particular applications, the disclosure is not limited thereto. Those having ordinary skill in the art and access to the teachings provided herein will recognize additional modifications, applications, aspects, and substitution of equivalents all fall in the scope of the aspects disclosed herein. Accordingly, the present disclosure is not to be considered as limited by the foregoing description.

The invention laimed is:

1. A communication device for communicating with a brain of a user via skin of the user, the device comprising:

a plurality of energy generators arrangeable on the skin, each energy generator of the plurality of energy generators comprising a plurality of generator elements that are independently operable to output a plurality of different energy types toward the skin, each different energy type of the plurality of different energy types being operable to communicate with the brain via the skin;

a plurality of housings attachable to the skin, each housing of the plurality of housings containing one energy generator of the plurality of energy generators and having a wall that at least partially surrounds the plurality of generator elements of the one energy generator and is operable to direct the plurality of different energy types toward the skin;

a processing unit that is separate from the plurality of energy generators, and operable to receive input data from a data source and operate one or more generating elements of the plurality of generator elements of one or more energy generators of the plurality of energy generators responsive to the input data; and a plurality of conductors extending between the processing unit and the plurality of energy generators, each conductor of the plurality of conductors being operable to transmit electricity from the processing unit to a respective energy generator of the plurality of energy generators.

2. The device of claim 1, wherein the plurality of generator elements of each energy generator of the plurality of energy generators comprise a heat generator element operable with the processing unit to convert a portion of the electricity into a heat flux recognizable by temperature receptors of the skin.

3. The device of claim 2, wherein the heat generator element comprises an electrical resistor.

4. The device of claim 2, wherein the heat generator element and at least one other generator element of the plurality of generator elements are arranged to output the heat flux and at least one other energy type of the plurality of different energy types toward an approximately same area of the skin.

5. The device of claim 1, wherein the plurality of generator elements of each energy generator of the plurality of energy generators comprise an impact generator element operable with the processing unit to convert a portion of the electricity into a mechanical movement recognizable by touch receptors of the skin.

6. The device of claim 5, wherein the impact generator element comprises a mechanical actuator.

7. The device of claim 5, wherein the touch receptors comprise Meissner's corpuscles.

8. The device of claim 1, wherein the plurality of generator elements of each energy generator of the plurality of energy generators comprise a shock generator element operable with the processing unit to convert a portion of the electricity into an electrical shock recognizable by electricity-sensitive receptors of the skin.

9. The device of claim 8, wherein the shock generator element comprises electrical contacts.

10. The device of claim 8, wherein the electricity-sensitive receptors are located in a dermis layer of the skin.

11. The device of claim 1, wherein the plurality of generator elements of each energy generator of the plurality of energy generators comprise a pressure generator element operable with the processing unit to convert a portion of the electricity into a pressure energy recognizable by pressure receptors of the skin.

12. The device of claim 11, wherein the pressure generator element comprises a transducer.

13. The device of claim 12, wherein the transducer is an electroacoustic transducer.

14. The device of claim 11, wherein the pressure receptors comprise Pacinian corpuscles.

15. The device of claim 1, wherein the plurality of generator elements of each energy generator of the plurality of energy generators comprise:

a first generator element operable with the processing unit to convert a first portion of the electricity into a heat flux recognizable by first receptors of the skin; and a second generator element operable with the processing unit to convert a second portion of the electricity into a mechanical movement recognizable by second receptors of the skin, the first receptors being different from the second receptors, the first generator element and the second generator element being independently operable relative to one another and collectively operable to output the heat flux and the mechanical movement toward an approximately same area of the skin.

16. The device of claim 1, wherein the processing unit comprises a power source operable with the plurality of conductors to transmit the electricity from the processing unit to the plurality of energy generators responsive to the input data.

17. The device of claim 16, wherein the power source comprises a rechargeable battery.

18. The device of claim 17, wherein the processing unit is operable with the rechargeable battery to modify a characteristic of the plurality of different energy types responsive to the input data.

19. The device of claim 1, comprising an attachment element operable to attach the processing unit to a portion of the skin.

20. The device of claim 1, wherein: the data source comprises a local sensor in data communication with the processing unit via the plurality of conductors and a remote data source in data communication with the processing unit via a network; and the processing unit is operable to receive the input data from the local sensor or the remote data source.

21. A communication device for communicating with a brain of a user via skin of the user, the device comprising:

a plurality of energy generators arrangeable on the skin, each energy generator of the plurality of energy generators comprising a plurality of generator elements that are independently operable relative to one another and collectively operable to output a plurality of different energy types in a signal direction toward the skin, each different energy type of the plurality of different energy types being operable to communicate with the brain via the skin, and a housing comprising a wall that at least partially surrounds the plurality of generator elements, positions the plurality of generator elements relative to one another and the skin, and is operable to direct at least one energy type of the plurality of different energy types in the signal direction toward the skin;

a processing unit that is separate from the plurality of energy generators, operable to receive input data from a data source, and operable to cause one or more generator elements of the plurality of generator elements to output one or more energy types of the plurality of different energy types responsive to the input data; and a plurality of conductors extending between the processing unit and the plurality of energy generators, each conductor of the plurality of conductors being operable to transmit electricity from the processing unit to a respective energy generator of the plurality of energy generators, wherein the plurality of generator elements of each energy generator of the plurality of energy generators comprise at least a first generator element operable with the processing unit to convert a first portion of the electricity into a heat flux recognizable by temperature receptors of the skin, and a second generator element operable with the processing unit to convert a second portion of the electricity into a mechanical movement recognizable by touch receptors of the skin.

22. The device of claim 21, wherein:

each housing comprises a skin-facing opening;

the wall of each housing defines an interior surface that at least partially surrounds the plurality of generator elements; and the plurality of generator elements are positioned to output the plurality of different energy types through the skin-facing opening in the signal direction toward an approximately same area of the skin when the housing is positioned on the skin.

23. The device of claim 21, wherein the housing of each energy generator of the plurality of energy generators is discrete from and spaced apart from the housing of each other energy generator of the plurality of energy generators.

24. The device of claim 21, comprising an attachment element operable to maintain each energy generator of the plurality of energy generators against a respective portion of the skin.

25. The device of claim 24, wherein the attachment element comprises an elastic portion operable to expand to receive the respective portion of the skin and contract to maintain each energy generator of the plurality of energy generators against its respective portion of the skin.

26. The device of claim 21, wherein each energy generator of the plurality of energy generators comprises a local controller operable with the processing unit to activate the first generator element and the second generator element.

27. The device of claim 26, wherein the plurality of conductors comprise electrical wires extending between the processing unit and the local controller of each energy generator of the plurality of energy generators.

28. The device of claim 21, wherein:

the data source comprises a local sensor in data communication with the processing unit via the plurality of conductors;

the local sensor is operable to output the input data based on a physical output related to the skin; and the processing unit is operable to modify at least one of the heat flux and the mechanical movement responsive to the input data from the local sensor.

29. The device of claim 21, wherein:

the data source comprises a remote data source in data communication with the processing unit via a wireless network;

the processing unit comprises a transceiver operable to receive the input data from the remote data source via the wireless network; and the processing unit is operable to modify at least one of the heat flux and the mechanical movement responsive to the input data from the remote data source.

30. A communication device for communicating with a brain of a user via skin of the user, the device comprising:

a plurality of energy generators arrangeable on the skin, each energy generator of the plurality of energy generators being operable independently of each other energy generator of the plurality of energy generators and comprising a plurality of generator elements that are independently operable relative to one another and collectively operable to output a plurality of different energy types toward an approximately same area of the skin, the plurality of generator elements being spaced apart from one another, each different energy type of the plurality of different energy types being operable to communicate with the brain via nerves associated with the approximately same area of the skin, a local controller operable to cause each generator element of the plurality of generator elements to output a respective energy type of the plurality of different energy types responsive to electricity, a housing comprising a wall that at least partially surrounds the local controller and the plurality of generator elements, positions the plurality of generator elements relative to one another and the approximately same area of the skin, and is operable to direct at least one energy type of the plurality of different energy types toward the approximately same area of the skin;

a processing unit that is separate from the plurality of energy generators, comprises a rechargeable battery, is operable to receive input data from a data source, and is operable to cause one or more generator elements of the plurality of generator elements to output one or more energy types of the plurality of different energy types responsive to the input data; and a plurality of conductors extending between the processing unit and the plurality of energy generators, each conductor of the plurality of conductors being operable to transmit the electricity from the rechargeable battery to the local controller of a respective energy generator of the plurality of energy generators, wherein the housing of each energy generator of the plurality of energy generators is spaced apart from the housing of each other energy generator of the plurality of energy generators;

wherein the plurality of generator elements of each energy generator of the plurality of energy generators comprise a first generator element operable with the processing unit to convert a first portion of the electricity into a heat flux recognizable by temperature receptors of the nerves associated with the approximately same area of the skin, and a second generator element operable with the processing unit to convert a second portion of the electricity into a mechanical movement recognizable by touch receptors of the nerves associated with the approximately same area of the skin.

* * * * *